US008623592B2

(12) United States Patent
Schoeberl et al.

(10) Patent No.: US 8,623,592 B2
(45) Date of Patent: Jan. 7, 2014

(54) METHODS AND SYSTEMS FOR PREDICTING RESPONSE OF CELLS TO A THERAPEUTIC AGENT

(75) Inventors: Birgit Schoeberl, Cambridge, MA (US); Brian Harms, Roslindale, MA (US); Francis David Gibbons, Lexington, MA (US); Jonathan Basil Fitzgerald, Arlington, MA (US); Matthew David Onsum, Jamaica Plain, MA (US); Ulrik Nielsen, Quincy, MA (US); William Kubasek, Belmont, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 191 days.

(21) Appl. No.: 13/058,687

(22) PCT Filed: Aug. 17, 2009

(86) PCT No.: PCT/US2009/054051
§ 371 (c)(1),
(2), (4) Date: Feb. 11, 2011

(87) PCT Pub. No.: WO2010/019952
PCT Pub. Date: Feb. 18, 2010

(65) Prior Publication Data
US 2011/0159513 A1 Jun. 30, 2011

Related U.S. Application Data

(60) Provisional application No. 61/189,053, filed on Aug. 15, 2008, provisional application No. 61/194,702, filed on Sep. 30, 2008, provisional application No. 61/208,206, filed on Feb. 20, 2009, provisional application No. 61/170,367, filed on Apr. 17, 2009.

(51) Int. Cl.
*C12Q 1/00* (2006.01)
*C12Q 1/68* (2006.01)
*G01N 33/574* (2006.01)

(52) U.S. Cl.
USPC .............................. 435/4; 435/6.14; 435/7.23

(58) Field of Classification Search
None
See application file for complete search history.

(56) References Cited

U.S. PATENT DOCUMENTS

| 5,344,760 | A | 9/1994 | Harvey et al. |
|---|---|---|---|
| 5,480,968 | A | 1/1996 | Kraus et al. |
| 5,968,511 | A | 10/1999 | Akita et al. |
| 6,696,290 | B2 | 2/2004 | Fitzpatrick et al. |
| 6,983,227 | B1 | 1/2006 | Thalhammer-Reyero |
| 7,097,840 | B2 | 8/2006 | Erickson et al. |
| 7,125,680 | B2 | 10/2006 | Singer et al. |
| 7,285,649 | B2 | 10/2007 | Akita et al. |
| 7,846,440 | B2 * | 12/2010 | Schoeberl et al. ......... 424/141.1 |
| 2002/0001587 | A1 | 1/2002 | Erickson et al. |
| 2002/0002276 | A1 | 1/2002 | Fitzpatrick et al. |
| 2002/0119148 | A1 | 8/2002 | Gerritsen et al. |
| 2002/0165193 | A1 | 11/2002 | Greene et al. |
| 2003/0040605 | A1 | 2/2003 | Siegel |
| 2003/0199020 | A1 | 10/2003 | Fitzpatrick et al. |
| 2004/0052786 | A1 | 3/2004 | Gerritsen et al. |
| 2004/0071696 | A1 | 4/2004 | Adams et al. |
| 2004/0082510 | A1 | 4/2004 | Ullrich et al. |
| 2004/0138417 | A1 | 7/2004 | Fitzpatrick et al. |
| 2004/0197332 | A1 | 10/2004 | Ullrich et al. |
| 2004/0229380 | A1 | 11/2004 | Chan-Hui et al. |
| 2004/0248151 | A1 | 12/2004 | Bacus et al. |
| 2004/0248196 | A1 | 12/2004 | Adams et al. |
| 2005/0004018 | A1 | 1/2005 | Jimeno et al. |
| 2005/0079184 | A1 | 4/2005 | Hsing-Chang et al. |
| 2005/0187745 | A1 | 8/2005 | Lurie et al. |
| 2005/0267720 | A1 | 12/2005 | Hill et al. |
| 2006/0040363 | A1 | 2/2006 | Kucherlapati et al. |
| 2006/0093603 | A1 | 5/2006 | Gerritsen et al. |
| 2006/0136139 | A1 | 6/2006 | Elcock et al. |
| 2006/0167637 | A1 | 7/2006 | Agur et al. |
| 2006/0204505 | A1 | 9/2006 | Sliwkowski et al. |

(Continued)

FOREIGN PATENT DOCUMENTS

EP 1058562 B1 12/2000
EP 1187634 B1 3/2002

(Continued)

OTHER PUBLICATIONS

Erjala et al (Clinical Cancer research, 2006, 12:4103-4111).*
Esteva et al (Pathology Oncology Research, 2001, 7:171-177).*
Rouzier et al (Clinical Cancer Research, 2005, 11:5678-5685).*
ADAPT, The Paterson Institute for Cancer Research, Probesets for ErbB1, printed Feb. 2013.*
ADAPT, The Paterson Institute for Cancer Research, Probesets for ErbB2, printed Feb. 2013.*
ADAPT, The Paterson Institute for Cancer Research, Probesets for ErbB3, printed Feb. 2013.*
ADAPT, The Paterson Institute for Cancer Research, Probesets for Betacellulin (BTC), printed Feb. 2013.*

(Continued)

*Primary Examiner* — Laura B Goddard
(74) *Attorney, Agent, or Firm* — Nelson Mullins Riley & Scarborough LLP; Jane E. Remillard, Esq.; Jill Gorny Sloper, Esq.

(57) ABSTRACT

The invention provides methods for treating patients which methods comprise methods for predicting responses of cells, such as tumor cells, to treatment with therapeutic agents. These methods involve measuring, in a sample of the cells, levels of one or more components of a cellular network and then computing a Network Activation State (NAS) or a Network Inhibition State (NIS) for the cells using a computational model of the cellular network. The response of the cells to treatment is then predicted124 based on the NAS or NIS value that has been computed. The invention also comprises predictive methods for cellular responsiveness in which computation of a NAS or NIS value for the cells (e.g., tumor cells) is combined with use of a statistical classification algorithm. Biomarkers for predicting responsiveness to treatment with a therapeutic agent that targets a component within the ErbB signaling pathway are also provided.

11 Claims, 25 Drawing Sheets

(56) References Cited

U.S. PATENT DOCUMENTS

| | | |
|---|---|---|
| 2006/0210561 A1 | 9/2006 | Baughman et al. |
| 2007/0059785 A1 | 3/2007 | Bacus et al. |
| 2007/0081994 A1 | 4/2007 | Fitzpatrick et al. |
| 2007/0092513 A1 | 4/2007 | Gerritsen et al. |
| 2007/0122407 A1 | 5/2007 | Akita et al. |
| 2007/0134251 A1 | 6/2007 | Ashkenazi et al. |
| 2007/0134252 A1 | 6/2007 | Bacus et al. |
| 2007/0190583 A1 | 8/2007 | Spector et al. |
| 2007/0254295 A1 | 11/2007 | Harvey et al. |
| 2008/0026415 A1 | 1/2008 | Rimm et al. |
| 2008/0057064 A1 | 3/2008 | Zhou |
| 2008/0090233 A1 | 4/2008 | Garcia et al. |
| 2008/0112958 A1 | 5/2008 | Mass |
| 2008/0124334 A1 | 5/2008 | Akita et al. |
| 2008/0124345 A1 | 5/2008 | Rothe et al. |
| 2008/0187948 A1 | 8/2008 | Chan-Hui et al. |
| 2008/0207615 A1 | 8/2008 | Bell et al. |
| 2008/0214584 A1 | 9/2008 | Ohta et al. |
| 2008/0254497 A1 | 10/2008 | Singh |
| 2009/0181022 A1 | 7/2009 | Nielsen et al. |
| 2009/0246206 A1 | 10/2009 | Nielsen et al. |
| 2009/0291085 A1 | 11/2009 | Schoeberl et al. |
| 2011/0027291 A1 | 2/2011 | Schoeberl et al. |
| 2011/0123523 A1 | 5/2011 | Schoeberl et al. |
| 2012/0225870 A1* | 9/2012 | Janne et al. ............... 514/234.5 |

FOREIGN PATENT DOCUMENTS

| | | |
|---|---|---|
| EP | 1283053 A1 | 2/2003 |
| EP | 1728802 A2 | 12/2006 |
| WO | 97/35885 A1 | 10/1997 |
| WO | 98/02540 A1 | 1/1998 |
| WO | 99/54800 A2 | 10/1999 |
| WO | 99/60023 A1 | 11/1999 |
| WO | 00/78347 A1 | 12/2000 |
| WO | 02/060470 A1 | 8/2002 |
| WO | 03/012072 A2 | 2/2003 |
| WO | 03/013602 A1 | 2/2003 |
| WO | 2004/003019 A3 | 1/2004 |
| WO | 2005/017493 A2 | 2/2005 |
| WO | 2006/017538 A2 | 2/2006 |
| WO | 2006/020706 A2 | 2/2006 |
| WO | 2006/044748 A2 | 4/2006 |
| WO | 2006/091209 A2 | 8/2006 |
| WO | 2007/015935 A2 | 2/2007 |
| WO | 2007/039705 A1 | 4/2007 |
| WO | 2007/041502 A2 | 4/2007 |
| WO | 2007/077028 A2 | 7/2007 |
| WO | 2007/115571 A2 | 10/2007 |
| WO | 2007/130677 A2 | 11/2007 |
| WO | 2008/064884 A1 | 6/2008 |
| WO | 2008/100624 A2 | 8/2008 |
| WO | 2008/109440 A2 | 9/2008 |
| WO | 2010/019952 A2 | 2/2010 |

OTHER PUBLICATIONS

ADAPT, The Paterson Institute for Cancer Research, Probesets for heregulin (NRG1), printed Feb. 2013.*
Ye, Dingwei et al., "Augmentation of a humanized Anti-HER2 mAb 4D6 induced growth inhibition by a human-mouse chimeric anti-EGF receptor mAb C225," Oncogene, vol. 18:731-738 (1999).
Zelada-Hedman, Moraima et al., "High Expression of the EGFR in Fibroadenomas Compared to Breast Carcinomas," Anticancer Research, vol. 14:1679-1688 (1994).
Zhang, Ke et al., "Transformation of NIH 3T3 Cells by HER3 or HER4 Receptors Requires the Presence of HER1 or HER2," The Journal of Biological Chemistry, vol. 271(7):3884-3890 (1996).
Invitation to Pay Additional Fees for Application No. PCT/US2008/002119, dated Oct. 7, 2008.
International Search Report and Written Opinion for Application No. PCT/US2008/002119, dated Dec. 3, 2008.
International Preliminary Report on Patentability for Application No. PCT/US2008/002119, dated May 18, 2009.
Information Disclosure Submission concerning Agreement between Dyax Corporation and Merrimack Pharmaceuticals.
International Search Report for Application No. PCT/US2011/028129, 4 pages, dated Oct. 13, 2011.
International Preliminary Report on Patentability and Written Opinion for Application No. PCT/US2011/028129, 8 pages, dated Sep. 11, 2012.
U.S. Appl. No. 12/281,925, filed Sep. 5, 2008, Birgit Schoeberl.
U.S. Appl. No. 12/425,874, filed Apr. 17, 2009, Birgit Schoeberl.
U.S. Appl. No. 12/545,279, filed Aug. 21, 2009, Birgit Schoeberl.
U.S. Appl. No. 12/904,492, filed Oct. 14, 2010, Birgit Schoeberl.
U.S. Appl. No. 12/207,521, filed Feb. 17, 2010, Birgit Schoeberl.
U.S. Appl. No. 13/583,949, filed Sep. 11, 2012, Victor Mayo.
U.S. Appl. No. 13/046,090, filed Mar. 11, 2011, Gabriela Garcia.
Office Action, U.S. Appl. No. 12/281,925, mailed Sep. 13, 2010.
Office Action, U.S. Appl. No. 12/281,925, mailed Mar. 4, 2010.
Office Action, U.S. Appl. No. 12/425,874, maiiled Apr. 14, 2010.
Office Action, U.S. Appl. No. 12/545,279, mailed Jun. 26, 2012.
Office Action, U.S. Appl. No. 12/545,279, mailed Sep. 9, 2011.
Office Action, U.S. Appl. No. 12/545,279, mailed May 20, 2011.
Office Action, U.S. Appl. No. 12/545,279, mailed Feb. 17, 2011.
Office Action, U.S. Appl. No. 12/707,521, mailed Jul. 31, 2012.
Office Action, U.S. Appl. No. 12/707,521, mailed Feb. 10, 2012.
Holm, Patrik et al., "Functional mapping and single chain construction of the anti-cytokeratin 8 monoclonal antibody TS1," Molecular Immunology, vol. 44:1075-1084 (2007).
Holmes, William E. et al., "Identification of Heregulin, a Specific Activator of p185erbB2," Science, vol. 256:1205-1210 (1992).
Holt, Lucy J. et al., "Domain antibodies: proteins for therapy," TRENDS in Biotechnology, Vo. 21(11):484-490 (2003).
Horan, Thomas et al., "Binding of Neu Differentiation Factor with the Extracellular Domain of Her2 and Her3," The Journal of Biological Chemistry, vol. 270(40):24604-24608 (1995).
Hsieh, AC et al., "Targeting HER proteins in cancer therapy and the role of the non-target HER3," British Journal of Cancer, vol. 97:453-457 (2007).
Htun Van Der Horst, Edward et al., "Anti-HER-3 MAbs Inhibit HER-3-Mediated Signaling in Breast Cancer Cell Lines Resistant to Anti-HER-2 Antibodies," Int. J. Cancer, vol. 115:519-527 (2005).
Issing, W.J. et al., "erbB-3, a third member of the erbB/epidermal growth factor receptor gene family: its expression in head and neck cancer cell lines," Eur. Arch. Otorhinolaryngol, vol. 250:392-395 (1993).
Jeschke, Margit et al., "Targeted Inhibition of Tumor-cell Growth by Recombinant Heregulin-toxin Fusion Proteins," Int. J. Cancer, vol. 60:730-739 (1995).
Jo, Sangmee Ahn et al., "Neuregulins are concentrated at nerve-muscle synapses and activate ACh-receptor gene expression," Nature, vol. 373:158-161 (1995).
Jones, Jennifer T. et al., "Binding specificities and affinities of egf domains for ErbB receptors," FEBS Letters, vol. 447:227-231 (1999).
Karunagaran, Devarajan et al., "ErbB-2 is a common auxiliary subunit of NDF and EGF receptors: implications for breast cancer," The EMBO Journal, vol. 15(2):254-264 (1996).
Kasprzyk, Philip G. et al., "Therapy of an Animal Model of Human Gastric Cancer Using a Combination of Anti-erbB-2 Monoclonal Antibodies," Cancer Research, vol. 52:2771-2776 (1992).
Katoh, Masaru et al., "c-erbB3 Gene Encodes Secreted as Well as Transmembrane Receptor Tyrosine Kinase," Biochemical and Biophysical Research Communications, vol. 192(3):1189-1197 (1993).
Kim, Hong-Hee et al., "Epidermal Growth Factor-dependent Association of Phosphatidylinositol 3-Kinase with the erbB3 Gene Product," The Journal of Biological Chemistry, vol. 269(40):24747-24755 (1994).
Kim, Hong-Hee et al., "Signal transduction by epidermal growth factor and heregulin via the kinase-deficient ErbB3 protein," Biochem. J., vol. 334:189-195 (1998).
Kinugasa, Yumi et al., "Neuroglycan C, a novel member of the neuregulin family," Biochemical and Biophysical Research Communications, vol. 321:1045-1049 (2004).

(56) References Cited

OTHER PUBLICATIONS

Kita, Yoshiko et al., "Bioactive Synthetic Peptide of NDF/Heregulin," Biochemical and Biophysical Research Communicatnions, vol. 210(2):441-451 (1995).

Kita, Yoshiko A. et al., "NDF/heregulin stimulates the phosphorylation of Her3/erbB3," FEBS Letters, vol. 349:139-143 (1994).

Klapper, Leah N. et al., "A subclass of tumor-inhibitory monoclonal antibodies to ErbB-2/HER2 blocks crosstalk with growth factor receptors," Oncogene, vol. 14:2099-2109 (1997).

Korabiowska, Monika et al., "Differential Expression of cerbB3 in Naevi and Malignant Melanomas," Anticancer Research, vol. 16:471-474 (1996).

Kraus, Matthias H. et al., "Demonstration of ligand-dependent signaling by the erbB-3 tyrosine kinase and its constitutive activation in human breast tumor cells," Proc. Natl. Acad. Sci. USA, vol. 90:290-2904 (1993).

Kraus, Matthias H. et al., "Isolation and characterization of ERBB3, a third member of the ERBB/epidermal growth factor receptor family: Evidence for overexpression in a dubset of human mammary tumors," Proc. Natl. Acad. Sci. USA, vol. 86:9193-9197 (1989).

Kraus, Matthias H. et al., "Overexpression of the EGF receptor-related proto-oncogene erbB-2 in human mammary tumor cell lines by different molecular mechanisms," The EMBO Journal, vol. 6(3):605-610 (1987).

Kumar, Sanjeev et al., "Molecular Cloning and Expression of the Fabs of Human Autoantibodies in *Escherichia coli*," The Journal of Biological Chemistry, vol. 275(45):35129-35136 (2000).

Lee, Hakjoo et al., "A Naturally Occurring Secreted Human ErbB3 Receptor Isoform Inhibits Heregulin-stimulated Activation of ErbB2, ErbB3, and ErbB4,"Cancer Research, vol. 61:4467-4473 (2001).

Lee, Hakjoo et al., "Isolation and characterization of four alternate c-erbB3 transcripts expressed in ovarian carcinoma-derived cell lines and normal human tissues," Oncogene, vol. 6:3243-3252 (1998).

Lee-Hoeflich, Si Tuen et al., "A Central Role for HER3 in HER2-Amplified Breast Cancer: Implications for Targeted Therapy," Cancer Res., vol. 68(14):5878-5887 (2008).

Lemoine, Nicholas R. et al., "The erbB-3 Gene in Human Pancreatic Cancer," Journal of Pathology, vol. 168:269-273 (1992).

Levi, Allan D.O. et al., "The Influence of Heregulins on Human Schwann Cell Proliferation," The Journal of Neuroscience, vol. 15(2):1329-1340 (1995).

Lewis, Gail D. et al., "Growth Regulation of Human Breast and Ovarian Tumor Cells by Herebulin: Evidence for the Requirement of ErbB2 as a Critical Component in Mediating Heregulin Responsiveness," Cancer Research, vol. 56:1457-1465 (1996).

Little, M. et al., "Of mice and men: hybridoma and recombinant antibodies," Immunology Today, vol. 21(8):364-370 (2000).

Lu, Dan et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Research, vol. 61:7002-7008 (2001).

MacCallum, Robert M. et al., "Antibody-antigen Interactions: Contact Analysis and Binding Site Topography," J. Mol. Biol., vol. 262:732-745 (1996).

Marchionni, Mark A. et al., "Glial growth factors are alternatively spliced erbB2 ligands expressed in the nervous system," Nature, vol. 362:312-318 (1993).

Marte, Barbara M. et al., "Neu Differentiation Factor/Heregulin Modulates Growth and Differentiation of HC11 Mammary Epithelial Cells," Molecular Endocrinology, vol. 9:14-23 (1995).

McCall, Adrian M. et al., "Increasing the Affinity for Tumor Antigen Enhances Bispecific Antibody Cytotoxicity," The Journal of Immunology, vol. 166:6112-6117 (2001).

Morrissey, Thomas K. et al., "Axon-induced mitogenesis of human Schwann cell involves heregulin and p185erbB2," Proc. Natl. Acad. Sci. USA, vol. 92:1431-1435 (1995).

Moscosco, Lisa M. et al., "Synapse-Associated Expression of an Acetylcholine Receptor-Inducing Protein, ARIA/Heregulin, and Its Putative Receptors, ErbB2 and ErbB3, in Developing Mammalian Muscle," Developmental Biology, vol. 172:158-169 (1995).

Myers, Russell B. et al., "Expression of p160erbB-3 and p185erbB-2 in Prostatic Intraepithelial Neoplasia and Prostatic Adenocarcinoma," Journal of the National Cancer Institute, vol. 86(15):1140-1145 (1994).

Nie, Lin et al., "Efficacy of MM121 in ER+ and triple negative breast cancer studies," Proceedings of the American Association for Cancer Research, vol. 51:436, Poster Presentation No. 1806 (2010).

Nielsen, Ulrik B. et al., "Targeting of Bivalent Anti-ErbB2 Diabody Antibody Fragments to Tumor Cells Is Independent of the Intrinsic Antibody Affinity," Cancer Research, vol. 60:6434-6440 (2000).

Oikawa, Tetsuro et al., "Frequent Expression of Genes for Receptor Tyrosine Kinases and Their Ligands in Human Pancreatic Cancer Cells," International Journal of Pancreatology, vol. 18(1):15-23 (1995).

Orr-Urtreger, Avi et al., "Neural expression and chromosomal mapping of Neu differentiation factor to 8p12-p21," Proc. Natl. Acad. Sci. USA, vol. 90:1867-1871 (1993).

Peles, Elior et al., "Cell-type specific interaction of Neu differentiation factor (NDF/heregulin) with Neu/HER-2 suggests complex ligand-receptor relationships," The EMBO Journal, vol. 12(3):961-971 (1993).

Pierce, Jacalyn H. et al., "Signal Transduction Through the EGF Receptor Transfected in IL-3-Dependent Hematopoietic Cells," Science, vol. 239:628-631 (1988).

Pinkas-Kramarski, Ronit et al., "Diversification of Neu differentiation factor and epidermal growth factor signaling by combinatorial receptor interactions," The EMBO Journal, vol. 15(10):2452-2467 (1996).

Pinkas-Kramarski, Ronit et al., "Neu Differentiation Factor/Neuregulin Isoforms Activate Distinct Receptor Combinations," The Journal of Biological Chemistry, vol. 271(32):19029-19032 (1996).

Pinkas-Kramarski, Ronit et al., "The oncogenic ErbB-2/ErbB-3 heterodimer is a surrogate receptor of the epidermal growth factor and betacellulin," Oncogene, vol. 16:1249-1258 (1998).

Plowman, Gregory D. et al., "Heregulin induces tyrosine phosphorylation of HER4/p180erbB4," Nature, vol. 366:473-475 (1993).

Plowman, Gregory D. et al., "Ligand-specific activation of HER4/p180erbB4, a fourth member of the epidermal growth factor receptor family," Proc. Natl. Acad. Sci. USA, vol. 90:1746-1750 (1993).

Plowman, Gregory D. et al., "Molecular cloning and expression of an additional epidermal growth factor receptor-related gene," Proc. Natl. Acad. Sci. USA, vol. 87:4905-4909 (1990).

Poller, D.N. et al., "Production and Characterization of a Polyclonal Antibody to the c-erbB-3 Protein: Examination of c-erbB-3 Protein Expression in Adenocarcinomas," Journal of Pathology, vol. 168:275-280 (1992).

Presta, Leonard, "Antibody engineering for therapeutics," Current Opinion in Structural Biology, vol. 13:519-525 (2003).

Prigent, S.A. et al., "Expression of the c-erbB-3 protein in normal human adult and fetal tissues," Oncogene, vol. 7:1273-1278 (1992).

Prigent, Sally A. et al., "The Type 1 (EGFR-related) Family of Growth Factor Receptors and Their Ligands," Progress in Growth Factor Research, vol. 4:1-24 (1992).

Quinn, C.M. et al., "c-erbB-3 protein expression in human breast cancer: comparison with othe tumour variables and survival," Histopathology, vol. 25:247-252 (1994).

Rajkumar, T. et al., "A monoclonal antibody to the human c-erbB3 protein stimulates the anchorage-independent growth of breast cancer cell lines," Br. J. Cancer, vol. 70:459-465 (1994).

Rajkumar, Thangarajan et al., "Experssion of the C-erbB-3 Protein in Gastrointestinal Tract Tumours Determined by Monoclonal Antibody RTJ1," Journal of Pathology, vol. 170:271-278 (1993).

Rajkumar, T. et al., "Prevelance of c-erbB3 expression in squamous cell carcinomas of the cervix as determined by the monoclonal antibody RTJ2," International Journal of Oncology, vol. 6:105-109 (1995).

Rajkumar, Thangarajan et al., "The Type I growth factor receptors in human breast cancer," Breast Cancer Research and Treatment, vol. 29:3-9 (1994).

(56) References Cited

OTHER PUBLICATIONS

Ross, Jeffrey S. et al., "The HER-2/neu Oncogene in Breast Cancer: Prognostic Factor, Predictive Factor, and Target for Therapy," The Oncologist, vol. 3:237-252 (1998).
Rudikoff, Stuart et al., "Single amino acid substitution altering antigen-binding specificity," Proc. Natl. Acad. Sci. USA, vol. 79:1979-1983 (1982).
Rudnick, Stephen I. et al., "Affinity and Avidity in Antibody-Based Tumor Targeting," Cancer Biotherapy and Radiopharmaceuticals, vol. 24(2):155-161 (2009).
Sadick, Michael D. et al., "Analysis of Heregulin-Induced ErbB2 Phosphorylation wtih a High-Throughput Kinase Receptor Activation Enzyme-Linked Immunosorbant Assay," Analytical Biochemistry, vol. 235:207-214 (1996).
Salomon, David S. et al., "Epidermal growth factor-related peptides and their receptors in human malignancies," Critical Reviews in Oncology/Hematology, vol. 19:183-232 (1995).
Sanidas, E.E. et al., "Expression of the c-erbB-3 Gene Product in Gastric Cancer," Int. J. Cancer, vol. 54:935-940 (1993).
Schaefer, Karl-Ludwig et al., "Constitutive Activation of Neuregulin/ERBB3 Signaling Pathway in Clear Cell Sarcoma of Soft Tissue," Neoplasia, vol. 8(7):613-622 (2006).
Schaefer, Karl-Ludwig et al., "Expression Profiling of t(12;22) Positive Clear Cell Sarcoma of Soft Tissue Cell Lines Reveals Characteristic Up-Regulation of Potential New Marker Genes Including ERBB3," Cancer Research, vol. 64:3395-3405 (2004).
Schmidt, M. et al., "Targeted inhibition of tumour cell growth by a bispecific single-chain toxin containing an antibody domain and TGFa," British Journal of Cancer, vol. 74:853-862 (1996).
Schneider, Bryan P. et al., "Triple-Negative Breast Cancer: Risk Factors to Potential Targets," Clin. Cancer Res., vol. 14(24):8010-8018 (2008).
Schoeberl, Birgit et al., "An ErbB3 Antibody, MM-121, Is Active in Cancers with Ligand-Dependent Activation," Cancer Res., vol. 70(6):2485-2494 (2010).
Semba, Kentaro et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci. USA, vol. 82:6497-6501 (1985).
Shintani, Satoru et al., "Expression of C-erbB Family Gene Products in Adenoid Cystic Carcinoma of Salivary Glands: An Immunohistochemical Study," Anticancer Research, vol. 15:2623-2626 (1995).
Shintani, Satoru et al., "Prognostic significance of ERRB3 overexpression in oral squamous cell carcinoma," Cancer Letters, vol. 95:79-83 (1995).
Simpson, Barbara J.B. et al., "c-erbB Growth-factor-receptor Proteins in Ovarian Tumours," Int. J. Cancer (Pred. Oncol.), vol. 64:202-206 (1995).
Simpson, BJB et al., "c-erbB-3 protein expression in ovarian tumours," British Journal of Cancer, vol. 71:758-762 (1995).
Singer, Elizabeth et al., "Identification of a Heregulin Binding Site in HER3 Extracellular Domain," The Journal of Biological Chemistry, vol. 276(47):44266-44274 (2001).
Skinner, Ann et al., "Transcriptional regulation of the c-erbB-3 gene in human breast carcinoma cell lines," Oncogene, vol. 8:3393-3401 (1993).
Slamon, Dennis J. et al., "Human Breast Cancer: Correlation of Relapse and Survival with Amplification of the HER-2/neu Oncogene," Science, vol. 235:177-182 (1987).
Slamon, Dennis J. et al., "Studies of the HER-2/neu Proto-oncogene in Human Breast and Ovarian Cancer," Science, vol. 244:707-712 (1989).
Sliwkowski, Mark X. et al., "Coexpression of erbB2 and erbB3 Proteins Reconstitutes a High Affinity Receptor for Heregulin," The Journal of Biological Chemistry, vol. 269(2):14661-14665 (1994).
Smith, B.L. et al., "The efficacy of Herceptin therapies is influenced by the expression of other erbB receptors, their ligands and the activation of downstream signalling proteins," British Journal of Cancer, vol. 91:1190-1194 (2004).
Smith-Gill, Sandra J. et al., "Contributions of Immunoglobulin Heavy and Light Chains to Antibody Specificity for Lysozyme and Two Haptens," The Journal of Immunology, vol. 139:4135-4144 (1987).
Soltoff, Stephen P. et al., "ErbB3 Is Involved in Activation of Phosphatidylinositol 3-Kinase by Epidermal Growth Factor," Molecular and Cellular Biology, vol. 14(6):3550-3558 (1994).
Song, Mi-Kyung et al., "Light Chain of Natural Antibody Plays a Dominant Role in Protein Antigen Binding," Biochemical and Biophysical Research Communications, vol. 268:390-394 (2000).
Surmacz, Eva, "Growth factor receptors as therapeutic targets: strategies to inhibit the insulin-like growth factor I receptor," Oncogene, vol. 22:6589-6597 (2003).
Thurber, Greg M. et al., "Antibody tumor penetration: Transport opposed by systemic and antigen-mediated clearance," Advanced Drug Delivery Reviews, vol. 60:1421-1434 (2008).
Tzahar, Eldad et al., "A Hierarchical Network of Interreceptor Interactions Determines Signal Transduction by Neu Differentiation Factor/Neuregulin and Epidermal Growth Factor," Molecular and Cellular Biology, vol. 16 (10):5276-5287 (1996).
Tzahar, Eldad et al., "ErbB-3 and ErbB-4 Function as the Respective Low and High Affinity Receptors of All Neu Differentiation Factor/Heregulin Isoforms," The Journal of Biological Chemistry, vol. 269(40):25226-25233 (1994).
Ullrich, Axel et al., "Signal Transduction by Receptors with Tyrosine Kinase Activity," Cell, vol. 61:203-212 (1990).
Vaidya, Pradeep et al., "Overexpression of Different Members of the Type 1 Growth Factor Receptor Family and Their Association with Cell Proliferation in Periampullary Carcinoma," Journal of Pathology, vol. 178:140-145 (1996).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Voskoglou-Nomikos, Theodora et al., "Clinical Predictive Value of the in Vitro Cell Line, Human Xenograft, and Mouse Allograft Preclinical Cancer Models," Clinical Cancer Research, vol. 9:4227-4239 (2003).
Wainstein, Mark A. et al., "CWR22: Androgen-dependent Xenograft Model Derived from a Primary Human Prostatic Carcinoma," Cancer Research, vol. 54:6049-6052 (1994).
Wallasch, Christian et al., "Heregulin-dependent regulation of HER2/neu oncogenic signaling by heterodimerization with HER3," The EMBO Journal, vol. 14(17):4267-4275 (1995).
Ward, E. Sally et al., "Binding activities of a repertoire of single immunoglobulin variable domains secreted from *Escherichia coli*," Nature, vol. 341:544-546 (1989).
Wingens, Miriam et al., "Structural Analysis of an Epidermal Growth Factor/Transforming Growth Factor-a Chimera with Unique ErbB Binding Specificity," The Journal of Biological Chemistry, vol. 278(40):39114-39123 (2003).
Wu, Dianging et al., "Human Epidermal Growth Factor (EGF) Receptor Sequence Recognized by EGF Competitive Monoclonal Antibodies," The Journal of Biological Chemistry, vol. 264(29):17469-17475 (1989).
Wu, Herren et al., "Humanization of a Murine Monoclonal Antibody by Simultaneous Optimization of Framework and CDR Residues," J. Mol. Biol., vol. 294:151-162 (1999).
Yamamoto, Tadashi et al., "Similarity of protein encoded by the human c-erb-B-2 gene to epidermal growth factor receptor," Nature, vol. 319:230-234 (1986).
Aaronson, S.A. et al., "Growth factor-regulated pathways in epithelial cell proliferation," Am. Rev. Respir. Dis., vol. 142(6 pt. 2):S7-S10 (1990).
Alberts, Bruce et al., Molecular Biology of the Cell, Third Edition, Garland Publishing, Inc., New York, pp. 897-899 (1994).
Alimandi, Maurizio et al., "Cooperative signaling of ErbB3 and ErbB2 in neoplastic transformation and human mammary carcinomas," Oncogene, vol. 10:1813-1821 (1995).
Alimandi, Maurizio et al., "Epidermal growth factor and betacellulin mediate signal transduction through co-expressed ErbB2 adn ErbB3 receptors," The EMBO Journal, vol. 16(18):5608-5617 (1997).

(56) References Cited

OTHER PUBLICATIONS

ATCC, "AdrR," retrieved online at: http://www.atcc.org/ATCCAdvancedCatalogSearch/AllCollectionSearch/tabid/454/Default.aspx (2011).
Balint, Robert F. et al., "Antibody engineering by parsimonious mutagenesis," Gene, vol. 137:109-118 (1993).
Baselga, Jose et al., "Novel anticancer targets: revisiting ERBB2 and discovering ERBB3," Nature Reviews Cancer, vol. 9(7):463-475 (2009).
Becerril, Baltazar et al., "Toward Selection of Internalizing Antibodies from Phage Libraries," Biochemical and Biophysical Research Communications, vol. 255:386-393 (1999).
Beckman, Robert A. et al., "Antibody Constructs in Cancer Therapy, Protein Engineering Strategies to Improve Exposure in Solid Tumors," Cancer, vol. 109:170-179 (2007).
Beerli, Roger R. et al., "Neu Differentiation Factor Activation of ErbB-3 and ErbB-4 Is Cell Specific and Displays a Differential Requirement for ErbB-2," Molecular and Cellular Biology, vol. 15(12):6496-6505 (1995).
Bodey, Bela et al., "Immunophenotypically Varied Cell Subpopulations in Primary and Metastatic Human Melanomas. Monoclonal Antibodies for Diagnosis, Detection of Neoplastic Progression and Receptor Directed Immunotherapy," Anticancer Research, vol. 16:517-532 (1996).
Bortoletto, Nicola et al., "Optimizing anti-CD3 affinity for effective T cell targeting against tumor cells," Eur. J. Immunol., vol. 32:3102-3107 (2002).
Bostwick, David G., "c-erbB-2 Oncogene Expression in Prostatic Intraepithelial Neoplasia: Mounting Evidence for a Precursor Role," Journal of the National Cancer Institute, vol. 86(15):1108-1110 (1994).
Brotherick, Ian et al., "A flow cytometric study of c-erbB-3 expression in breast cancer," Cancer Immunol. Immunother., vol. 41:280-286 (1995).
Campbell, Marcia R. et al., "HER3 Comes of Age: New Insights into the Functions and Role in Signaling, Tumor Biology, and Cancer Therapy," Clin. Cancer Res., vol. 16(5):1373-1383 (2010).
Carraway, Kermit L. III et al., "A Neu Acquaintance for ErbB3 and ErbB4: A Role for the Receptor Heterodimerization in Growth Signaling," Cell, vol. 78:5-8 (1994).
Carraway, Kermit L. III et al., "Heregulin Stimulates Mitogenesis and Phosphatidylinositol 3-Kinase in Mouse Fibroblasts Transfected with erbB2/neu and erbB3," The Journal of Biological Chemistry, vol. 270(13):7111-7116 (1995).
Carraway, Kermit L. III et al., "The erbB3 Gene Product Is a Receptor for Heregulin," The Journal of Biological Chemistry, vol. 269(19):14303-14306 (1994).
Casset, Florence et al., "A peptide mimetic of an anti-CD4 monoclonal antibody by rational design," Biochemical and Biophysical Research Communications, vol. 307:198-205 (2003).
Cespedes, Maria Virtudes et al., "Mouse models in oncogenesis and cancer therapy," Clin. Transl. Oncol., vol. 8 (5):318-329 (2006).
Chen, Xiaomei et al., "An Immunological Approach Reveals Biological Differences between the Two NDF/Heregulin Receptors, ErbB-3 and ErbB-4," The Journal of Biological Chemistry, vol. 271(13):7620-7629 (1996).
Chen, Yvonne et al., "Selection and Analysis of an Optimized AntiVEGF Antibody: Crystal Structure of an Affinity-matured Fab in Complex with Antigen," J. Mol. Biol., vol. 293:865-881 (1999).
Ciardiello, Fortunato et al., "Differential expression of epidermal growth factor-related proteins in human colorectal tumors," Proc. Natl. Acad. Sci. USA, vol. 88:7792-7796 (1991).
Davies, Jullian et al., "Affinity improvement of single antibody VH domains: residues in all three hypervariable regions affect antigen binding," Immunotechnology, vol. 2:169-179 (1996).
Dennis, Carina, "Off by a whisker," Nature, vol. 442:739-741 (2006).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
Di Fiore, Pier Paolo et al., "Mechanisms involving an expanding erbB/EGF receptor family of tyrosine kinases in human neoplasia," Genes, Oncogenes, and Hormones, Robert B. Dickson, Ed., Kluwer Academic Publishers, pp. 139-160 (1992).
Dorvillius, Mylene et al., "Targeting of Human Breast Cancer by a Bispecific Antibody Directed against Two Tumour-Associated Antigens: ErbB-2 and Carcinoembryonic Antigen," Tumor Biol., vol. 23:337-347 (2002).
Drebin, Jeffrey A. et al., "Monoclonal antibodies reactive with distinct domains of the neu oncogene-encoded p185 molecule exert synergistic anti-tumor effects in vivo," Oncogene, vol. 2:273-277 (1988).
Eccles, Suzanne A. et al., "Significance of the c-erbB Family of Receptor Tyrosine Kinases in Metastatic Cancer and Their Potential as Targets for Immunotherapy," Invasion Metastasis, vol. 14:337-348 (1995).
Ethier, Stephen P. et al., "erbB Family Receptor Expression and Growth Regulation in a Newly Isolated Human Breast Cancer Cell Line," Cancer Research, vol. 56:899-907 (1996).
Faksvåg, Dagny R. et al., "Expression of c-erbB-3 and c-erbB-4 Proteins in Papillary Thyroid Carcinomas," Cancer Research, vol. 56:1184-1188 (1996).
Fendly, Brian M. et al., "Characterization of Murine Monoclonal Antibodies Reactive to Either the Human Epidermal Growth Factor Receptor or HER2/neu Gene Product," Cancer Research, vol. 50:1550-1558 (1990).
Fiddes, Rodney J. et al., "Heregulin (HRG)-induced Mitogenic Signaling and Cytotoxic Activity of a HRG/PE40 Ligand Toxin in Human Breast Cancer Cells," Cell Growth & Differentiation, vol. 6:1567-1577 (1995).
Fitzpatrick, V. Danial et al., "Formation of a high affinity heregulin binding site using the soluble extracellular domains of ErbB2 with ErbB3 or ErbB4," FEBS Letters, vol. 431:102-106 (1998).
Foley, John et al., "EGFR Signaling in Breast Cancer: Bad to the Bone," Semin. Cell. Dev. Biol., vol. 21(9):951-960 (2010).
Francois, Christine et al., "Antibodies directed at mouse IL-2-R a and b chains act in synergy to abolish T-cell proliferation in vitro and delayed type hypersensitivity reaction in vivo," Transpl. Int., vol. 9:46-50 (1996).
Friess, Helmut et al., "Enhanced erbB-3 Expression in Human Pancreatic Cancer Correlates with Tumor Progression," Clinical Cancer Research, vol. 1:1413-1420 (1995).
Friess, H. et al., "Pancreatic cancer: the potential clinical relevance of alterations in growth factors and their receptors," J. Mol. Med., vol. 74:35-42 (1996).
Fuchs, C.S., "Gastric Carcinoma," The New England Journal of Medicine, vol. 333(21):1426-1428 (1995).
Fujimori, Kenji et al., "A Modeling Analysis of Monoclonal Antibody Percolation Through Tumors: A Binding-Site Barrier," J. Nucl. Med., vol. 31:1191-1198 (1990).
Garnett, Daniel C. et al., "Heregulin-stimulated Signaling in Rat Pheochromocytoma Cells," The Journal of Biological Chemistry, vol. 270(32):19022-19027 (1995).
Gorgoulis, V. et al., "Molecular and immunohistochemical study of class I growth factor receptors in squamous cell lung carcinomas," Abstracts / Lung Cancer, vol. 14:381 (1996).
Grasso, Adam W. et al., "ErbB kinases and NDF signaling in human prostate cancer cells," Oncogene, vol. 15:2705-2716 (1997).
Gullick, W.J., "The c-erbB3/HER3 Receptor in Human Cancer," Cancer Surveys, vol. 27:339-349 (1996).
Guy, Pamela M. et al., "Insect cell-expressed p180erbB3 possesses an impaired tyrosine kinase activity," Proc. Natl. Acad. Sci. USA, vol. 91:8132-8136 (1994).
Harris, Lyndsay N. et al., "Molecular subtypes of breast cancer in reltaion to paclitaxel response and outcomes in women with metastatic disease: results from CALGB 9342," Breast Cancer Research, vol. 8(6):R66, 12 pages, doi:10.1186/bcr1622 (2006).

(56) References Cited

OTHER PUBLICATIONS

Heldin, Carl-Henrik, "Dimerization of Cell Surface Receptors in Signal Transduction," Cell, vol. 80:213-223 (1995).

Hellyer, Nathan J. et al., "Cloning of the rat ErbB3 cDNA and characterization of the recombinant protein," Gene, vol. 165:279-284 (1995).

Hofmann, Francesco et al., "Blocking insulin-like growth factor-I receptor as a strategy for targeting cancer," DDT, vol. 10(15):1041-1047 (2005).

Schoeberl, Birgit et al., "Computational modeling and simulation lead to the development of MM-121, a human monoclonal antibody ErbB3 antagonist," 99th AACR Annual Meeting, Poster Presentation Abstract No. 1638 (2008).

Schoeberl, Birgit et al., "MM-121:a human monoclonal antibody ErbB3 antagonist," 99th AACR Annual Meeting, Poster Presentation Abstract No. 3974 (2008).

Erjala, Kaisa et al., "Signaling via ErbB2 and ErbB3 Associates with Resistance and Epidermal Growth Factor Receptor (EGFR) Amplification with Sensitivity to EGFR Inhibitor Gefitinib in Head and Neck Squamous Cell Carcinoma Cells," Clin. Cancer Res., vol. 12(13):4103-4111 (2006).

International Search Report and Written Opinion for Application No. PCT/US2009/054051, dated May 4, 2010.

International Preliminary Report on Patentability for Application No. PCT/US2009/054051, dated Feb. 15, 2011.

Office Action, U.S. Appl. No. 12/707,521, Birgit Schoeberl, filed Feb. 17, 2010, mailed Mar. 29, 2013.

\* cited by examiner

METHODS AND SYSTEMS FOR PREDICTING RESPONSE OF CELLS TO A THERAPEUTIC AGENT

BACKGROUND OF THE INVENTION

Considerable advances have been made in the development of targeted therapies for the treatment of cancer and other diseases. Such targeted therapies include monoclonal antibodies that bind to antigens that are specifically or preferentially expressed on tumor cells and small molecule drugs that specifically interfere with discrete components of signaling pathways active in tumor cells. For example, cetuximab (Erbitux®) is a monoclonal antibody that targets the epidermal growth factor receptor (EGFR, also known as ErbB1 or HER1) that is expressed in at least certain colon cancers and head and neck cancers. Also for example, imatinib (Gleevec®) is a small molecule that targets the BCR-Abl tyrosine kinase, which is expressed, and acts as an oncogenic factor, in certain chronic myeloid leukemias and is an abnormal variant of a benign cellular protein. While such targeted therapies have been shown to be effective in some patients, the response rate is never 100%. For example, the average response rate for cetuximab monotherapy is only around 15-20% of patients, even when tumors are known to express ErbB1 (EGFR). Thus, mere expression of ErbB1 (the antigen targeted by the cetuximab antibody) in a tumor does not guarantee responsiveness to cetuximab.

Thus, while targeted therapies are very promising, the variable response rate of patients to such therapies, combined with the side effects associated with such therapies and the typical high cost of such therapies, indicates that methods for treating patients which involve predicting which patients are likely to respond to therapeutic treatment and only administering the treatment to patients who are predicted to respond are highly desirable. One approach that has been taken has been to try to identify genetic markers (e.g., mutations or alleles) that correlate with responsiveness to therapy. In this approach, a sample from the patient is genotyped prior to treatment to determine whether the patient carries a genetic marker(s) that is indicative of responsiveness to therapy. Another approach that has been taken is to try to identify protein biomarkers that correlate with responsiveness to therapy. In this approach, protein expression is determined in a sample from the patient prior to treatment to determine whether the patient expresses one or more protein biomarkers that are indicative of responsiveness to therapy.

Both of the aforementioned approaches can be considered to be "direct" marker approaches, wherein the presence (or absence, or level of expression) of the marker(s) (e.g., BCR-Abl or ErbB1) directly being measured has been demonstrated to correlate with responsiveness or non-responsiveness to therapy. Furthermore, both of these approaches rely on the use of markers that are sufficiently stable in cells such that they can be reliably measured or quantitated in a sample that has been isolated from the patient. Given that there may be a considerable time lag between when a sample is isolated from a patient and when the marker(s) is measured in the sample, such "direct" marker approaches described above typically require the use of genetic or protein markers that are not subject to degradation or alteration over time when samples are subjected to conventional processing and handling. While such stable, "direct" markers that are predictive of responsiveness to certain therapeutic agents have been identified, it is unclear whether such markers can be identified for all therapeutic agents.

It is thought that tumors are driven to grow by a set of ligand activated signaling pathways, which are usually activated by ligands binding to their cognate receptors, inducing the phosphorylation of the receptor itself as well as of downstream kinases, leading to further phosphorylation of downstream components of the pathway. These kinases trigger cell survival and proliferation. Accordingly, activation of the signaling pathway leads to alteration of intracellular components, in particular protein phosphorylation. The phosphorylation signature of the receptors expressed on tumor tissue can help to identify the main pathways that drive a particular tumor's progression. However, phosphoproteins can be very labile and the phosphorylation can dissipate quickly after surgery if the tissue sample is not immediately and rapidly frozen (or, in some cases, formalin fixed). Moreover, even where it is possible to reliably measure levels of one or more phosphoproteins in a sample of a particular tumor, the predictive value of the presence or absence of any particular phosphoprotein regarding efficacy of treatment of such a tumor with any particular therapeutic agent is generally unknown. Therefore, while phosphoprotein profiles contain important information about the pathways driving tumor progression, such phosphoprotein profiles currently are not widely used as biomarkers for predicting responsiveness to therapeutic treatment.

Accordingly, new methods for determining levels of various phosphoproteins and of using such levels and other tumor cell characteristics for predicting the responsiveness of individual tumors to particular therapeutic agents are needed to improve the therapeutic and cost effectiveness of cancer therapies.

SUMMARY OF THE INVENTION

Herein provided are methods for predicting responsiveness of cells, in particular neoplastic cells such as tumor cells (e.g., benign tumor cells or malignant tumor cells) and malignant cells that are not tumor cells, to therapeutic agents and methods for treating patients having such tumors with therapeutic agents.

In one aspect, methods are provided for treating a patient for a malignancy with an anti-neoplastic therapeutic agent by obtaining a sample of malignant cells from the patient, determining certain biochemical characteristics of the cells in the sample, and subsequently administering at least one anti-neoplastic therapeutic agent to the patient. In certain embodiments, the biochemical characteristics are the level of at least one biomarker; in further embodiments, the level(s) of the biomarker(s) are determined by measuring levels of other, more stable, biochemical compounds and then using a computer modeling paradigm to determine the levels of the biomarker(s) of interest. The therapeutic agent is selected on the basis of the level(s) of the biomarker(s); certain agents are administered only when specific level(s) of biomarker(s) are exceeded.

In certain embodiments, methods are provided for a treating a patient having a neoplastic tumor with an anti-neoplastic therapeutic agent, comprising: obtaining a sample of the tumor (e.g., a biopsy sample or a resected sample) comprising tumor cells, determining a level of phosphorylated ErbB3 (phospho-ErbB3, pErbB3) in the sample, and subsequently administering at least one anti-neoplastic therapeutic agent to the patient. An anti-ErbB3 therapeutic agent is administered if the sample cells are found to contain at least a minimum level of pErbB3; an anti-neoplastic therapeutic agent that is not an anti-ErbB3 therapeutic agent is administered, and an anti-ErbB3 therapeutic agent is not administered to the patient if the sample cells are found not to contain at least the minimum level of pErbB3. Preferred anti-ErbB3 pharmaceutical agents are anti-ErbB3 antibodies. In certain embodiments of this method, the level of ErbB3 in the sample cells is determined inferentially by measuring levels of other, more stable, biomarkers and using a computerized method using a computing system to generate a computer model to compute (based on actual empirically measured levels of other biomarkers in the sample cells) a Network Activation State that determines, by simulation, the levels of pErbB3 in the sample cells.

Within one such embodiment, methods are provided for a treating a patient having a malignant tumor, comprising: obtaining a sample of the tumor, determining a level of pErbB3 in the sample, and subsequently administering at least one anti-neoplastic therapeutic agent to the patient, wherein, if the level of pErbB3 determined in the sample is no lower than 50% of a level of pErbB3 measured in a culture of ACHN renal cancer cells (ATCC No. CRL-1611) following culture for 20-24 hours in serum-free medium (e.g., RPMI) then the at least one anti-neoplastic therapeutic agent subsequently administered to the patient comprises an anti-ErbB3 antibody, and if the level of pErbB3 determined in the sample is lower than 50% of the level of pErbB3 measured in the culture of ACHN renal cancer cells then the at least one anti-neoplastic therapeutic agent subsequently administered to the patient does not comprise an anti-ErbB3 antibody.

In certain aspects, the present invention provides computerized methods using a computing system that comprises at least one input device configured for receiving input and at least one output device configured for rendering output, said methods being for predicting the response of cells (e.g., tumor cells) comprising a cellular network (e.g., an ErbB signaling pathway) to treatment with a therapeutic agent that targets a component within the cellular network, said methods comprising: (a) receiving, through said computing system input device, input that identifies levels of one or more components in the cellular network measured in a sample of the cells; (b) computing from the input, with the computing system, a Network Activation State (NAS) or a Network Inhibition State (NIS) for the cells using a computational model of the cellular network; and (c) generating with the computing system, and thereafter rendering at said output device, a predicted response of the cells to treatment with the therapeutic agent based at least in part on the NAS or the NIS computed in (b).

In further aspects, methods are provided for predicting the response of cells to treatment with a therapeutic agent that targets a component within a cellular network (e.g., an ErbB signaling pathway) comprised by the cells, the methods comprising: (a) measuring the level in a sample of the cells of one or more components of the cellular network; and (b) applying a computer-implemented method comprising: (i) computing a Network Activation State (NAS) or a Network Inhibition State (NIS) for the cells using a computational model of the cellular network input with the one or more measured levels; and (ii) computing and outputting a predicted response of the cells to treatment with the therapeutic agent based at least in part on the NAS or the NIS computed in (i). In certain embodiments, such methods can further comprise treating cells, or a patient from whom the cells are obtained, with a therapeutic agent, based on the predicted responsiveness of the cells to the therapeutic agent.

Also provided herein are methods for predicting the response of cells to treatment with a therapeutic agent that targets a component within a cellular network (e.g., an ErbB signaling pathway), the methods comprising: (a) measuring, in a sample of the cells, levels of one or more components of the cellular network; and (b) applying a computer-implemented method comprising: (i) computing a computational model of the cellular network by applying a statistical classification algorithm to input measured levels and computing a NAS or NIS for the cells therefrom; and (ii) predicting the response of the cells to treatment with the therapeutic agent based at least in part on the computed NAS or NIS. In certain embodiments, such methods can further comprise treating cells, or a subject from whom the cells are obtained, with a therapeutic agent, based on the predicted responsiveness of the cells to the therapeutic agent.

The present invention further provides computerized methods using a computing system that comprises at least one input device configured for receiving input and at least one output device configured for rendering output, said methods being for predicting the response of cells to treatment with a therapeutic agent that targets a component within a cellular network, such methods comprising: (a) receiving, through said computing system input device, input that identifies levels of one or more components in a cellular network measured in a sample of the cells; (b) computing with the computing system a Network Activation State (NAS) or a Network Inhibition State (NIS) for the cells using a computational model of the cellular network; (c) applying, with the computing system, a statistical classification algorithm; and (d) generating with the computing system, and thereafter rendering at said output device, a predicted response of the cells to treatment with the therapeutic agent based at least in part on output of the statistical classification algorithm.

Also provided herein are methods for predicting the response of cells to treatment with a therapeutic agent that targets a component of an ErbB signaling pathway. Certain such methods comprise: (a) measuring, in a sample of the cells, levels of (i) heregulin (HRG) and (ii) at least one receptor selected from ErbB1, ErbB2 and ErbB3; and (b) predicting, using a computer, the response of the cells to treatment with the therapeutic agent based on the levels measured in (a), wherein elevated levels of HRG and the at least one receptor, relative to a control, predict responsiveness to treatment with the therapeutic agent. Other such methods comprise (a) measuring, in a sample of the cells, levels of one or more of ErbB1/ErbB3 heterodimers, ErbB2 monomers, ErbB2/ErbB2 homodimers, phosphorylated ErbB2/ErbB2 homodimers, ErbB2/ErbB3 heterodimers, phosphorylated ErbB1/ErbB3 heterodimers and phosphorylated ErbB2/ErbB3 heterodimers, ErbB2/ErbB4 heterodimers, phosphorylated ErbB2/ErbB4 heterodimers, ErbB3/ErbB4 heterodimers, phosphorylated ErbB3/ErbB4 heterodimers; and (b) predicting, using a computer, the response of the cells to treatment with the therapeutic agent based on the levels measured in (a), wherein a difference in the level of ErbB1/ErbB3 heterodimers, ErbB2 monomers, ErbB2/ErbB2 homodimers, ErbB2/ErbB3 heterodimers, phosphorylated ErbB1/ErbB3 heterodimers or phosphorylated ErbB2/ErbB3 heterodimers, relative to a control, predicts responsiveness to treatment with the therapeutic agent. In certain embodiments, such methods can further comprise treating cells, or a subject from whom the cells are obtained, with a therapeutic agent, based on the predicted responsiveness of the cells to the therapeutic agent.

The present invention further provides computerized methods using a computing system that comprises at least one input device configured for receiving input and at least one output device configured for rendering output, said method being for predicting the response of cells to treatment with a therapeutic agent that targets a component of an ErbB signaling pathway. Certain such methods comprise: (a) receiving, through said computing system input device, input that identifies measured levels of (i) HRG and (ii) at least one receptor selected from ErbB1, ErbB2 and ErbB3, which levels have been measured in a sample of the cells; and (b) generating with the computing system, and thereafter rendering at said output device, a predicted response of the cells to treatment with the therapeutic agent based on the measured levels, wherein elevated levels of HRG and the at least one receptor, relative to a control, predict responsiveness to treatment with the therapeutic agent. Other such methods comprise: (a) receiving, through said computing system input device, input that identifies measured levels of one or more of ErbB1/ErbB3 heterodimers, ErbB2 monomers, ErbB2/ErbB2 homodimers, ErbB2/ErbB3 heterodimers, phosphorylated ErbB1/ErbB3 heterodimers and phosphorylated ErbB2/ErbB3 heterodimers, which levels have been measured in a sample of the cells; and (b) generating and rendering, with the computing system, a predicted response of the cells to treatment with the therapeutic agent based on the measured levels, wherein a difference in the level of ErbB1/ErbB3 heterodimers, ErbB2 monomers, ErbB2/ErbB2 homodimers, ErbB2/ErbB3 heterodimers, phosphorylated ErbB1/ErbB3 heterodimers or phosphorylated ErbB2/ErbB3 heterodimers, relative to a control, predicts responsiveness to treatment with the therapeutic agent.

In other aspects, kits are provided herein for predicting the response of cells to treatment with a therapeutic agent that targets a component within a cellular network, the kits comprising: (a) assays for detecting levels of one or more components of the cellular network; and (b) instructions for computing a Network Activation State (NAS) or a Network Inhibition State (NIS) for the cells using a computational model of the cellular network. In certain embodiments, such kits further comprise: (c) instructions for use of the kit to predict the response of the cells to treatment with the therapeutic agent.

The present invention further provides methods for identifying a biomarker for predicting the response of cells to treatment with a therapeutic agent that targets a component within a cellular network, the method comprising: (a) measuring, in a sample of the cells, levels of one or more components of the cellular network; and (b) applying a computer-implemented method comprising: (i) computing levels of one or more additional components of the cellular network using a computational model of the cellular network; and (ii) identifying a component of the cellular network whose computed level predicts response of the cells to treatment with a therapeutic agent to thereby identifying the component as a biomarker for predicting the response of the cells to treatment with the therapeutic agent.

Also provided herein are computerized methods using a computing system that comprises at least one input device configured for receiving input and at least one output device configured for rendering output, said methods being for identifying a biomarker for predicting the response of cells to treatment with a therapeutic agent that targets a component within a cellular network, the methods comprising: (a) receiving, through said computing system input device, input that identifies measured levels of one or more components of a cellular network measured in a sample of the cells; (b) computing, with the computing system, levels of one or more additional components of the cellular network using a computational model of the cellular network; and (c) identifying, with the computing system, a component of the cellular network whose computed level predicts response of the cells to treatment with a therapeutic agent, and thereby identifying the component as a biomarker for predicting a response of the cells to treatment with the therapeutic agent.

Within still further aspects, the present invention provides computer program products comprising one or more computer-readable storage media storing computer-executable instructions that, when executed, implement any of the foregoing methods.

BRIEF DESCRIPTION OF THE FIGURES

FIG. 1A shows the results for the MALME3M xenograft tumor model. FIG. 1B shows the results for the DU145 xenograft tumor model. FIG. 1C shows the results for the ADRr xenograft tumor model. FIG. 1D shows the results for the ACHN xenograft tumor model.

FIG. 4A shows a cartoon of the ErbB signaling pathway comprising different ligands and ErbB receptors. FIG. 4B shows a set of biochemical reactions describing the protein interactions depicted in the cartoon. FIG. 4C shows a set of fluxes derived from the set of biochemical reactions. FIG. 4D shows a set of non-linear ordinary differential equations (ODEs) based on mass action kinetics describing signal transduction networks.

FIG. 8A is a bar graph plotting simulated pErbB3 levels for the 19 cell lines, from highest to lowest pErbB3 levels. FIG. 8B is a graph ranking the 19 cell lines from highest to lowest NAS value, with cell lines having NAS values below MALME3M being ranked as nonresponders (NR), cell lines having NAS values above ADRr being ranked as responders and cell lines having NAS values between MALME3M and ADRr being ranked as indeterminate.

FIG. 9A shows the results for the IGROV1 xenograft tumor model. FIG. 9B shows the results for the OVCAR8 xenograft tumor model. FIG. 9C shows the results for the SKOV3 xenograft tumor model.

FIG. 10A plots ErbB2 versus ErbB1. FIG. 10B plots ErbB3 versus ErbB1. FIG. 10C plots ErbB2 versus ErbB3. FIG. 10D plots ErbB1 versus ErbB2 versus ErbB3.

FIG. 12A plots ErbB2 versus ErbB1. FIG. 12B plots ErbB4 versus ErbB3. FIG. 12C plots HRG-β1 versus BTC.

FIG. 13A shows a cell line standard curve for ErbB1. FIGS. 13B, 13C and 13D are bar graphs plotting the qIHC scores for ErbB1, ErbB2 and ErbB3, respectively, in the xenograft cell lines (red bars) and human tumor samples (blue bars).

FIGS. 17A and 17B show the inhibition curves for pErbB3 levels and pAKT levels, respectively, in OVCAR8 cells. FIGS. 17C and 17D show the inhibition curves for pErbB3 levels and pAKT levels, respectively, in OVCAR8 cells transfected with HER2/ErbB2 (OVCAR8-HER2 cells). The solid line represents the simulated data from the computational model, while the circles represent the experimentally determined data. The simulated $IC_{50}$ values (DR50sim) and the experimentally determined $IC_{50}$ values (DR50data) also are shown.

FIGS. 18A and 18B show the inhibition curves for pErbB3 levels and pAKT levels, respectively, in ADrR cells. The solid line represents the simulated data from the computational model, while the circles represent the experimentally determined data. The simulated $IC_{50}$ values (DR50sim) and the experimentally determined $IC_{50}$ values (DR50data) also are shown. FIGS. 18C and 18D show the simulated inhibition curves for pErbB3 levels and pAKT levels, respectively, in ADrR cells with simulated treatment with ErbB1 RNAi.

DETAILED DESCRIPTION

Figure 1:
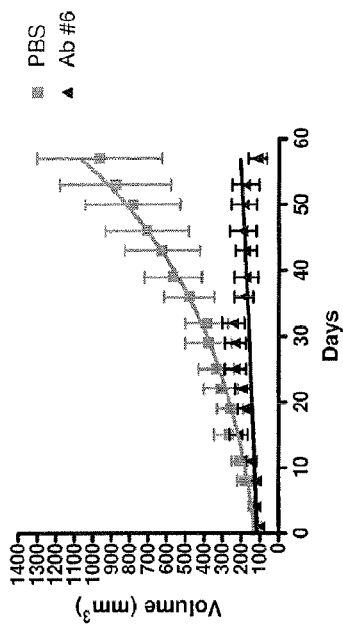
FIGS. 1A-1D are graphs showing the inhibition of xenograft tumor growth by treatment with the Ab #6 antibody.
Figure 1:
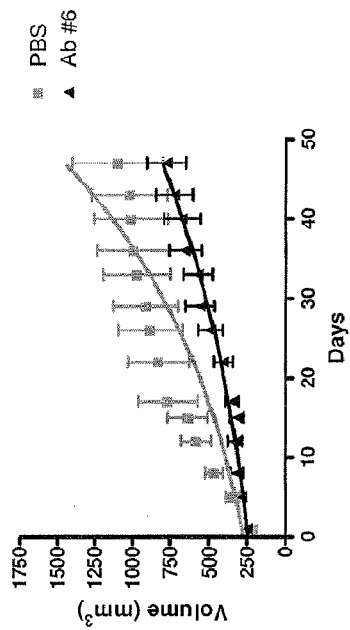
Figure 1:
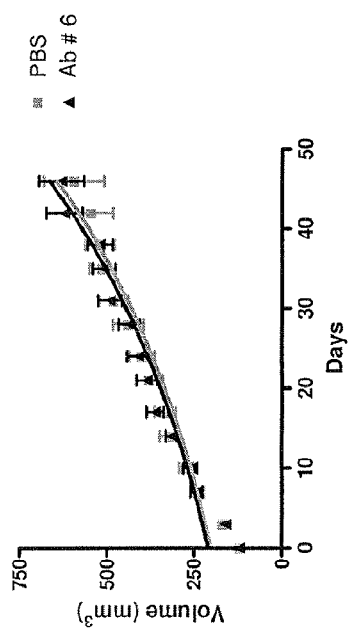
Figure 1:
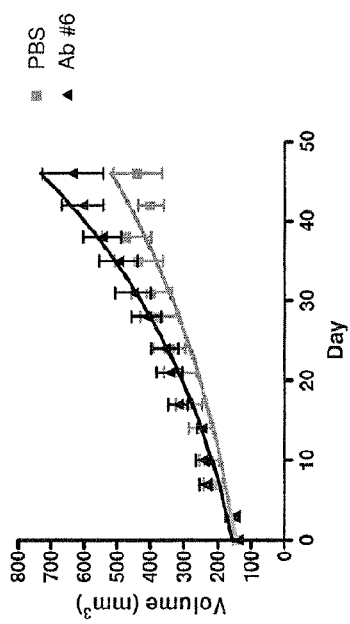

The present invention generally provides methods, systems and computer program products in which the activation state of one or more elements (e.g., ErbB3) in one or more cellular signaling pathways is determined through use of indirect markers rather than through direct measurement of levels of the one or more elements. Such indirect measurements may be used to determine the activation state of elements in a signaling pathway via computer simulation that models the signaling pathway. Using methods provided herein, this information may then be used to predict the responsiveness of cells to therapeutic agents, and thus to select a therapeutic treatment for a patient having a disease or disorder (e.g., cancer).

Through the use of the present invention, determination of a representative phosphorylation signature of a sample of tumor cells can be achieved. This allows for the use of phosphorylated cellular proteins as biomarkers for responsiveness to therapeutic agents without the need to directly measure levels of such phosphoproteins in patient samples, thus avoiding the potential problems associated with phosphoprotein measurement (e.g., instability, unreliability). Such simulation-determined phosphorylation signatures can be used to accurately predict the responsiveness of cells to anti-neoplastic therapeutic agents, and hence can be used to avoid administering cancer drugs to the patient that are ineffective to treat the patient's cancer. Furthermore, the disclosed methods allow for the simulation of the levels of other labile components within a cellular network, such as homo- and/or heterodimers of receptors, or phosphorylated homo- and/or heterodimers, within cellular networks, which components also can be used to predict the responsiveness of cells to therapeutic agents. Still further, the disclosed methods allow for the simulation of the effect of a therapeutic agent on components within a cellular network, which also can be used to predict the responsiveness of cells to the therapeutic agent.

In certain methods, the levels of one or more stable cellular components (such as cell surface receptors, ligands and the like) within a cellular network are measured in a sample of cells (e.g., cells in a tumor biopsy or resected tumor). Based on these measurements, a Network Activation State (or NAS) or a Network Inhibition State (NIS) for the cells is computed using a computational model (e.g., a mechanistic computational model) of one or more signal transduction networks. For example, the NAS can be a numeric value representing the computed level of a phosphorylated protein (that has not been directly measured) within the cellular network. Alternatively, the NIS can be a numeric value representing the computed level of a component within the cellular network in the simulated presence of the therapeutic agent (as compared to the level of the component in the simulated absence of the therapeutic agent). By comparing the computed NAS or NIS to control values representing threshold values for responsiveness or non-responsiveness, one can predict whether the cells are likely to respond to therapeutic treatment or not.

Thus, the use of "indirect" markers of cellular responsiveness to treatment is disclosed, wherein the level of that "indirect" marker (e.g., a phosphorylated protein or dimer within an activated signaling pathway) is not directly measured but rather is computed, or simulated, based on the levels of other cellular components that are directly measured. The methods also can involve the use of statistical classification algorithms, for example in combination with computation of the NAS or NIS. In the context of the present invention and as described further in the Examples section herein, a mechanistic computational model of the ErbB signaling pathway has been successfully used to compute levels of phosphorylated ErbB3 (pErbB3), as an indicator of activation of the ErbB cellular network (or NAS), and the simulated pErbB3 levels were shown to accurately predict the responsiveness of tumor cell lines to treatment with an anti-ErbB3 antibody, Ab #6, in an in vivo xenograft system. Additionally, as described further in the Examples section herein, a mechanistic computational model of the ErbB signaling pathway has been successfully used to compute relative levels of ErbB2/ErbB3 heterodimer and ErbB1/ErbB3 heterodimer in the simulated absence and presence of a therapeutic agent, as an indicator of inhibition of the ErbB cellular network (or NIS), and the simulated relative levels of ErbB2/ErbB3 and ErbB1/ErbB3 heterodimers were shown to accurately predict the responsiveness of tumor cell lines to treatment with an anti-ErbB3× anti-ErbB2 bispecific antibody, H3×B1D2, in an in vivo xenograft system.

So that the invention may be more readily understood, certain terms are first defined.

As used herein, the term "therapeutic agent" is intended to encompass any and all compounds that have an ability to decrease or inhibit the severity of the symptoms of a disease or disorder, or increase the frequency and/or duration of symptom-free or symptom-reduced periods in a disease or disorder, or inhibit or prevent impairment or disability due to a disease or disorder affliction, or inhibit or delay progression of a disease or disorder, or inhibit or delay onset of a disease or disorder, or inhibit or prevent infection in an infectious disease or disorder. Non-limiting examples of therapeutic agents include small organic molecules, monoclonal antibodies, bispecific antibodies, recombinantly engineered biologics, RNAi compounds and the like.

As used herein, a therapeutic agent that "targets a component within a cellular network" refers to an agent whose therapeutic activity results, at least in part, from the agent having a specific direct or indirect effect on the activity of a component within a cellular network. Non-limiting examples of therapeutic agents that target a component within a cellular network include the monoclonal antibody cetuximab, which specifically binds to ErbB1, thus specifically targeting ErbB1 within the ErbB cellular network, and gefitinib, a small molecule that specifically inhibits the tyrosine kinase (TK) domain of ErbB1, thus specifically targeting ErbB1-TK within the ErbB cellular network.

As used herein, the term "Network Activation State" or "NAS" refers to an indicator, typically a numeric value, that reflects, or corresponds to, the level of activation of a cellular network. A NAS typically is computed using a computational model of the cellular network. A NAS can represent, for example, the simulated level of one or more phosphorylated proteins within a cellular network. While one or more phosphoprotein levels are a preferred embodiment for the NAS (e.g., pErbB3 level as described further in Example 7 or phosphorylated ErbB homodimer or heterodimer level, such as pErbB1/ErbB3 heterodimer level as described further in Example 10, or the levels of downstream kinases such as PI3K), other cellular components within an activated signaling pathway can serve as an indicator(s) of network activation and thus can be used as the NAS, including but not limited to receptor dimerization (homodimers and heterodimers, such as levels of ErbB1/ErbB1 or ErbB2/ErbB2 homodimers or levels of ErbB1/ErbB 2, ErbB1/ErbB 3, ErbB1/ErbB 4, ErbB2/ErbB 3 or ErbB2/ErbB 4 heterodimers), protein cleavage, activation of transcription factors and activation of gene expression. The Network Activation State of a cell, e.g., a tumor cell, is an indicator of the dependence of the cell on that signaling pathway, which can be inhibited by a therapeutic agent that targets that particular signaling pathway.

As used herein, the term "Network Inhibition State" or "NIS" refers to an indicator, typically a numeric value, that reflects, or corresponds to, the level of inhibition of a cellular network. A NIS typically is computed using a computational model of the cellular network. A NIS can represent, for example, the simulated level of one or more components within a cellular network in the simulated presence of a therapeutic agent, as compared to (or relative to) the simulated level(s) in the simulated absence of the therapeutic agent. For example, the NIS can be a ratio of the level of one or more components in the simulated presence of a therapeutic agent and the level of those one or more components in the simulated absence of the therapeutic agent. A non-limiting example of a NIS is the computed relative level of one or more homo- or heterodimers (such as relative levels of ErbB2/3 and ErbB1/3 heterodimers) computed in the simulated absence and presence of a therapeutic agent (i.e., the levels in the simulated presence of the therapeutic agent as compared to the levels in the simulated absence of the therapeutic agent). However, it will be appreciated that other cellular components within a signaling pathway whose levels are modulated by a therapeutic agent also can serve as an indicator(s) of network inhibition and thus their levels can be used as indicators of the NIS. The NIS of a cell and the NAS of a cell, e.g., a tumor cell, are indicators of the impact of the therapeutic agent on components within a signaling pathway of the cell, and can be predictive of responsiveness of the cell to the effects of the therapeutic agent.

The term "computational model of a cellular network" refers to a model, such as a computer program, that translates a biological pathway diagram or cartoon (e.g., a set of protein interactions relevant to cancer) into a set of mathematical equations amenable for subsequent simulation and analysis. Certain information (e.g., ligand and/or receptor protein concentrations, rate constants) can be input into the model, which can then simulate additional information that may not be readily measurable (e.g., phosphoprotein levels). A Network Activation State (or NAS) or a Network Inhibition State (or NIS) for a cellular network can be computed using a computational model of the cellular network as described herein.

As used herein, the term "algorithm" generally refers to a set of instructions, or procedures, or formulas, for carrying out a method or solving a problem. The term "statistical classification algorithm" refers to an algorithm that defines a statistical relationship between one or more measurable parameters, or inputs, (e.g., protein levels measured in a tissue sample) and a particular outcome, or output, (e.g., responsiveness to a therapeutic agent) such that a classification, or prediction, can be made (e.g., responder versus non-responder to a therapeutic agent).

As used herein, the term "biomarker" refers to a substance (e.g., protein, mRNA, allele) within, or expressed by, a cell, wherein the biomarker correlates with the responsiveness of the disease to a given treatment.

As used herein, the term "direct biomarker" refers to a substance (e.g., protein, mRNA, allele) within, or expressed by, a cell, wherein the direct biomarker correlates with the responsiveness of the disease to a given treatment, and wherein the presence or level of that substance is directly measured in the cell to thereby predict responsiveness of the disease to a given treatment.

As used herein, the term "indirect biomarker" refers to a substance (e.g., protein, mRNA, allele) within, or expressed by, a cell, wherein the indirect biomarker correlates with the responsiveness of the disease to a given treatment, and wherein the presence or level of that substance is not directly measured in the cell, but rather is determined by indirect means, such as by simulation using a computational model, to thereby predict responsiveness of the disease to a given treatment.

An "antibody," as used herein is a protein consisting of one or more polypeptides comprising binding domains substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin structural unit comprises a tetramer that is composed of two identical pairs of polypeptide chains, each pair having one "light" (about 25 kD) and one "heavy" chain (about 50-70 kD). "$V_L$" and "$V_H$" refer to these light and heavy chains respectively.

Antibodies include intact immunoglobulins as well as antigen-binding fragments thereof, which may be produced by digestion with various peptidases, or synthesized de novo either chemically or using recombinant DNA technology. Such fragments include, for example, $F(ab)_2$ dimers and Fab monomers. Preferred antibodies include single chain antibodies (antibodies that exist as a single polypeptide chain), more preferably single chain Fv antibodies (scFv) in which a $V_H$ and a $V_L$ chain are joined together (directly or through a peptide linker) to form a continuous polypeptide. 5,132,405, and 4,956,778).

"Immunospecific" or "immunospecifically" refer to antibodies that bind via domains substantially encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds to a cognate antigen with a $K_d$ of at least 50 nM, as measured by a surface plasmon resonance assay or a cell binding assay. The use of such assays is well known in the art, and is exemplified in Example 13, herein.

An "anti-ErbB3 antibody" is an isolated antibody that immunospecifically binds to the ectodomain of ErbB3. Such binding to ErbB3 exhibits at least $K_d$ of 50 nM as measured by a surface plasmon resonance assay or a cell binding assay. Anti-ErbB3 antibodies that inhibit EGF-like ligand mediated phosphorylation of ErbB3 are preferred. EGF-like ligands include EGF, TGFα, betacellulin, heparin-binding epidermal growth factor, biregulin, epigen, epiregulin, and amphiregulin, which typically bind to ErbB1 and induce heterodimerization of ErbB1 with ErbB3.

The term "bispecific" as used herein refers to a protein comprising two antigen-binding sites, a first binding site having affinity for a first antigen or epitope and a second binding site having binding affinity for a second antigen or epitope distinct from the first.

As used herein, the term "subject" or "patient" includes any human or nonhuman animal having a disease or disorder for which response to treatment with a therapeutic agent can be predicted using the methods of the invention, such as a subject or patient with a tumor. The term "nonhuman animal" includes all vertebrates, e.g., mammals and non-mammals, such as nonhuman primates, sheep, dogs, cats, horses, cows, chickens, etc.

Many embodiments of the present invention comprise one or more computing system(s), such as special purpose and general-purpose computers including various computer hardware, such as input devices, output devices, processor(s), storage media and other corresponding computer components.

Many embodiments of the invention also include computer-readable storage media having computer-executable instructions or data structures stored thereon (including the instructions and data structures defined herein, such as the mechanistic computational models, the measured protein and biomarker levels, classification algorithms, mutation statuses, and so forth) and that are specifically configured for implementing the processes described and claimed herein. Such computer-readable storage media can be any available media that can be accessed by a general purpose or special purpose computer. By way of example, and not limitation, such computer-readable storage media can comprise RAM, ROM, EEPROM, CD-ROM or other optical disk storage, magnetic disk storage or other magnetic storage devices, or any other medium which can be used to store desired program code means, modules, and software in the form of computer-executable instructions or data structures and which can be accessed by a general purpose or special purpose computer.

In some instances, transmission media can also be used to carry the computer-executable instructions, such that the present invention also extends to applications, systems and other embodiments incorporating transmission media carrying the computer-executable instructions that are executed to perform one or more of the processes described herein. When information is transferred or provided over a network or another communications connection (either hardwired, wireless, or a combination of hardwired or wireless) to a computer, the computer properly views the connection as a computer-readable transmission medium.

The terms "computer-executable instructions", "executable instructions", "modules" and "computing modules", are sometimes used interchangeably herein to reference the computer code, data structures and software that is accessed and executed by one or more computing processors and processing components of one or more computing systems to implement certain processes of the present invention, as described within this paper and as recited in the claims.

Additional aspects regarding the foregoing and various additional aspects of this disclosure are described in further detail in the following subsections, which should not be construed as limiting.

I. Mechanistic Computational Models

Mechanistic computational models can be viewed as predictive mathematical descriptions of the molecular interactions in a protein network. In at least certain embodiments, the methods provided herein for predicting responses to therapeutic agents involve the use of a mechanistic computational model. Mechanistic computational models translate a biological pathway diagram or cartoon (e.g., a set of protein interactions occurring along a signal transduction pathway, such as a pathway relevant to cancer) into a set of mathematical equations amenable for subsequent simulation and analysis. Thus, the first step in construction of the model is generation of a detailed diagram, or cartoon, representation of the biological pathway which includes the relevant proteins and molecules involved in the pathway. Critical decisions must be made regarding which proteins and molecules are to be included, as well as the biological reactions that connect them. Information available in the scientific literature about which proteins and molecules are involved in the pathway and which biological reactions connect them is collected and used in the generation of the cartoon representation of the biological pathway.

Figure 4:
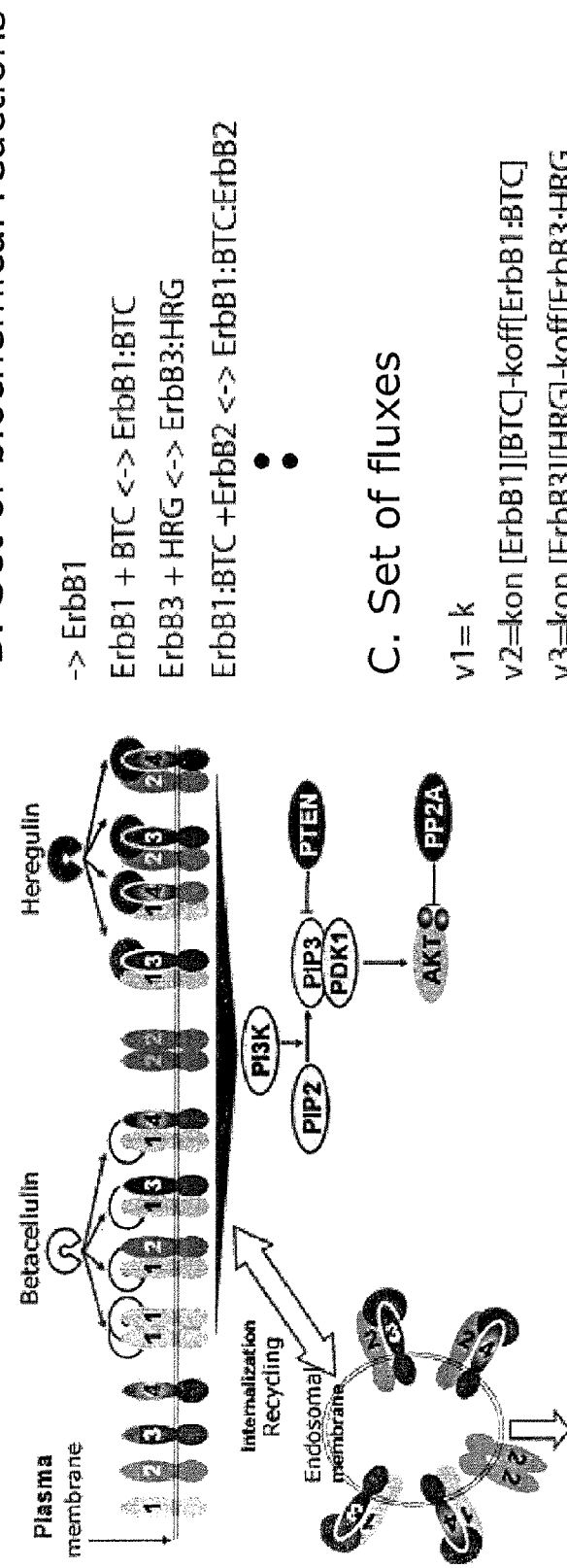
FIGS. 4A-4D show a schematic diagram of the process of converting a cartoon of a signaling pathway to a computational model.
Figure 4:
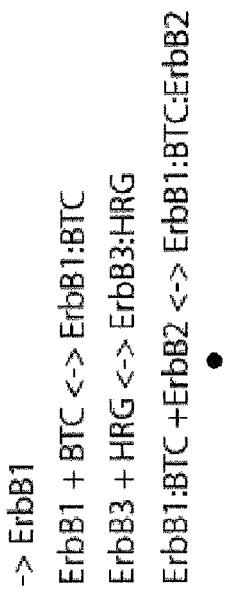
Figure 4:
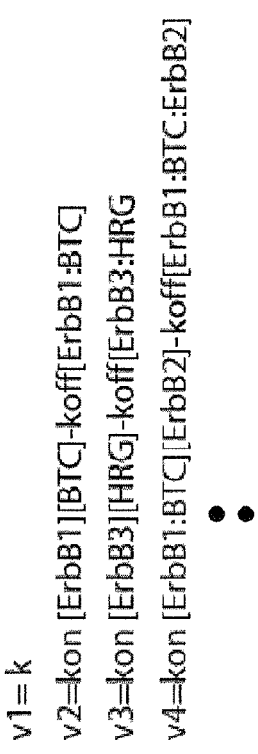

Once the cartoon representation of the biological pathway has been generated, this information is translated into a system of equations that represent the protein-protein interactions within the pathway, also referred to as a cellular network. The computational models representing the biochemical reaction networks of signal transduction networks are based on, for example, non-linear ordinary differential equations (ODEs), stochastic models, boolean or fuzzy logic models or petri nets. They are composed of differential equations that require two types of parameters that must be experimentally measured or estimated: initial species number ($c_{0,i}$ for the $i^{th}$ species) and the rate constants ($k_j$ for the $j^{th}$ rate). A schematic diagram of the process of building a computational model is shown in FIGS. 4A-D, which illustrates a cartoon diagram of the ErbB signaling pathway (FIG. 4A), translation of this pathway into sets of biochemical reaction and fluxes (FIGS. 4B and 4C) and representation of the protein-protein interactions by a set of differential equations (FIG. 4D).

The computational model typically is built as a set of executable instructions written in a computer scripting language, for example using the MATLAB software Simbiology (The MathWorks, Natick, Mass.), optionally in conjunction with The Systems Biology Toolbox 2 for MATLAB (SBtoolbox2.0rg), or JACOBIAN modeling software (Numerica Technology, Cambridge, Mass.). However, it will be appreciated that the scope of the invention also extends to the development and use of computational models, built with software and interfaces other than those built with MATLAB or JACOBIAN software and interfaces. The invention also extends to embodiments that utilize computational models that have been prebuilt by a third party source and downloaded to the computing system implementing other aspects of the invention.

Prior to model calibration, the values for as many parameters as possible are specified and input into the computing system, based on information from the scientific literature, e.g., protein levels, binding affinities, binding rate constants for ligands to their cognate receptors. Parameter values that are not available in the scientific literature can be obtained experimentally.

The model is "trained" by optimizing its output against experimentally obtained data that is input into a computing system performing the training. By fitting the model to experimental data, the optimal set of model parameters is selected. The process of model calibration involves modification of assumptions and parameter estimates. To calibrate the model, one must first identify a subset of proteins and parameters that are especially important biologically for translating a ligand stimulus into a downstream signaling event. This process is termed sensitivity analysis, which, more precisely, is a mathematical tool that measures the change in an output, such as substrate phosphorylation, in response to changes in protein concentrations and kinetic parameters within the pathway. The fully normalized sensitivity ($s_{ij}(t)$) of the $i^{th}$ observable $c_i(t)$ with respect to a change in the $j^{th}$ rate constant ($k_j$) is given by the following equation:

$$s_{ij}(t) \equiv \frac{\partial \ln(c_i(t))}{\partial \ln(k_j)}$$

Model calibration is then performed by a computing system using local and global optimization methods (such as, but not limited to, Genetic Algorithms, simulated annealing, Levenberg-Marquardt optimization, and so forth) that minimize the distance between the experimental data and the simulation results by varying the parameters and initial protein concentrations identified in the sensitivity analysis. The computing system can be configured to automatically vary the parameters during calibration or to vary the parameters only in response to incrementally added user input.

A number of computational models for various signaling pathways have been described in the scientific literature (see e.g., Kholodenko, B. N. et al. (1999) *J. Biol. Chem.* 274: 30169-30181; Schoeberl, B. et al. (2002) *Nat. Biotech.* 20: 370-375; Hayakeyama, M. et al. (2003) *Biochem. J.* 373:451-463; Nielsen, U. B. and Schoeberl, B. (2005) *IDrugs* 8:822-826; Schoeberl, B. et al. (2006) *Conf. Proc. IEEE Eng. Med. Biol. Soc.* 1:53-54; Schoeberl, B. et al. (2006) *IBM J. Res. Dev.* 50:645; Fitzgerald, J. B. et al. (2006) *Nat. Chem. Biol.* 2:458-466; Kholodenko, B. N. (2007) *Nat. Cell. Biol.* 9:324-330; Birtwistle, M. R. et al. (2007) *Molecular Systems Biology* 3:144; Hinow, P. et al. (2007) *Theoretical Biology and Medical Modelling* 4:14). Additionally, the building and use of computational models is reviewed in Kholodenko, R. N. (2006) *Nature Reviews: Mol. Cell. Biol.* 7:165-176 and Kumar, N. et al. (2006) *Drug Discovery Today* 11:806-811.

One of the computational models used in certain methods provided herein is a model of an ErbB signaling pathway. Building of a representative computational model of the ErbB signaling pathway is described in detail in Example 4. As used herein, the term "ErbB signaling pathway" is intended to encompass signal transduction pathways that initiate through interaction of a ligand with a receptor of the ErbB family. Components within an ErbB signaling pathway may include: (i) one or more ligands, examples of which include HRG, betacellulin (BTC), epidermal growth factor (EGF), heparin-binding epidermal growth factor (HB-EGF), transforming growth factor alpha (TGFα), amphiregulin (AR), epigen (EPG) and epiregulin (EPR); (ii) one or more receptors, examples of which include ErbB1, ErbB2, ErbB3 and ErbB4; and (iii) intracellular kinases, phosphatases and substrates, examples of which include phosphatidylinositol 3-kinase (PI3K), phosphatidylinositol bisphosphate (PIP2), phosphatidylinositol trisphosphate (PIP3), phosphatase and tensin homolog (PTEN), pyruvate dehydrogenase kinase isozyme 1 (PDK1), AKT, RAS, RAF, MEK, the extracellular signal-regulated kinase (ERK), protein phosphatase 2A (PP2A) and SRC protein tyrosine kinase.

Another computational model used in certain methods provided herein is a model of an IGF1R signaling pathway. As used herein, the term "IGF1R signaling pathway" is intended to encompass signal transduction pathways that initiate through interaction of a ligand with a receptor of the insulin growth factor 1 family. Components within an IGF1R signaling pathway may include: (i) one or more ligands, examples of which include insulin growth factor 1 (IGF1); (ii) one or more receptors, examples of which include IGF1R and the insulin receptor; (iii) one or more IGF binding proteins and (iv) intracellular kinases and substrates, examples of which include insulin receptor substrate 2 (IRS2), PI3K, AKT, Bc1-2 related protein BAD, RAS, RAF, MEK and mitogen-activated protein kinase (MAPK).

Yet another computational model used in certain methods provided herein is a model of a c-Met signaling pathway. As used herein, the term "c-Met signaling pathway" is intended to encompass signal transduction pathways that initiate through interaction of a ligand with a c-Met receptor protein tyrosine kinase. Components within a c-Met signaling pathway may include: (i) one or more ligands, examples of which include hepatocyte growth factor (HGF); (ii) one or more receptors, examples of which include the c-Met receptor protein tyrosine kinase; and (iii) intracellular kinases and substrates, examples of which include PI3K, growth factor receptor-bound protein 2 (GRB2), Src homologous and collagen protein (SHC), SRC protein tyrosine kinase and GAB1 scaffolding protein, as well as RAS, RAF, MEK and mitogen-activated protein kinase (MAPK).

Yet another computational model used in certain methods provided herein is a model comprising any combination of two or more growth factor signaling pathways, such as IGR1R and the ErbB receptor signaling, ErbB receptor signaling and c-Met signaling or IGF1-R, ErbB and c-Met signaling in combination.

Despite the specificity of the foregoing examples, it will be appreciated that other computational models (e.g., for signaling pathways such as TNF, IL-2, PDGF, FGF, TRAIL, integrins, cytokines and virtually any other pathway) can also be incorporated into and utilized by the embodiments of the present invention.

In certain embodiments, the presence of one or more therapeutic agents can be simulated in the computational model. A computational representation of the therapeutic agent(s) can be constructed using mass-action reaction equations that describe the binding of the agent(s) to its cellular target or otherwise describe the effect of the agent(s) on the cellular pathway being modeled. Parameters for the binding events, or other biological effects, can be obtained by direct experimental measurements, as well as by training of the model to match data for the effect of the therapeutic agent on the cell. For example, for antibody agents, the on-rate and off-rate for binding of the antibody to its target antigen can be experimentally determined by standard methods (such as BIACore or KinExA technology) and those parameters can be incorporated into the computational model. Additionally, for example, for bispecific agents, a cross-linking parameter, as a measure of the number of bispecific molecules bound to each individual target of the bispecific or to both targets of the bispecific, can be used as a training parameter for the computational model. The cross-linking parameter can be obtained by taking the overall observed binding affinity (determined by standard FACS analysis) and fitting to a standard logistic binding equation. In addition to the foregoing, additional parameters that may be pharmaceutically relevant for a particular therapeutic agent, and thus to be represented in the computational model, are known to the ordinarily skilled artisan.

When the effect of a therapeutic agent is to be represented in the computational model, a single agent can be modeled or multiple agents can be modeled in combination to thereby simulate the effect of the combination therapy on the cellular responses. For example, in one embodiment, two antibodies that each bind to different target antigens can be represented in the computational model. In another embodiment, an antibody that targets a particular signaling pathway (e.g., an ErbB pathway) and a small molecule inhibitor of that same signaling pathway (e.g., an ErbB pathway) can be simultaneously represented in the computational model to assess the effect of such combination therapy of the signaling pathway in the cell.

II. Statistical Classification Algorithms

In at least certain embodiments, the methods provided herein for predicting responses to therapeutic agents (e.g., generating predicted responses to therapeutic agents with a computer) and methods for treating patients having malignant tumors involve the use of one or more statistical classification algorithms.

One goal of a statistical model is to discern a relationship between, for example, protein levels measured in tissue samples, as well as the activation levels (e.g., the Network Activation State or "NAS") or the inhibition levels (e.g., the Network Inhibition State or "NIS") computed by the biochemical model, on the one hand, and the patient's response to a therapeutic agent on the other. Thus, a statistical classification algorithm defines a statistical relationship between one or more measurable parameters, or inputs, (e.g., protein levels measured in a tissue sample, computed NAS or NIS values) and a particular outcome, or output, (e.g., responsiveness to a therapeutic agent) such that a classification, or prediction, can be made (e.g., responder versus non-responder to a therapeutic agent). Accordingly, a statistical model helps to identify the threshold dividing responders and non-responders and also helps to define the uncertainty around the defined threshold.

Various types of statistical classifier systems have been described in the art and may be suitable for use in the methods of the invention, non-limiting examples of which include principal component analysis (PCA), partial least square regression (PLSR), trilinear PLSR, Fuzzy logic and Bayesian inference, random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. See for example PCT Publication WO 2007/109571.

To train a statistical classification algorithm, in a preferred embodiment, to use terms of the art: the "machine" or "computing system" (e.g., computer) "learns" the relationship between the protein expression level and network activation state (NAS) with the actual patient response (e.g., responder, non-responder) by examining a number of "training" examples that have been input into the computer by means of the "classifier" (statistical algorithm). This process is known as "supervised learning", since there is a collection of samples for which both the input (protein levels, measured and computed) and output (e.g., response to a therapeutic agent) are known a priori. An integral part of applying a statistical classification algorithm is the selection of informative features (a feature being any measured or computed protein level or protein activation level), as well as the determination of the optimal threshold for the score produced by the algorithm.

It is generally preferable to validate a statistical classification algorithm on a separate "test set" of samples, for which the output is known, but is not disclosed to the classifier. By comparing predictions with known results, the performance can be measured. When the number of samples is small, this may not be practicable, and there are established techniques to get around this requirement. Principal among them is cross-validation, discussed further below. The output of a classifier is a score which can be translated into a class prediction if desired. Generally, the process of training a classifier also includes methods to determine the optimal thresholds.

In order to test the ability to make predictions, the general procedure in cross-validation is to set aside a portion of the data (a fraction of the samples) as 'training data' or the 'training (data) set'; the remaining data is referred to as the 'test (data) set'. Typically, this procedure is repeated many times, each time using a different fraction of the data for training and testing. A larger training set is clearly beneficial (the more examples, the better the classifier), but so is a large test set (the more predictions you can verify, the higher your confidence in future predictions). When the sample size is small, this procedure can be amended so that a single sample is set aside as test data, and the classifier is trained using all remaining samples. A prediction is made on the single left-out sample. This is called 'leave-one-out cross-validation' (LOOCV), and is well established in the art. This procedure is repeated for each left-out sample in turn. Once all predictions have been made, performance is evaluated.

In the statistical classification algorithms used in the methods of the invention, various parameters, or informative features, or pieces of information, may be used as the input data. Non-limiting examples of such input data include protein levels of one or more components of a cellular network obtained from a cell sample, a Network Activation State (NAS) or Network Inhibition State (NIS) computed using a computational model, the mutation status of one or more proteins in the cell sample, the age of the subject for which responsiveness to treatment is being investigated and the gender of the subject for which responsiveness to treatment is being investigated.

III. Measurement of Levels of Cellular Components in a Cell Sample

In the methods provided herein for generating predicted responsiveness to treatment with a therapeutic agent and for treating a patient having a malignant tumor, one procedure typically involves measuring, in a cell sample, the levels of one or more components of a cellular network or, alternatively, inputting measured levels of one or more components of a cellular network, which have been obtained from measurements taken from a cell sample, into a computing system. For example, a sample of a tumor can be obtained by standard methods from a patient with the tumor and the levels of one or more components of a cellular network can be measured in the sample of the tumor.

Input can be manually entered into the computing system. Input can also be automatically input or downloaded to the computing system, in some instances, such as when computerized measuring devices are connected to the computing system receiving and utilizing the input to implement features of the invention. In this regard, it will also be appreciated that any measurement information and any status information (e.g., mutation status information), as well as any other tissue/patient data, described in this paper can be obtained through the use of computerized devices that automatically obtain and download the measurement and status information to one or more other computing systems that use the data to perform the described processes of the invention.

As used herein, the term "level" of a component refers to the amount or concentration of the component present in a sample. Component levels can be measured using any of a variety of well known techniques. The level typically is determined by measuring protein levels, but alternatively the level can be determined in some cases by measuring mRNA levels, which may be followed by conversion of the mRNA levels to predicted protein levels. The levels of proteins (e.g., monomers, homodimers, or heterodimers) can be measured using one or more techniques well known in the art, non-limiting examples of which include quantitative fluorescence activated cell sorting (qFACS), enzyme linked immunosorbent assay (ELISA, Luminex), immunohistochemistry (IHC), quantitative immunohistochemistry (qIHC), proximity based methods (e.g., Forster resonance energy transfer-based methods, biomolecular fluorescence complementation (BiFC), VeraTag™ or DNA-Programmed Chemistry™ (DPC™)), mass spectrometry, Western (immunoblot) assay and coimmunoprecipitation. Protein levels may be expressed as pg detected protein/μg total protein Protein or mRNA levels can be determined in cell lysates. Cell lysates can be prepared, for example, as described in detail in Example 2. Furthermore, representative examples of the use of ELISAs for determining protein levels are described in detail in Examples 2 and 4, a representative example of the use of qFACS for determining protein levels are described in detail in Example 4 and a representative example of the measurement of mRNA levels and conversion to protein levels is described in detail in Example 4 (for HRG-β1).

The tumor sample can be, for example, a fresh cell sample, a fresh frozen sample or a fixed tissue sample. For patient tissue samples, archived tissue blocks may be more easily accessible than fresh frozen samples. Thus, in a preferred embodiment, a formalin-fixed paraffin-embedded (FFPE) tissue sample is used and the level of components (e.g., ligands, receptors) can be determined by semi-quantitative immunohistochemistry (IHC) (described further in Example 9). To convert the semi-quantitative IHC information into a concentration amenable for input into a computational model, a control slide containing cell plugs or xenografts with known receptor and/or ligand expression levels can be compared to the patient sample. Moreover, conversion factors can be determined to convert an expression level obtained in dimensionless units (e.g., protein or mRNA amounts) into a concentration level that can be input into a computational model, described in further detail in Example 4 for BTC and HRG expression levels.

Ligand mRNA and ligand protein levels generally correlate reasonably well. Therefore qRT-PCR can be used to determine the mRNA expression levels in cell lysates from tumor cell lines and xenografts as well from FFPEs.

IV. Methods of Predicting Responses to Therapeutic Agents

In certain aspects, the present invention provides methods for predicting the response of cells to treatment with a therapeutic agent that targets a component within a cellular network. Such methods generally comprise the elements indicated below in Predictive Methods 1-5.

Predictive Method 1
(a) obtaining measurements of levels of one or more components of the cellular network, by measuring the level(s) present in a sample of the cells of the one or more components of the cellular network; and
(b) applying a computer-implemented method comprising:
(i) computing a Network Activation State (NAS) or a Network Inhibition State (NIS) for the cells using a computational model of the cellular network input with the measurements; and (ii) computing and outputting a predicted response of the cells to treatment with the therapeutic agent based at least in part on the NAS or the NIS computed in (i).

Predictive Method 2
(a) measuring, in a sample of the cells, levels of one or more components of the cellular network; and
(b) applying a computer-implemented method comprising:
(i) computing a Network Activation State (NAS) or a Network Inhibition State (NIS) for the cells using a computational model of the cellular network;
(ii) applying a statistical classification algorithm; and
(iii) predicting the response of the cells to treatment with the therapeutic agent based at least in part on output of the statistical classification algorithm.

Predictive Method 3
a) a computing system receiving, through an input device, input that identifies levels of one or more components in a cellular network measured in a sample of the cells;
b) the computing system computing a Network Activation State (NAS) or a Network Inhibition State (NIS) for the cells using a computational model of the cellular network; and
c) the computing system generating, and thereafter rendering at an output device, a predicted response of the cells to treatment with the therapeutic agent based at least in part on the NAS or NIS computed in b).

Predictive Method 4
a) measuring, in a sample of the cells, levels of one or more components of the cellular network;
b) computing a Network Activation State (NAS) or a Network Inhibition State (NIS) for the cells using a computational model of the cellular network;
c) applying a statistical classification algorithm; and
d) predicting the response of the cells to treatment with the therapeutic agent based at least in part on output of the statistical classification algorithm.

Predictive Method 5
a) a computing system receiving, through an input device, input that identifies levels of one or more components in a cellular network measured in a sample of the cells;
b) the computing system computing a Network Activation State (NAS) or a Network Inhibition State (NIS) for the cells using a computational model of the cellular network;
c) the computing system applying a statistical classification algorithm; and
d) the computing system generating, and thereafter rendering at an output device, a predicted response of the cells to treatment with the therapeutic agent based on output of the statistical classification algorithm.

The above methods can, but need not, further comprise treating cells, or a patient from whom the cells are obtained, with a therapeutic agent, based on the predicted responsiveness of the cells to the therapeutic agent.

In various aspects, the levels of component(s) detected serve to indicate the predicted effectiveness of one or more specific therapeutic agents. In many cases, this means that if the component(s) are detected at a level (or at a particular concentration ratio relative to other specified components) that meets a criterion of being above (or in some cases below) a pre-determined cut-off level or ratio, then a given therapeutic agent is predicted to be effective and is administered to the patient, and if the component(s) are detected at a level or concentration ratio that do not meet the criterion relative to the predetermined cut-off level or ratio, then the therapeutic agent is not administered to the patient. Appropriate cut-off levels may be set using routine practices and as described herein.

To predict the response of the cells, typically NAS or NIS values are computed for a plurality of known responder cells and non-responder cells to the therapeutic agent and these values for the known responder cells and non-responder cells are used to set threshold NAS or NIS values, indicating responsiveness or non-responsiveness to the therapeutic agent (further described in Examples 7 and 10). Thus, the generated and/or predicted response of the cells to treatment can be obtained in c) by comparing the NAS or NIS computed in b) with the threshold NAS or NIS values, indicating responsiveness or non-responsiveness to the therapeutic agent.

To apply the statistical classification algorithm, one or more pieces of information are input into the algorithm or the computing system incorporates one or more pieces of information into the algorithm. For example, this procedure can comprise inputting into the algorithm one or more pieces of information selected from (i) the levels of one or more components of the cellular network (ii) the computed NAS or NIS; (iii) the mutation status of one or more genes in the sample of the cells; (iv) the age of the subject to be treated with the therapeutic agent; (v) the gender of the subject to be treated with the therapeutic agent; (vi) presence or absence of estrogen receptor (ER) on the cells; (vii) presence or absence of progesterone receptor on the cells; and (viii) presence or absence of androgen receptor on the cells. Additionally or alternatively, applying the statistical classification algorithm can comprise the computing system computing the algorithm after inputting one or more of the pieces of information set forth in (i)-(viii) above. Since the statistical classification algorithm defines a statistical relationship between the input information and the responsiveness of the cells (e.g., tumor cells) to treatment, prediction of the response of the cells to treatment can then be based on the output of the statistical classification algorithm.

For the predictive methods and other methods provided herein, a preferred cellular network comprises an ErbB signaling pathway. In one embodiment, the one or more components measured and input into the computing system in the method can comprise one or more ligands involved in the ErbB signaling pathway. Non-limiting examples of such ligands include HRG (including HRG-$\beta$1, HRG-$\beta$2, HRG-$\alpha$, HRG-3 and HRG-4), BTC, EGF, HB-EGF, TGF$\alpha$, AR, EPG and EPR. Additionally or alternatively, the one or more components measured in the method can comprise one or more receptors involved in the ErbB signaling pathway. Non-limiting examples of such receptors include ErbB1, ErbB2, ErbB3 and ErbB4 (also known in the art as HER1, HER2, HER3 and HER4, respectively). Such receptors may be assayed as individual entities (whether they occur in monomers homodimers or heterodimers) and in certain embodiments each homodimer and heterodimer may also be measured as a distinct component and input into the computing system. For example, the components measured may be 1, 2, 3, 4, 5 or 6 or more receptors, ligands, or both, chosen from ErbB1, ErbB2, ErbB3, ErbB4, HRG, and BTC (e.g., ErbB1 and HRG; or ErbB1, ErbB2 and ErbB3). For example, in some methods, the computed NAS simulates the level of ErbB2/ErbB2 homodimer or ErbB2/ErbB3 heterodimer in the absence of the therapeutic agent. In other such methods, the computed NIS simulates the level of ErbB2/ErbB3 heterodimer or ErbB1/ErbB3 heterodimer in the presence of the therapeutic agent as compared to levels of ErbB2/ErbB3 heterodimer or ErbB1/ErbB3 heterodimer in the absence of the therapeutic agent.

In certain of the above methods, the computed NAS simulates levels of one or more phosphorylated proteins in the ErbB3 signaling pathway. For example, the NAS that is computed may simulate pErbB3 levels in the sample of the cells. In alternate embodiments, the NAS that is computed may simulate the level of a phosphorylated ErbB1/ErbB3 heterodimer or a phosphorylated ErbB2/ErbB3 heterodimer in the sample of the cells.

In one embodiment, the therapeutic agent comprises an anti-EGFR (anti-ErbB1) antibody, a representative example of which is the anti-ErbB1 antibody cetuximab (Erbitux®, ImClone Systems). Other examples of anti-ErbB1 antibodies include matuzumab, panitumumab; nimotuzumab and mAb 806 (Mishima, K. et al. (2001) *Cancer Res.* 61:5349-5354). In another embodiment, the therapeutic agent comprises an anti-ErbB2 antibody, a representative example of which is trastuzumab (Herceptin®, Genentech).

In another embodiment, the therapeutic agent comprises an anti-ErbB3 antibody. In a preferred embodiment, the anti-ErbB3 antibody comprises MM-121, which is currently undergoing Phase I clinical trials. In a preferred embodiment, the anti-ErbB3 antibody comprises Ab #6, described further in WO 2008/100624 and having $V_H$ and $V_L$ sequences of SEQ ID NOs: 1 and 2, respectively. In another embodiment, the anti-ErbB3 antibody is an antibody comprising the Ab #6 $V_H$ and $V_L$ CDR sequences of SEQ ID NOs: 7-9 ($V_H$ CDR1, 2, 3) and 10-12 ($V_L$ CDR1, 2, 3), respectively. Other examples of anti-ErbB3 antibodies include Ab #3, Ab #14, Ab #17 and Ab #19, also described further in WO 2008/100624 and having $V_H$ and $V_L$ sequences of SEQ ID NOs: 3 and 4, 5 and 6, 25 and 26, and 33 and 34, respectively. In another embodiment, the anti-ErbB3 antibody is an antibody comprising the $V_H$ and $V_L$ CDR sequences of Ab # 3 (SEQ ID NOs: 13-15 and 16-18, respectively) or antibody comprising the $V_H$ and $V_L$ CDR sequences of Ab # 14 (SEQ ID NOs: 19-21 and 22-24, respectively) or an antibody comprising the $V_H$ and $V_L$ CDR sequences of Ab # 17 (SEQ ID NOs: 27-29 and 30-32, respectively) or an antibody comprising the $V_H$ and $V_L$ CDR sequences of Ab # 19 (SEQ ID NOs: 35-37 and 38-40, respectively).

Other examples of anti-ErbB3 antibodies include the antibodies 1B4C3 and 2D1D12 (U3 Pharma AG), both of which are described in US Publication No. 2004/0197332, and the monoclonal antibodies (including humanized versions thereof), such as 8B8, described in U.S. Pat. No. 5,968,511.

In another embodiment, the anti-ErbB3 antibody is a bispecific antibody (e.g., a fusion protein) comprising an anti-ErbB3 antibody linked to a second antibody (e.g., a anti-ErbB2 antibody). A preferred example of such a bispecific antibody is H3×B1D2, the amino acid sequence of which is set forth in SEQ ID NO: 41. In this bispecific antibody, a single chain antibody that binds ErbB3, referred to as H3 (having $V_H$ and $V_L$ CDRs as shown in SEQ ID NOs: 42-44 and 45-47, respectively) is linked to a single chain antibody that binds ErbB2, referred to as B1D2 (having $V_H$ and $V_L$ CDRs as shown in SEQ ID NOs: 48-50 and 51-53, respectively). The antibody components of the bispecific antibody H3×B1D2 are described further in U.S. Pat. Nos. 7,332,585 and 7,332,580, as well as PCT Application PCT/US2006/023479 (published as WO 2007/084181) and PCT Application PCT/US2007/024287 (published as WO 2008/140493).

In yet another embodiment, the therapeutic agent comprises two or more anti-ErbB3 antibodies, each of which binds to a different epitope on ErbB3. Preferably, the therapeutic agent comprises three anti-ErbB3 antibodies, each of which binds to a different epitope on ErbB3.

In another embodiment, the therapeutic agent comprises an anti-ErbB4 antibody. In yet another embodiment, the therapeutic agent comprises a pan-ErbB inhibitor or a HER dimerization inhibitor. An example of a HER dimerization inhibitor is the antibody pertuzumab (also known as the 2C4 antibody), which is described further in Agus, D. B. et al. (2005) *J. Clin. Oncol.* 23:2534-2543.

In yet another embodiment, the therapeutic agent comprises one or more small molecule inhibitors of an ErbB signaling pathway, representative examples of which include gefitinib (Iressa®), which is commercially available from AstraZeneca and Teva, and lapatinib (Tykerb®), commercially available from GlaxoSmithKline. Other examples of small molecule inhibitors of the ErbB signaling pathway include CI-1033 (PD 183805; Pfizer), erlotinib HCL (OSI-774; Tarceva®; OSI Pharma); PKI-166 (Novartis); PD-158780; EKB-569; and Tyrphostin AG 1478 (4-(3-Chloroanillino)-6,7-dimethoxyquinazoline).

In another embodiment, the cellular network comprises a c-Met (mesenchymal epithelial transition factor) signaling pathway. In one embodiment, the one or more components measured and/or input in a) can comprise one or more ligands involved in the c-Met signaling pathway. A non-limiting example of such a ligand is hepatocyte growth factor (HGF). Additionally or alternatively, the one or more components measured in a) can comprise one or more receptors involved in the c-Met signaling pathway. A non-limiting example of such a receptor is the c-Met receptor protein tyrosine kinase.

In view of the above, the predictive methods provided herein allow for prediction of cellular responses, e.g., computer-generated prediction of tumor responses, to therapeutic agents that target components within the c-Met signaling pathway. The therapeutic agent may comprise, for example, an antibody (e.g., a monoclonal antibody) that binds to c-Met. Examples of such anti-cMet antibodies include AV299 (AVEO); AMG102 (Amgen) and 5D5 (OA-5D5; Genentech). A preferred therapeutic agent targeting the c-Met signaling pathway comprises a bispecific monoclonal antibody comprising an anti-ErbB1 antibody linked to an anti-cMet antibody. Examples of such bispecific antibodies are described further in PCT Publications WO 2005/117973 and WO 2006/091209. In another embodiment, the therapeutic agent is a small molecule inhibitor of c-Met signaling, examples of which include ARQ 197 (ArQule) and PHA665752 (Christensen, J. G. et al. (2003) *Cancer Res.* 63:7345-7355).

In another embodiment, the cellular network comprises an insulin growth factor 1 receptor (IGF1R) signaling pathway. In one embodiment, the one or more components measured in a) can comprise one or more ligands involved in the IGF1R signaling pathway. A non-limiting example of such a ligand is insulin growth factor 1 (IGF1). Additionally or alternatively, the one or more components measured in a) can comprise one or more receptors involved in the IGF1R signaling pathway. A non-limiting example of such a receptor is the IGF1R receptor.

In view of the above, the predictive methods of the invention allow for prediction of cellular responses, e.g., computer-generated prediction of tumor responses, to therapeutic agents that target components within the IGF1R signaling pathway. In a preferred embodiment, the therapeutic agent is an antibody that binds to IGF1R, examples of which include mAb391 (Hailey, L. et al. (2002) *Mol. Cancer. Ther.* 1:1349-1353); IMC-A12 (Imclone Systems, Inc.), 19D12 (Schering Plough), H7C10 (Goetsch, L. et al. (2005) *Int. J. Cancer* 113:316-328), CP751,871 (Pfizer), SCV/FC (ImmunoGen, Inc.) and EM/164 (ImmunoGen, Inc.). In a preferred embodiment, the therapeutic agent is a bispecific antibody comprising an anti-IGF1R antibody linked to an anti-ErbB3 antibody. Such bispecific antibodies are described further in PCT Publications WO 2005/117973 and WO 2006/091209. In another embodiment, the therapeutic agent is a small molecule inhibitor of IGF1R (e.g., tyrosine kinase inhibitor), examples of which include NVP-AEW541 (Novartis); NVP-ADW742 (Novartis); NVP-TAE226 (Novartis); BMS-536, 924 (Bristol-Myers Squibb); BMS-554, 417 (Bristol-Myers Squibb); cyclolignans such as picropodophyllin (PPP) (Menu, E. et al. (2006) *Blood* 107:655-660); and PQ401 (Gable, K. L. et al. (2006) *Mol. Cancer. Ther.* 5:1079-1086).

In yet another embodiment, the therapeutic agent comprises a combination of therapeutic agents, wherein the combination includes at least one agent that targets a component within the ErbB signaling pathway, such as a combination of agents that includes at least one of the ErbB pathway agents described above. For example, a combination agent can comprise two or more agents that target components within the ErbB signaling pathway. Alternatively, a combination agent can comprise at least one agent that targets a component within the ErbB signaling pathway and at least one agent that targets a component within another signaling pathway, such as a c-Met or IGF1R signaling pathway.

In various other embodiments, the cellular network comprises a combination of two or more signaling pathways, such as an ErbB signaling pathway in combination with a c-Met signaling pathway or an ErbB signaling pathway in combination with an IGF1R signaling pathway.

In another embodiment of the predictive methods provided herein, such methods can further comprise a procedure of determining, in the sample of the cells, the mutation status of one or more genes in the cells. Preferably, the mutation status of at least one gene selected from KRAS (Kirsten rat sarcoma viral oncogene homolog), PI3K and PTEN is determined. Additionally or alternatively, the method can comprise a computer system receiving, through an input device, input that identifies the mutation status of one or more genes in the cells, such as the mutation status of at least one gene selected from KRAS, PI3K and PTEN.

In another embodiment of the predictive methods, the cellular network comprises an ErbB signaling pathway and a) comprises measuring and/or inputting measured levels of BTC and AR and the method further comprises determining the mutation status, or inputting the mutation status, of the KRAS gene. In another embodiment, the cellular network comprises an ErbB signaling pathway and a) comprises measuring and/or inputting measured levels of ErbB1, ErbB2, ErbB3, HRG, BTC, AR, HB-EGF, EGF, TGFα, EPG and EPR, and the method further comprises determining the mutation status, or inputting the mutation status, of the KRAS gene. Preferably for these embodiments, the NAS computed in b) simulates levels of one or more phosphorylated proteins in the ErbB signaling pathway. In another preferred embodiment, the NAS computed in b) simulates levels of phosphorylated ErbB1/ErbB3 heterodimer in the sample of a patient's tumor. In yet another preferred embodiment, the NAS computed in b) simulates levels of phosphorylated ErbB2/ErbB3 heterodimer in the sample of a patient's tumor.

Within certain methods described above, NAS or NIS values computed for each of a plurality of known responder cells and non-responder cells to the therapeutic agent are used to set threshold NAS or NIS values, indicating responsiveness or non-responsiveness to the therapeutic agent. In other methods, the response of the cells to treatment is predicted by comparing the NAS or NIS computed in (b) with the threshold NAS or NIS values, indicating responsiveness or non-responsiveness to the therapeutic agent.

V. Biomarkers and Methods for Predicting Responses to ErbB Pathway Inhibitors In another aspect, the invention provides direct biomarkers that predict the responsiveness of cells (e.g., tumor cells) to treatment with a therapeutic agent that targets a component of a cellular network (e.g., the ErbB signaling pathway). Such biomarkers may be identified using the computational models provided herein. Methods for identifying such biomarkers generally comprise: (a) measuring, in a sample of the cells, levels of one or more components of the cellular network; and (b) applying a computer-implemented method comprising: (i) computing levels of one or more additional components of the cellular network using a computational model of the cellular network; and (ii) identifying a component of the cellular network whose computed level predicts response of the cells to treatment with a therapeutic agent to thereby identifying the component as a biomarker for predicting the response of the cells to treatment with the therapeutic agent.

Certain methods for identifying a biomarker for predicting the response of cells to treatment with a therapeutic agent that targets a component within a cellular network comprise:
a) a computing system receiving, through an input device, input that identifies measured levels of one or more components of a cellular network measured in a sample of the cells;
b) the computing system computing levels of one or more additional components of the cellular network using a computational model of the cellular network; and
c) the computing system identifying a component of the cellular network whose computed level predicts response of the cells to treatment with a therapeutic agent, and thereby identifying the component as a biomarker for predicting a response of the cells to treatment with the therapeutic agent.

For example, as illustrated in Example 10, a computational model can be used to compute levels of one or more components of a cellular network (e.g., the ErbB signaling pathway) to obtain one or more NAS values (as a measure of activation of the cellular network) and the correlation of the NAS with responsiveness of cells to treatment with a therapeutic agent can be determined. Those components of the cellular network for which the computed levels segregate samples into responders and non-responders can then also be used as direct biomarkers for predicting responsiveness to treatment, in particular when those components are readily measurable by direct means. That is, the computational model/NAS approach described herein can be used to identify (computed) component(s) that predict responsiveness of cells to treatment with a therapeutic agent and then once the component(s) have been identified, they can be directly measured as direct biomarkers for predicting responsiveness. For example, the computational model described herein was used to compute levels of homo- and heterodimers of the ErbB signaling pathway and then those dimers that segregate samples into responders and non-responders can be directly measured as direct biomarkers for predicting responsiveness to tumor treatment.

Further, as described further in Example 8, it has now been demonstrated that the combined measurement of the level of (i) HRG and (ii) at least one ErbB family receptor (e.g., ErbB1, ErbB2 and ErbB3) in a tumor sample effectively stratifies tumors into responders and non-responders with regard to responsiveness to treatment with a therapeutic agent that targets a component of an ErbB signaling pathway, such as an anti-ErbB3 antibody (e.g., Ab #6). Moreover, as described further in Example 10, levels of ErbB1/ErbB3 heterodimer or levels of phosphorylated ErbB1/ErB3 heterodimer can serve as direct markers for responsiveness to treatment with a therapeutic agent that targets a component of an ErbB signaling pathway, such as an anti-ErbB3 antibody (e.g., Ab #6). Moreover, as described further in Example 12, levels of ErbB2 monomer, ErbB2/ErbB2 homodimer and ErbB2/ErbB3 heterodimer effectively stratify tumors into responders and non-responders with regard to responsiveness to treatment with a therapeutic agent that targets a component of an ErbB signaling pathway, such as an anti-ErbB3×anti-ErbB2 bispecific antibody (e.g., H3×B1D2).

As noted above, the present invention provides methods for predicting the response of cells to treatment with a therapeutic agent that targets a component of an ErbB signaling pathway. Certain such methods comprise:
  (a) measuring, in a sample of the cells, levels of (i) HRG and (ii) at least one receptor selected from ErbB1, ErbB2 and ErbB3; and
  (b) predicting, using a computer, the response of the cells to treatment with the therapeutic agent based on the levels measured in (a), wherein elevated levels of HRG and the at least one receptor, relative to a control, predict responsiveness to treatment with the therapeutic agent.

In certain situations the levels of HRG and ErbB1 are measured. In other cases, the levels of HRG and ErbB2 are measured, or the levels of HRG and ErbB3 are measured. In other situations, the levels of HRG and at least two receptors selected from ErbB1, ErbB2 and ErbB3 are measured, or the levels of HRG, ErbB1, ErbB2 and ErbB3 are measured. In certain situations, the prediction may be computationally performed, using a method that comprises:
  (i) a computing system receiving, through an input device, input that identifies measured levels of (i) HRG and (ii) at least one receptor selected from ErbB1, ErbB2 and ErbB3, which levels have been measured in a sample of the cells; and
  (ii) the computing system generating, and thereafter rendering at an output device, a predicted response of the cells to treatment with the therapeutic agent based on the measured levels, wherein elevated levels of HRG and the at least one receptor, relative to a control, predict responsiveness to treatment with the therapeutic agent.

Preferred therapeutic agents for which responsiveness is predicted include anti-ErbB3 antibodies, more preferably Ab #6 (having $V_H$ and $V_L$ sequences as shown in SEQ ID NOs: 1 and 2, respectively) or an anti-ErbB3 antibody comprising the $V_H$ and $V_L$ CDR sequences of Ab #6, which are shown in SEQ ID NOs: 7-9 ($V_H$ CDR1, 2, 3) and 10-12 ($V_L$ CDR1, 2, 3), respectively.

Other methods for predicting the response of cells to treatment with a therapeutic agent that targets a component of an ErbB signaling pathway comprise:
  (a) measuring, in a sample of the cells, levels of one or more of ErbB1/ErbB3 heterodimer, ErbB2 monomers, ErbB2 homodimer, ErbB2/ErbB3 heterodimer, phosphorylated ErbB1/ErbB3 heterodimer and phosphorylated ErbB2/ErbB3 heterodimer; and
  (b) predicting, using a computer, the response of the cells to treatment with the therapeutic agent based on the levels measured in (a), wherein a difference in the level of ErbB1/ErbB3 heterodimer, ErbB2 monomers, ErbB2/ErbB2 homodimer, ErbB2/ErbB3 heterodimer, phosphorylated ErbB1/ErbB3 heterodimer or phosphorylated ErbB2/ErbB3 heterodimer, relative to a control, predicts responsiveness to treatment with the therapeutic agent.

The prediction may be computationally performed, using a method that comprises:
  (i) a computing system receiving, through an input device, input that identifies measured levels of one or more of ErbB1/ErbB3 heterodimer, ErbB2 monomer, ErbB2/ErbB2 homodimer, ErbB2/ErbB3 heterodimer, phosphorylated ErbB1/ErbB3 heterodimer and phosphorylated ErbB2/ErbB3 heterodimer, which levels have been measured in a sample of the cells; and
  (ii) the computing system generating, and thereafter rendering at an output device, a predicted response of the cells to treatment with the therapeutic agent based on the measured levels, wherein a difference in the level of ErbB1/ErbB3 heterodimer, ErbB2 monomer, ErbB2/ErbB2 homodimer, ErbB2/ErbB3 heterodimer, phosphorylated ErbB1/ErbB3 heterodimer or phosphorylated ErbB2/ErbB3 heterodimer, relative to a control, predicts responsiveness to treatment with the therapeutic agent.

Within certain embodiments of the above methods, the measured levels are input into a statistical classification algorithm and the response of the cells to treatment is predicted based on output of the algorithm. In further such methods, a Network Activation State (NAS) or a Network Inhibition State (NIS) is computed based on the measured levels using a computational model of an ErbB cellular network; preferably, the response of the cells to treatment with the therapeutic agent is predicted based on the computed NAS or NIS value.

Within certain embodiments, the measured levels are levels of ErbB2 monomer, ErbB2:ErbB2 homodimer and/or ErbB2:ErbB3 heterodimer and the therapeutic agent is a bispecific antibody comprising an anti-ErbB3 antibody linked to an anti-ErbB2 antibody, as described above.

Preferred cells for use in the above methods are tumor cells, including those recited above. Samples include tumor tissue, fine needle aspirate, nipple aspirate, whole blood, serum, plasma, lymph, saliva and urine or shed or circulating tumor cells isolated therefrom.

It will be apparent that, as noted above, the measured levels are protein levels (e.g., monomers, homodimers or heterodimers) or mRNA levels, and may generally be determined as described above.

Any of the above methods may, but need not, further comprise selecting a treatment regimen (e.g., for the therapeutic agent) based on the predicted response of the cells to treatment; and/or may further comprise preparing the therapeutic agent for use based on the predicted response.

In a preferred embodiment, the difference in the level, relative to a control, is an elevated level. The above methods can, but need not, further comprise treating cells, or a subject (patient) from whom the cells are obtained, with a therapeutic agent, based on the predicted responsiveness of the cells to the therapeutic agent.

For embodiments in which levels of ErbB1/ErbB3 heterodimer and/or phosphorylated ErbB1/ErbB3 heterodimer are measured, preferably the therapeutic agent for which responsiveness is predicted is an anti-ErbB3 antibody, more preferably Ab #6 (having $V_H$ and $V_L$ sequences as shown in SEQ ID NOs: 1 and 2, respectively) or an anti-ErbB3 antibody comprising the $V_H$ and $V_L$ CDR sequences of Ab #6, which are set forth in SEQ ID NOs: 7-9 ($V_H$ CDR1, 2, 3) and 10-12 ($V_L$ CDR1, 2, 3), respectively.

For embodiments in which levels of ErbB2 monomer, ErbB2/ErbB2 homodimer and/or ErbB2/ErbB3 heterodimer are measured, preferably the therapeutic agent for which responsiveness is predicted is an anti-ErbB3×anti-ErbB2 bispecific antibody, more preferably bispecific antibody H3×B1D2 (having the amino acid sequence shown in SEQ ID NO: 41) or a bispecific antibody comprising an anti-ErbB3 antibody comprising the CDRs of H3 (SEQ ID NOs: 42-44 and 45-47) linked to an anti-ErbB2 antibody comprising the CDRs of B1D2 (SEQ ID NOs: 48-50 and 51-53).

The levels of receptor homo- or heterodimers or phosphorylated receptor homo- or heterodimer can be measured in the sample of the cells using methods known in the art. For example, such homo- or heterodimers can be measured using dimerization detection methods such as those described in U.S. Pat. No. 7,105,308, U.S. Pat. No. 7,255,999, U.S. Publication No. 20040229380 and U.S. Publication No. 20080187948. These methods employ pairs of probes (e.g., antibodies), one a tagged probe and one a cleaving probe, wherein each probe binds specifically to one component of the dimer. Binding of the two probes to the dimer results in cleavage and release of the molecular tag from the dimer complex, providing a measure of formation of the dimer complex. Such assays are also referred to herein as proximity based methods, a commercially available example of which is the VeraTag™ system (Monogram Biosciences). Alternatively, other methods known in the art for quantitating dimer levels can be used, including but not limited to coimmunoprecipitation of the components within the dimer and use of other proximity based methods such as Forster resonance energy transfer-based methods and biomolecular fluorescence complementation (BiFC) (described further in, for example, Tao, R. H. and Maruyama, I. N. (2008) *J. Cell Sci.* 121:3207-3217).

In one embodiment of the above direct biomarker methods, the levels measured in a) are input into a statistical classification algorithm stored by a computing system and the response of the cells to treatment is predicted based on output of the algorithm based on calculations and transformation of the data at the computing system with use of the algorithm and measured levels. In another embodiment, a Network Activation State (NAS) or Network Inhibition State (NIS) is computed based on the levels measured in a) using a computational model of an ErbB cellular network. The response of the cells to treatment with the therapeutic agent can be predicted based at least in part on the computed NAS or NIS value.

In various embodiments, the therapeutic agent comprises any combination of one or more of an anti-ErbB3 antibody, an anti-ErbB1 antibody, an anti-ErbB2 antibody, an anti-ErbB4 antibody, a pan-ErbB inhibitor, a HER dimerization inhibitor, and a small molecule inhibitor of an ErbB signaling pathway, each of which is described and exemplified above.

VI. Uses of the Methods in Treatment

The methods of the invention can be used in predicting the efficacy of treatment for a wide variety of disorders in which therapeutic agents are available that target one or more components of a cellular network involved in the disorder. Still further, the methods of the invention can be used in the selection of a treatment regimen for a subject suffering from the disorder, wherein the methods can further comprise treating the subject according to the selected treatment regimen, which can comprise administering one or more therapeutic agents to the subject. Non-limiting examples of disorders include cancer, autoimmune disorders and inflammatory disorders.

The methods of the invention are particularly useful in predicting, e.g., computationally predicting, the response of a tumor to treatment with a therapeutic agent, i.e., predicting the responsiveness of a patient carrying the tumor to treatment with a therapeutic agent. The predictive methods can be used with any tumor that is dependent upon the signaling pathway that is modeled in the method. For example, in one embodiment, the method is used with tumors that are dependent upon the ErbB signaling pathway (e.g., the ErbB3 signaling pathway). In other embodiments, the method can be used with tumors that are dependent upon the c-Met or IGF1R signaling pathways. In a preferred embodiment, the tumor is a colon cancer tumor. In another preferred embodiment, the tumor is a non-small cell lung cancer (NSCLC) tumor. In another embodiment, the tumor is a solid tumor. In another embodiment, the tumor is a non-solid tumor, such as a clear cell sarcoma. In various other embodiments, the tumor can be, for example, a tumor of a tissue selected from lung, colon, rectum, gall bladder, brain, spinal cord, breast, kidney, pancreas, stomach, liver, bone, skin, spleen, ovary, testis, prostate, head and neck, thyroid and muscle. In yet other embodiments, the tumor is a gastric tumor, a stomach tumor or an oral/pharynx tumor.

To conduct the predictive method, a sample of cells, e.g., cells of the tumor, is obtained from the patient. For example, a preferred sample of the tumor is a sample of tumor tissue. A tumor tissue sample can be obtained by standard methods, such as biopsy of the tumor or surgical resection of the tumor. A fresh, frozen sample of tumor tissue can be used or, alternatively, a formalin-fixed, paraffin-embedded (FFPE) tissue sample is suitable for use as well. Other types of samples from the tumor also may be amenable for use in the methods, wherein the sample contains cells from the tumor and/or cellular components secreted by the tumor. Non-limiting examples of other types of samples of the tumor include fine needle aspirate, nipple aspirate, whole blood, serum, plasma, lymph, saliva and urine urine, or shed or circulating tumor cells isolated therefrom.

In a preferred embodiment, the invention provides for a method of predicting the response of a cancer patient to treatment with a therapeutic agent, wherein the method can be easily and quickly carried out by a diagnostic laboratory to provide rapid information as to the likelihood of a patient's tumor to respond to a particular therapeutic treatment. In this predictive method, a tumor sample, such as a fresh, frozen sample or a FFPE archived tissue sample is obtained from the patient and tumor receptor/ligand levels are measured via semi-quantitative immunohistochemistry (IHC). The receptor(s) and ligand(s) chosen to be measured are based on which cellular network the therapeutic agent targets (e.g., for the ErbB pathway, the following ligands/receptors can be measured: HRG, BTC, ErbB1, ErbB2 and ErbB3). The semi-quantitative IHC measurements are then converted into concentrations using a control slide, which contains cell plugs or xenografts with known receptor and ligand expression levels to compare to the patient sample. In certain situations, the mutations status of one or more genes of interest (e.g., PI3K, PTEN) may be determined in the sample using standard genotyping methods. Next, the data set (ligand and receptor concentrations, gene mutation status if determined) is input into a computational model of the cellular network of interest and a Network Activation State (NAS) is computed. Prediction of responsiveness to the therapeutic agent then can be made based on comparison of the computed NAS value to threshold NAS values for responders and non-responders. Use of a web-based application for entering the protein concentration and mutation data into the computational model, followed by output of the NAS and the predicted response, allows for a diagnostic laboratory to obtain almost instant knowledge of the likelihood of the tumor to respond to treatment with the therapeutic agent.

For any of the predictive methods of the invention described herein, after the response of the cells (e.g., tumor cells) to treatment with a therapeutic agent has been predicted using the method, the method can further comprise selecting a treatment regimen for the subject based on the predicted response of the cells (e.g., tumor cells) to treatment. For example, the methods can further comprise the computing system displaying and manually or automatically recommending and/or selecting a treatment regimen for the subject based on the computationally predicted response(s) of the cells to treatment. Still further, once a treatment regimen has been recommended or selected based on the predicted responsiveness of the cells, the methods of the invention can further comprise treating the subject according to the recommended or selected treatment regimen, which can comprise administering one or more therapeutic agents to the subject.

Also provided herein are kits for predicting the response of cells (e.g., tumor cells) to treatment with a therapeutic agent that targets a component within a cellular network. One such kit comprises: a) an assay or assays for detecting levels of one or more components of the cellular network; b) instructions for computing a Network Activation State (NAS) or Network Inhibition State (NIS) for the cells using a computational model of the cellular network; and c) instructions for use of the kit to predict the response of the cells to treatment with the therapeutic agent. In an additional embodiment, the kit can further comprise instructions for applying a statistical classification algorithm for computing the NAS or NIS.

The cellular network can be, for example, an ErbB signaling pathway, a c-Met signaling pathway or an IGF1R signaling pathway. The therapeutic agent can be, for example, any of the therapeutic agents described above that target components within any of these pathways.

In one embodiment, the means for detecting levels of one or more components of the cellular network is one or more reagents that allow for detection of protein levels of the component(s), such as one or more antibody reagents. In another embodiment, the means for detecting levels of one or more components of the cellular network is one or more reagents that allow for detection of mRNA levels of the component(s), such as one or more nucleic acid reagents (e.g., nucleic acid probes, PCR primers and the like). Such reagents for detection of protein or mRNA levels of cellular components are well known to the ordinarily skilled artisan. Such means for detecting levels can also include computing devices configured to measure protein levels.

Assays suitable for detection of protein levels of cellular components include those described herein, such as quantitative fluorescence activated cell sorting (qFACS), enzyme linked immunosorbent assay (ELISA, Luminex), immunohistochemistry (IHC), quantitative immunohistochemistry (qIHC), mass spectrometry and Western (immunoblot) assay. Assays suitable for detection of mRNA levels of cellular components include, for example, quantitative polymerase chain reaction (qPCR) and Northern blot analysis. The means for detecting levels of one or more components of the cellular network can also include, for example, buffers or other reagents for use in an assay for evaluating the levels of the component(s). The kit can include instructions, (e.g., printed instructions, such as a label or package insert) for performing the assay(s) for detecting the levels of one or more components of the cellular network.

In a preferred embodiment, the cellular network is an ErbB signaling pathway, and the kit includes means for detecting levels of one or more components (e.g., one or more of receptors, receptor homodimers, receptor heterodimers and receptor ligands) of an ErbB signaling pathway selected from ErbB1, ErbB2, ErbB3, ErbB4, HRG (including HRG-$\beta$1), BTC, EGF, HB-EGF, TGF$\alpha$, AR, EPG and EPR. More preferably, the kit includes means for detecting levels of at least one ErbB signaling pathway receptor (e.g., ErbB1, ErbB2, ErbB3, ErbB4) and at least one ErbB signaling pathway ligand (e.g., HRG, BTC, EGF, HB-EGF, TGF$\alpha$, AR, EPG and EPR). For example, in one embodiment, the kit includes means for detecting levels of ErbB1, ErbB2, ErbB3, HRG and BTC. In another embodiment, the kit includes means for detecting levels of ErbB1 and HRG. In yet another embodiment, the kit includes means for detecting ErbB1, ErbB2 and ErbB3. In still other embodiments, the kit includes means for detecting ErbB2 monomer, ErbB2 homodimer, ErbB2/ErbB3 heterodimer or ErbB1/ErbB3 heterodimer.

The means for computing a Network Activation State (NAS) or a Network Inhibition State (NIS) for the cells using a computational model of the cellular network can be, for example, a computer program product containing executable instructions that when executed cause a processor to perform operations for computing a NAS or NIS for the cells. Alternatively, the means for computing a NAS or NIS can be, for example, a component that allows the user of the kit to interface with an internet-based service that runs a computer program that can compute a NAS or NIS for the cells upon entry by the user of information on the levels of one or more components of the cellular network in the cells. Such a component can include, for example, an interface, a webpage and/or a password to allow access to the internet-based service and instructions, e.g., printed instructions, for use of the service. Computer systems and software established in the art, and described further herein, can be adapted for use in the kits of the invention. Computing devices and the computing components referenced in FIG. 16 can also include means for computing the NAS or NIS, such as computing processors, measuring and input devices, output devices, and so forth.

The instructions for use of the kit to predict the response of the cells to treatment with the therapeutic agent can include computer instructions and computer interfaces, as well as printed publications and manuals. In some instances, the kit is packaged together. In other embodiments, the various components of the kit are maintained in disparate locations. For example, some of the components can be maintained, stored or hosted on one or more remote computing systems and are only made available through a network connection.

Preferably, the kits of the invention are designed for use with a human subject, such as a human patient having a tumor. In such instances, the cells are typically cells obtained from the patient by biopsy or resection of the tumor.

VII. Therapeutic Methods and Kits

Provided are methods for treating a patient having a malignant tumor. In general, such methods comprise: obtaining a sample (e.g. a biopsy or resection sample) from a tumor from the patient; determining the level of one or more biomarkers in the sample; and administering a therapeutic agent to the patient if the levels of biomarker(s) in the sample match a predetermined profile, e.g., the level of a biomarker is greater than a minimum level. Such methods apply to any solid tumor. Suitable tumor samples are generally as described above. In certain embodiments a biomarker is an ErbB receptor protein.

In certain embodiments, such methods comprise: obtaining a sample of the tumor, assaying the level of pErbB3 in the sample, and subsequently administering at least one anti-neoplastic therapeutic agent to the patient, wherein, if the level of pErbB3 determined in the sample is no lower than a minimum level that is 25%, 50%, 60%, 70%, 80%, 90% or 100% (preferably 50%) of the level of pErbB3 assayed in a culture of ACHN cells (renal cancer cells, ATCC No. CRL-1611) following culture for about 20-24 hours in serum-free medium, then the at least one anti-neoplastic therapeutic agent subsequently administered to the patient comprises an anti-ErbB3 antibody, and if the level of pErbB3 determined in the sample is lower than the minimum level, then the at least one anti-neoplastic therapeutic agent subsequently administered to the patient does not comprise an anti-ErbB3 antibody. Preferred cultures of ACHN cells are those that have been passaged no more than 9 times, e.g., passage 8 ACHN cells. In further aspects of such embodiments, the biomarker is pErbB3, the therapeutic agent is an anti-ErbB3 antibody, and the minimum level is 40%, 50%, 60%, 70%, 80%, 90% or 100% of the level observed in tumor cells from an ACHN xenograft tumor model. In yet further aspects, the minimum level is 0.064 pg/µg total protein, 0.08 pg/µg total protein, 0.096 pg/µg total protein, 0.122 pg/µg total protein, 0.128 pg/µg total protein, 0.144 pg/µg total protein or 0.16 pg/µg total protein.

In the foregoing embodiments, the level of pErbB3 in the sample may, in certain aspects, be determined by: a) measuring levels of at least two components of the ErbB3 signaling pathway in the sample; b) computing a Network Activation State (NAS) that simulates the level of pErbB3 in the sample using the level(s) measured in (a) input into a computational model of the ErbB3 signaling pathway; and (c) determining therefrom the level of pErbB3 in the sample. In certain embodiments, levels of at least three, four, five or six components of the ErbB3 signaling pathway are detected in (a). Suitable components of the ErbB3 signaling pathway include, for example, ErbB1, ErbB2, ErbB3, ErbB4 (and homo- and hetero-dimers of the ErbB proteins), HRG (e.g., HRG-β1), BTC, EGF, HB-EGF, TGFα, AR, EPG and EPR. These components may be assayed as the protein (e.g., a monomer, a homodimer or a heterodimer), or where applicable (e.g., where total level of the protein is measured regardless of phosphorylation state, but not where a phosphoprotein level is measured, e.g., for a monomer, homodimer or heterodimer), as mRNA that encodes the protein. Appropriate assays are well known in the art, and include those described herein.

In further aspects, the method for determining the level of pErbB3 additionally comprises, applying a statistical classification algorithm to generate the computational model of the ErbB3 signaling pathway used in computing the NAS. In further embodiments, the computed NAS simulates levels of a phosphorylated ErbB1/ErbB3 heterodimer and/or a phosphorylated ErbB2/ErbB3 heterodimer in the sample.

Anti-ErbB3 antibodies for use within the present invention include, but are not limited to the anti-ErbB3 antibodies disclosed in International Patent Application No. PCT/US2008/002119, published as International Publication No. WO 2008/100624, which is incorporated herein by reference. A particularly preferred antibody therein disclosed is now known as MM-121, which is now undergoing Phase I clinical trials. Preferred anti-ErbB3 antibodies also include the anti-ErbB3 antibodies described above. Another anti-ErbB3 antibody that may be used in methods disclosed herein is U3-1287 (AMG888) (U3 Pharma AG and Amgen), which is now undergoing Phase I clinical trials.

Tumors amenable to treatment as described herein are generally as described above. Exemplary tumors are of an organ selected from colon, lung, rectum, gall bladder, brain, spinal cord, breast, kidney, pancreas, stomach, liver, bone, skin, spleen, ovary, testis, prostate and muscle. In some aspects, ErbB3 positive tumors or ErbB2 and ErbB3 positive tumors (e.g., breast tumors and non-small cell lung cancer tumors) are preferred.

The anti-neoplastic therapeutic agent may be administered to the patient in any suitable form. Typically, the therapeutic agent is provided in the form of a pharmaceutical composition, which comprises the therapeutic agent in combination with a physiologically acceptable carrier. If desired, other active or inactive ingredients may also be included within the pharmaceutical composition As used herein, the term "physiologically acceptable" means approved by a regulatory agency of a Federal or a state government (e.g., the U.S. FDA or the EMEA) or listed in the U.S. Pharmacopeia or other generally recognized pharmacopeia for use in animals, and more particularly in humans. The term "carrier" refers to a diluent, adjuvant, excipient, or vehicle with which the anti-neoplastic therapeutic agent is formulated and administered. Physiologically acceptable carriers can be sterile liquids, such as aqueous solutions, which are preferred carriers for intravenous or other parenteral administration. Saline solutions and aqueous dextrose and glycerol solutions are examples of aqueous carriers for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water and ethanol. The composition, if desired, can also contain minor amounts of wetting or emulsifying agents, pH buffering agents, or preservatives.

Pharmaceutical compositions may be formulated for any appropriate manner of administration, including, for example, parenteral, intranasal, topical, oral, or local administration, such as by a transdermal means, for prophylactic and/or therapeutic treatment. Examples of suitable pharmaceutical modes of administration and carriers are described in "Remington: The Science and Practice of Pharmacy," A. R. Gennaro, ed. Lippincott Williams & Wilkins, Philadelphia, Pa. (21$^{st}$ ed., 2005).

Commonly, the pharmaceutical compositions used in the methods provided herein are administered parenterally (e.g., by intravenous, intramuscular, or subcutaneous injection). For parenteral administration, the anti-neoplastic therapeutic agent can either be suspended or dissolved in the carrier. A sterile aqueous carrier is generally preferred, such as water, buffered water, saline or phosphate-buffered saline. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions. Pharmaceutically acceptable auxiliary substances may also be included to approximate physiological conditions, such as pH adjusting and buffering agents, tonicity adjusting agents, dispersing agents, suspending agents, wetting agents, detergents, preservatives, local anesthetics and buffering agents.

In one preferred embodiment, the pharmaceutical composition is formulated for intravenous administration to a patient (e.g., a human). Typically, compositions for intravenous administration are solutions in sterile isotonic aqueous buffer. Where necessary, the composition may also include a solubilizing agent. The ingredients may be supplied either separately or mixed together in unit dosage form, for example, as a dry lyophilized powder or water free concentrate in a hermetically sealed container such as an ampoule. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions may be sterilized by conventional sterilization techniques, or may be sterile filtered. Sterile aqueous solutions may be packaged for use as is, or lyophilized, the lyophilized preparation being combined with a sterile aqueous carrier prior to administration. The pH of an aqueous pharmaceutical composition typically will be between 3 and 11, more preferably between 5 and 9 or between 6 and 8, and most preferably between 7 and 8, such as 7 to 7.5.

The therapeutic agent is generally present within a pharmaceutical composition at a concentration such that administration of a single dose to a patient delivers a therapeutically effective amount. A therapeutically effective amount is an amount that results in a discernible patient benefit, such as a retardation or cessation of tumor growth or preferably a reduction of tumor size. Therapeutically effective amounts are affected by a variety of factors, including the activity of the anti-neoplastic therapeutic agent employed; the age, body weight, general health, sex and diet of the patient; the time and route of administration; the rate of excretion; any simultaneous treatment, such as a drug combination; and the type and severity of the tissue damage in the patient undergoing treatment. Optimal dosages may be established using routine testing, and procedures that are well known in the art. In general, compositions providing dosage levels ranging from about 1 mg to about 100 mg per kilogram of body weight per day, per week or once every 2 weeks are preferred. Non-limiting examples of suitable dosage ranges and regimens include 2-50 mg/kg (body weight of the subject) administered once a week, or twice a week or once every three days, once every two weeks, or once every three weeks, and 1-100 mg/kg administered once a week, or twice a week or once every three days, or once every two weeks. In various embodiments, a therapeutic agent is administered at a dosage of 3.2 mg/kg, 6 mg/kg, 10 mg/kg, 15 mg/kg, 20 mg/kg, 25 mg/kg, 30 mg/kg, 35 mg/kg or 40 mg/kg at a timing of once a week, or twice a week or once every three days, once every two weeks, or once every three weeks. Additional dosage ranges include: 1-1000 mg/kg, 1-500 mg/kg, 1-400 mg/kg, 1-300 mg/kg and 1-200 mg/kg. Suitable dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

Preferably, the therapeutic agent (e.g., anti ErbB3 antibody) is administered to the patient in accordance with the directions in the prescribing information provided by the manufacturer or distributor of the therapeutic agent.

Kits for use in treating patients having a malignant tumor are also provided. Certain such kits typically comprise: a) at least one assay for detecting the level of at least one component of the ErbB3 signaling pathway in a sample; and b) instructions for computing a Network Activation State (NAS) that simulates the level of pErbB3 using a computational model of the ErbB3 signaling pathway input with data obtained from the at least one assay. In certain embodiments, such kits further comprise instructions for applying a statistical classification algorithm. In certain embodiments the kit also comprises an anti-ErbB3 antibody. The assay typically comprises one or more reagents that allow for detection of at least one protein component or at least one mRNA component. In certain embodiments, the instructions for computing a NAS comprise directing the use of a computer program product containing executable instructions that when executed by a computer cause a processor to perform operations for computing a NAS; in such embodiments, the user may be instructed to run the computer program on a local computer or the user may be instructed to interface with an internet-based service that runs the computer program remotely.

Within further embodiments, kits are provided comprising anti-ErbB3 antibodies and instructions (e.g., in the form of labeling, e.g., a package insert) indicating that the anti-ErbB3 antibody is to be administered to the patient if the level of pErbB3 in a tumor biopsy from the patient exceeds a specified minimum value, and that the anti-ErbB3 antibody is not to be administered to the patient if the level of pErbB3 does not exceed the specified minimum value. For example, such instructions may indicate that the anti-ErbB3 antibody is to be administered to a patient having a malignant tumor if the level of phosphorylated ErbB3 determined in the sample is no lower than 50% of a level of phosphorylated ErbB3 measured in a culture of ACHN renal cancer cells (ATCC No. CRL-1611) following culture for about 20-24 hours in serum-free medium; and that an anti-ErbB3 antibody is not to be administered to a patient having a malignant tumor if the level of phosphorylated ErbB3 determined in the sample is lower than 50% of the level of phosphorylated ErbB3 measured in the culture of ACHN renal cancer cells.

VIII. Computing Embodiments

As mentioned above, and as should be readily apparent from the disclosure provided in this paper, many of the embodiments of the invention utilize one or more computing systems to perform the various processes described above, including, but not limited to predicting patient responses, generating recommended treatments, identifying biomarkers, computing NAS or NIS values, obtaining computational models of signal pathways, and so forth.

Figure 15A:
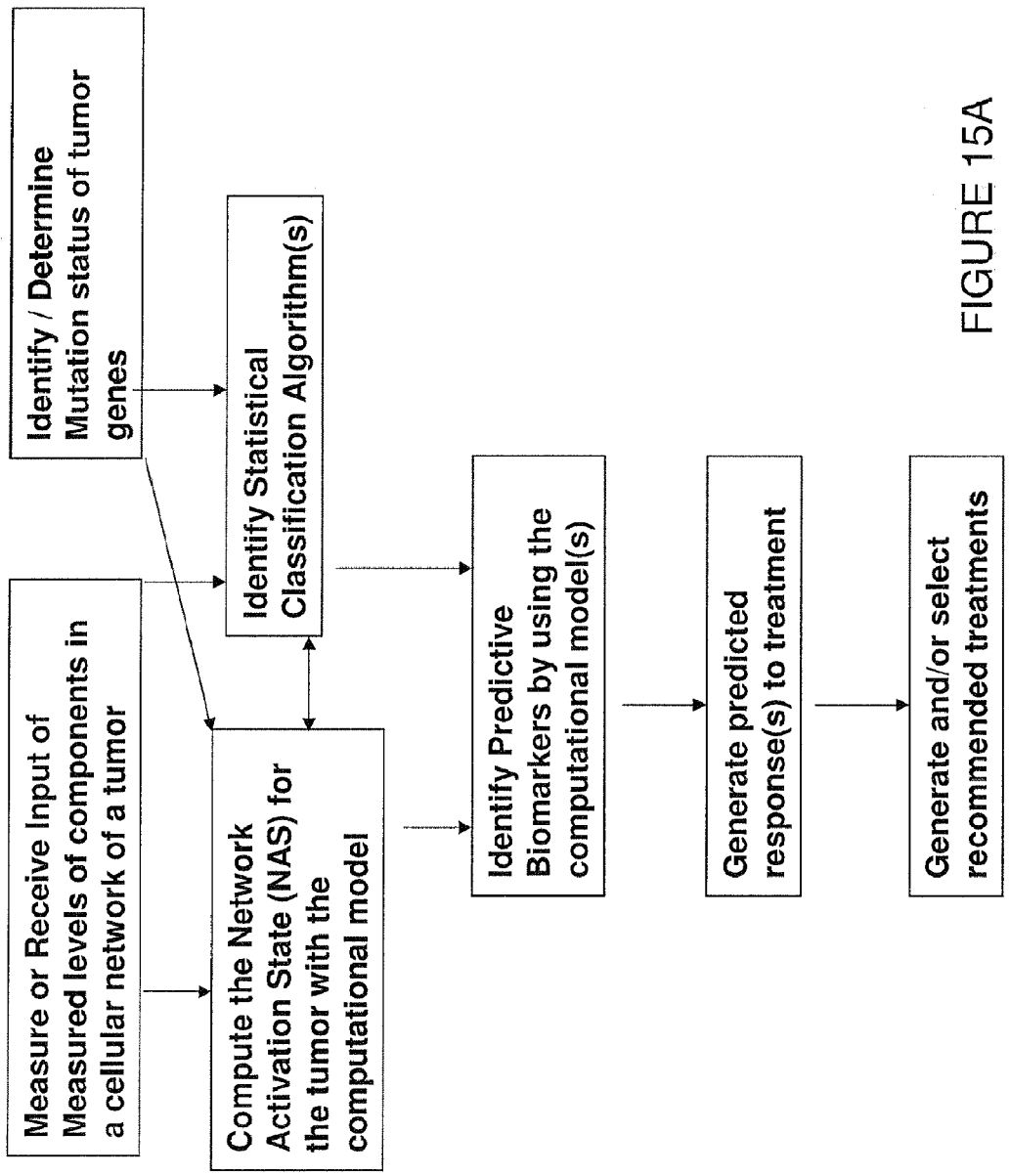
FIGS. 15A and 15B are flowcharts that include various functional steps and acts that can be performed during implementation of certain embodiments of the invention.
Figure 15B:
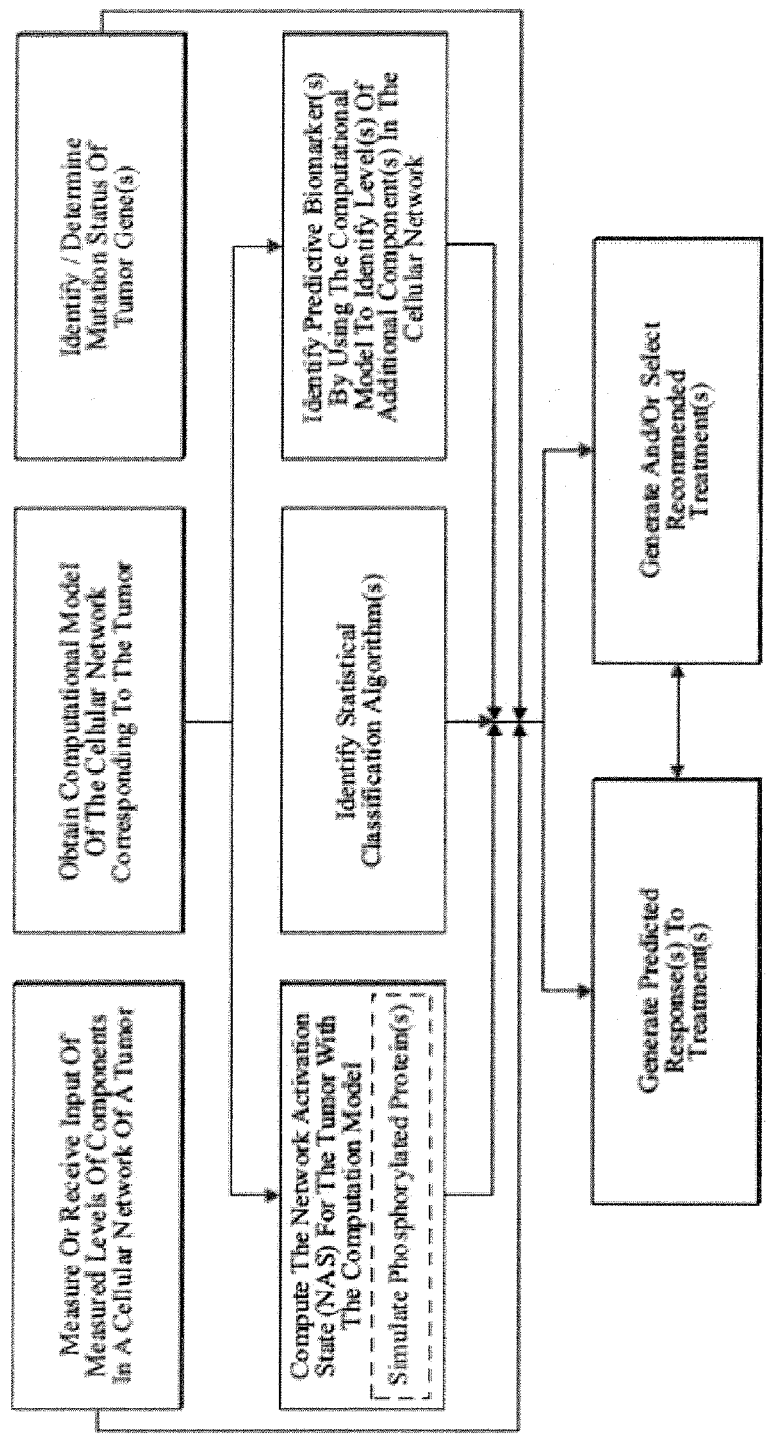

FIGS. 15A and 15B illustrate flowcharts of some of the processes that can be performed by one or more computing systems during implementation of certain embodiments of the invention. As shown, for example, computing systems can be utilized to measure and/or receive input of measured levels of components in a cellular network of a tumor as well as the mutation status of the tumor genes. Computing systems can also be used to obtain computational models, which can be obtained, for example, by receiving, downloading, building, modifying, training and/or accessing computational models from local and remote sources.

Once a computational model is obtained, one or more computing systems compute the NAS or the NIS for the cells, such as, for example, by simulating the relevant levels of phosphorylated proteins, homodimers and/or heterodimers in the cells. The computational model can also be used by the computing system to identify predictive biomarkers through the identification of additional relevant components in the cellular network based on user settings received at the computing system.

The computing system can also be used to identify statistical classification algorithms that can be received, constructed, and/or modified by the computing system as part of the identification process and that can be used in various combinations with the NAS or NIS data, other biomarker data, and patient data, to generate predicted patient responses to treatments, and/or to generate and select recommended treatments.

While the elements illustrated in the flowcharts of FIGS. 15A and 15B infer a suggested sequence or ordering for performing the computing processes of the invention, it will be appreciated that the processes illustrated in FIGS. 15A and 15B can also be performed in sequences having different ordering. For example, a recommended treatment may be identified prior to generating the computational model or computing the NAS or NIS and which may be used in the construction of the computational model. Similarly, the measurement of protein levels can occur prior to or subsequent to the generation of the computational model.

It will also be appreciated that additional processes can be performed as part of the invention, such that the invention is not limited to only methods that include the processes illustrated in the flowchart. For example, the invention can also include processes for obtaining patient information (e.g., age, gender, medical history), and for tracking actual results of recommended treatments, as well as other processes.

It should also be appreciated that the computing systems used to implement the processes of the present invention can include one or more different computing systems, of different types, as well as in different locations.

Figure 16:
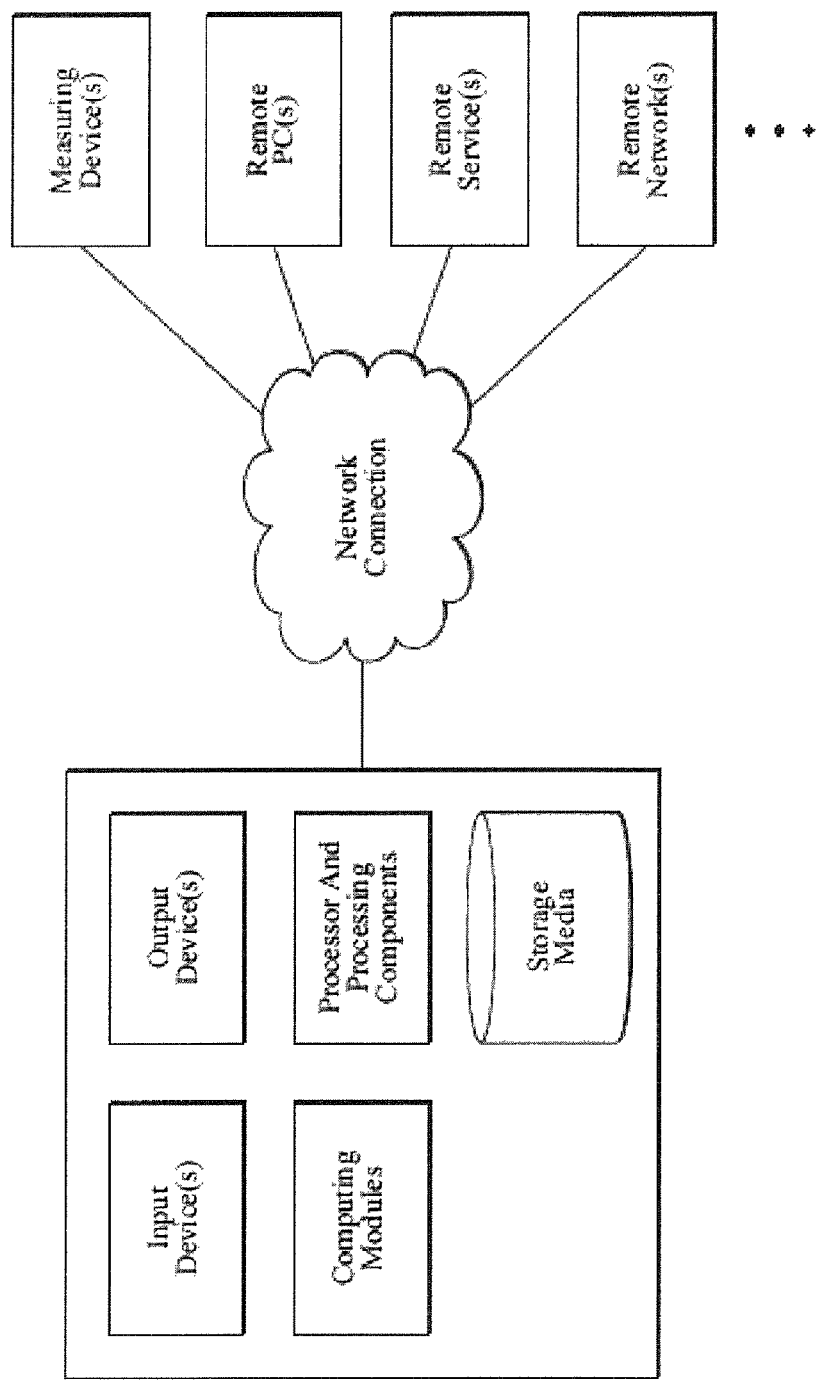
FIG. 16 is one embodiment of a computing environment that can be used to implement certain aspects of the invention.

FIG. 16 illustrates one example of a computing system that can be used to perform certain aspects of the invention (including, for example, at least some of the processes illustrated in FIGS. 15A and 15B, as well as those described throughout this paper). As illustrated, the computing system includes various input devices, output devices, computing modules, processing components and storage media. The input devices can include keyboards, mouse devices, touch pads, touch screens, microphones, as well as any other input devices. The output devices can include speakers, display screens, printing devices, switches, as well as other output devices. The computing modules include the various modules necessary to perform the functionality described in this paper, including modules for receiving and building computational models, modules for computing the NAS or NIS, modules for identifying predictive biomarkers, modules for obtaining, recognizing and storing measured levels of components and for identifying and determining mutation gene status, modules for identifying and applying statistical classification algorithms, modules for generating predicted responses to treatments, modules for generating and selecting recommended treatments, communications modules for interfacing with users and one or more other devices, as well as modules for performing the various other processes described herein.

The computing system also includes one or more processors and other processing components necessary to execute the foregoing modules, as well as storage media for storing the foregoing modules, as well as the various data structures, computational models, and other data described herein. While the storage media is illustrated as being local to the computing system, it will be appreciated that the storage media can also be located remotely from the computing system, or only partially local to the computing system. For example, in some instances, the storage media represents a distributed storage that is shared among a plurality of different computing systems and which includes storage space located in a plurality of computing systems. The storage media can also comprise any combination of persistent and volatile memory.

FIG. 16 also illustrates that the computing system is network connectable to one or more other devices, including measuring devices, remotely located computers, remote servers and remote networks. In some instances, one or more of these other devices perform one or more of the processes described in this paper, such that execution of some methods is performed in a distributed network environment involving multiple distributed computing systems and devices.

In view of the foregoing, it will be appreciated that the scope of the present invention can be implemented in various different computing configurations.

IX. EXAMPLES

The present invention is further illustrated by the following non-limiting examples. The disclosure of each and every US, International, or other patent or patent application or publication referred to herein is hereby incorporated herein by reference in its entirety.

Example 1

Xenograft Efficacy Studies with Ab #6: Training Data Set

In this example, four xenograft tumor models were used to identify tumor cell lines that responded to treatment with the anti-ErbB3 antibody Ab #6. The four xenograft tumor models studied represent different indications: MALME3M (melanoma cancer line; ATCC No. HTB-64), ADRr (ovarian cancer cell line; NCI-60, cosmic sample ID No. 905987), ACHN (renal cancer cell line; ATCC No. CRL-1611) and DU145 (prostate cancer cell line; ATCC No. HTB-81). As described in further detail below, the MALME3M and ADRr xenografts did not show a response to treatment with Ab #6, whereas the ACHN and DU145 xenografts did show a response to Ab #6 treatment.

In the xenograft tumor models, mice (nu/nu mice: 3-4 week old female mice, T-cell deficient; outbred; Albino background; from Charles River Labs, Wilmington, Mass.) are implanted in the right flank with $3.5 \times 10^6$-$3 \times 10^8$ cells/mouse (depending on cell line) in 200 µl via subcutaneous injection. Mice are monitored for initial tumor growth. Tumor cells are allowed to grow for several days until the tumor volume is approximately 200 mm$^3$. The tumor volume is calculated as $V=(\pi/6 (L \times W^2)$. The mice are treated with the Ab #6 antibody at a dosage of 600 µg/injection every 3 days (qd3). Control mice are treated with phosphate buffered saline (PBS).

Tumor volume is measured for 60-80 days. Results (obtained using the methods described above or minor variations thereof) of the effect of antibody treatment on tumor growth are summarized in the graphs shown in FIGS. 1A-1D, which demonstrate that Ab #6 treatment inhibited tumor growth in the DU145 and ACHN xenograft models, whereas Ab #6 treatment did not inhibit tumor growth (as compared to the PBS control) in the ADRr and MALME3M xenograft models.

As a measure of responsiveness of the tumor to Ab #6, the exponential growth rate is determined, which described the experimental data best. The following formula is used to describe the exponential growth.

$$V = Vo^* \exp(k^*t)$$

wherein V is the tumor volume in mm$^3$, Vo is the tumor volume at time zero, k is the exponential growth rate and t is the time in days.

In order to compare the growth reduction across different xenograft studies, a Growth Rate Reduction (GRR) value is calculated for each cell line tested, which relates the observed Growth Rate in the presence of Ab #6 to the growth rate observed in the PBS control group using the following formula:

Growth Rate Reduction=1−(Ab #6 Growth Rate $k_{Ab\,\#6}$)/(PBS Growth Rate $k_{PBS}$)

The GRR values for the four cell lines tested (obtained using the methods described above or minor variations thereof) are summarized in Table 1 below. In the case of a negative Growth Rate Reduction, the GRR value is set to zero.

TABLE 1

Summary of Tumor Growth Rate Reduction for Training Set of Xenograft Studies

| Cell Line | GRR [%] |
|---|---|
| MALME3M | 0 |
| DU145 | 72.6 |
| ADRr | 0 |
| ACHN | 28.0 |

The results demonstrate that the four xenografts show a range of responsiveness to Ab #6 treatment, with ADRr and MALME3M cells showing no response to Ab #6 treatment, ACHN having a mid-range responsiveness and DU145 cells having the highest responsiveness to Ab #6 treatment.

Example 2 pErbB3 Levels in Tumor Cell Line Lysates Correlate with Ab #6 Responsiveness in Xenografts In this example, the concentration of phosphorylated ErbB3 (pErbB3) was measured in vivo in each of the four tumor cell lines studied in Example 1, MALME3M, ADRr, DU145 and ACHN, in a short term pharmacodynamic (PD) study. The OvCAR8 xenograft also was included in this experiment (this xenograft is shown to be responsive to Ab #6 treatment in Example 5 described below).

MALME3M, ADRr, DU145, OvCAR 8 and ACHN cells are grown in culture and harvested for implantation (15×15 cm plates, ~80% confluency, total # of cells=2-4×10⁸) and kept on ice until implantation. Cells (approximately 2×10⁷ cells/mouse) are implanted into 20 mice (via subcutaneous injection, 200 µl cells/injection/mouse) into the right flank and then the mice are allowed to recover while being monitored for initial tumor growth. Tumors are measured (L×W) by digital caliper measurement. Once the mice reached a tumor volume greater than 100 mm³, they are euthanized by $CO_2$ asphyxiation and tumors from each mouse are excised and snap frozen in liquid nitrogen. Frozen tumor tissue samples are stored at −80° C. for biochemical analysis. The amount of phosphorylated ErbB3 (pErbB3) in the tumor lysates is determined by ELISA using the R&D Systems Human pErbB3 ELISA kit (Catalog #DYC1769). The sample preparation and ELISA protocols are described in further detail below.

For sample preparation and protein extraction, first the frozen tumors are pulverized and transferred to pre-weighed 2 ml VWR cryotubes (VWR International). The pulverized samples are weighed and the weights recorded. After calculating the sample weight, the appropriate amount of ice-cold lysis buffer is added to each tube to a final concentration of 62 mg/ml. The samples are briefly vortexed at low speed and incubated at 4° C. with rotation.

The crude tumor lysate is then transferred to Qiagen Qiashredder and centrifuged at 12000 rpm for 8 minutes for further homogenization of the samples. After transfer of the cleared lysates into a fresh tube, a small amount of each lysate is taken out for BCA protein assay. The rest of the lysate is aliquoted and stored at −80° C. for further ELISA assay analysis.

To quantitate total protein using a BCA Protein Assay Kit (Pierce, Catalog #23225), first a bovine serum albumin (BSA) 8 point standard curve is prepared using the 2 mg/ml BSA standard solution from the BCA kit, starting with the stock concentration of 2 mg/ml. After mixing reagents A and B from the kit (50:1) and preparing 3-fold and 5-fold dilutions of stock tumor lysate with PBS, 20 µl of BSA standard or diluted tumor lysate sample and 160 µl of working reagent are added to each well of a 96 well plate. The plate is incubated at 37° Celsius for 20 minutes. The $OD_{562}$ is read and the total amount of protein in the tumor lysates is calculated using the BSA standard curve.

To carry out the pErbB3 ELISA, different capture antibodies are diluted with PBS to the working concentration recommended by the kit (R&D Systems DYC1769). After coating black 96-well plates (Nunc Maxisorb) with diluted capture antibodies, all plates are incubated at room temperature (RT) overnight. The plates are then washed 3 times with PBST (PBS+0.05% Tween-20) on a Bio Tek plate washer and blocked for 2 hours at RT with 200 µl of 1% BSA in PBST.

Recombinant proteins for standard curves are prepared with the highest concentration recommended by the kit and 2-fold dilutions for a total of 11 points. The plates are washed 3 times with PBS and 100 µl of tumor lysates is added before incubating for 2 hour at RT. Then, plates are washed 3 times with PBST and 100 µl of primary detection antibody, diluted to the working concentration in PBS/0.1% BSA/0.05% Tween-20, is added. The plates are further incubated at RT for 2 hours. Finally, 100 µl of the mixed SuperSignal ELISA Pico Chemiluminescent Substrate (Pierce, Catalog #37069) is added to each well before reading the plates.

Figure 2:
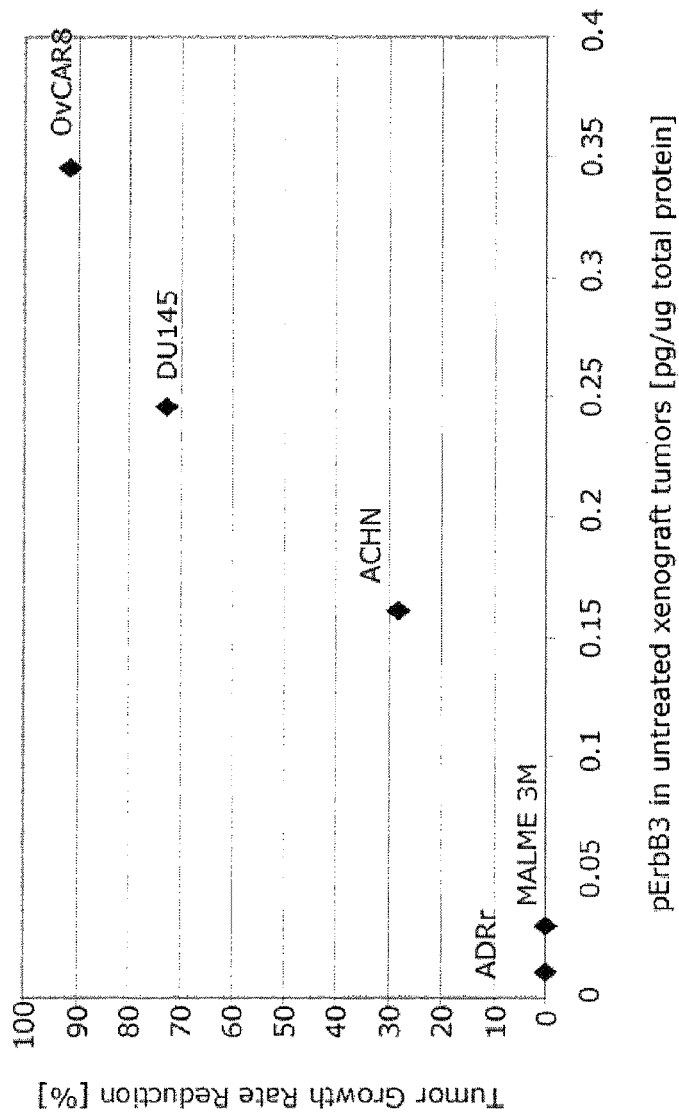
FIG. 2 is a graph plotting the concentration of phosphorylated ErbB3 (pErbB3) in untreated xenograft tumors (in pg/µg total protein) against the Growth Rate Reduction (%) observed for the xenografts when treated with Ab #6.

FIG. 2 is a graph plotting the concentration of pErbB3 in the untreated xenograft tumors (in pg/µg tumor lysate) against the Growth Rate Reduction (%—obtained using the methods described above or minor variations thereof) observed for the xenografts when treated with Ab #6. FIG. 2 demonstrates that there is a good correlation between the tumor Growth Rate Reduction and the constitutive pErbB3 levels measured in the short term pharmacodynamic studies. MALME3M and ADRr xenografts, which did not respond to Ab #6 treatment, showed the lowest levels of pErbB3, whereas ACHN, OvCAR8 and DU145 xenografts, which responded to Ab #6 treatment, had significantly higher levels of pErbB3. The results demonstrate that the pErbB3 levels in tumor cells correlate well with the responsiveness of the tumor cells to anti-ErbB3 antibody treatment.

Example 3 pErbB3 and pAKT Levels Decrease as a Function of Time to Freeze

In this example, the stability of pErbB3 and pAKT was assessed, as well as the expression levels of ErbB1, ErbB2 and ErbB3, in tumor lysates as a function of time after resurrection from freezing the tumor.

Untreated ACHN and EKVX xenograft mice are euthanized by $CO_2$ asphyxiation and tumors are dissected and cut into 4 pieces and put into liquid nitrogen at different time points: 0 min, 10 min, 30 min, and 60 min. Then, pErbB3 and pAKT levels, as well as ErbB1-3 levels, are measured in each of the samples after thawing. The results obtained using the methods described above or minor variations thereof are summarized in the bar graphs shown in FIGS. 3A-3E, with FIGS. 3A and 3B showing the levels of pErbB3 and pAKT, respectively, in the ACHN lysates and FIGS. 3C, 3D and 3E showing the levels of ErbB1, ErbB2 and ErbB3, respectively, in the EKVX lysates.

Figure 3:
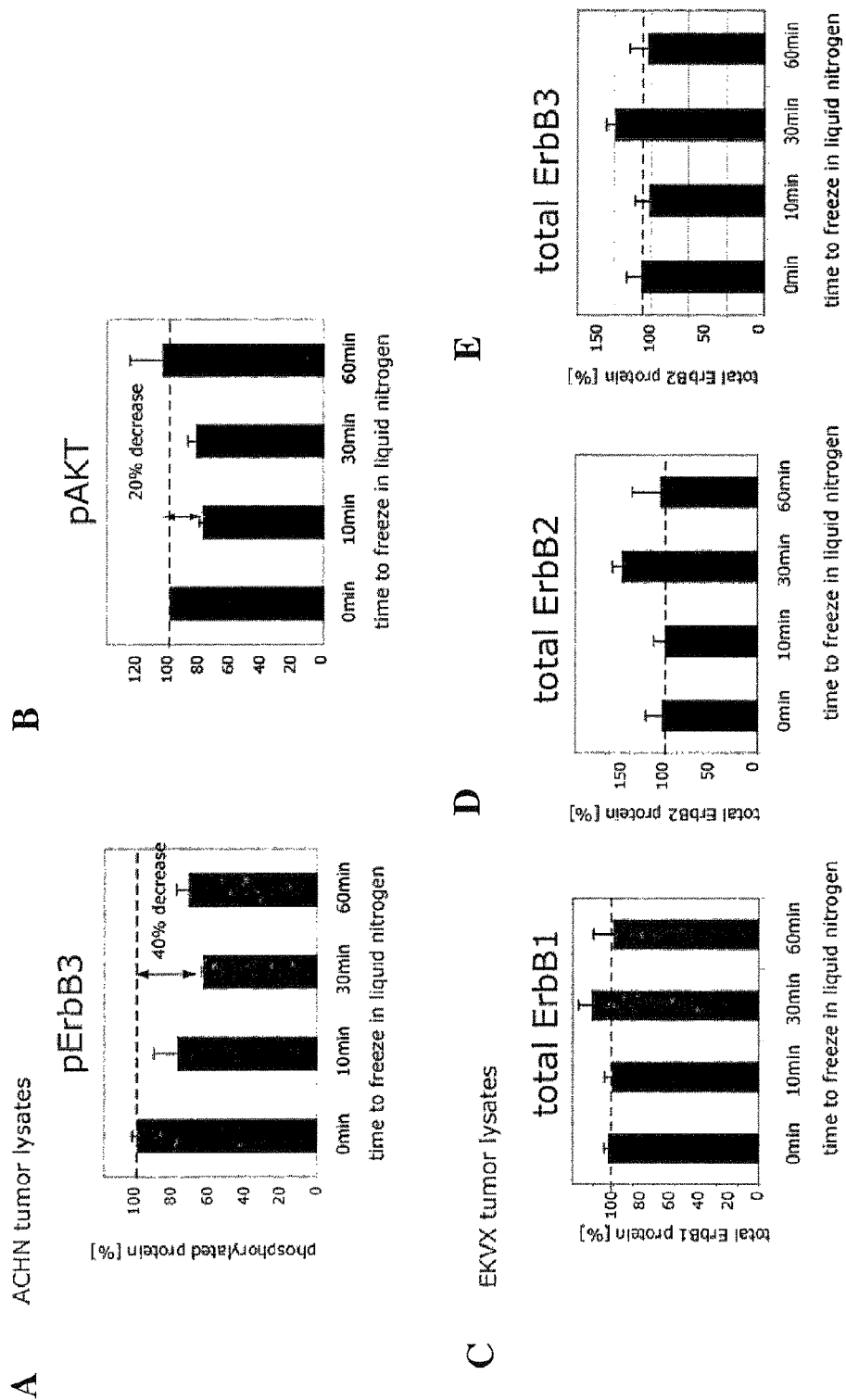
FIGS. 3A-3E are bar graphs showing the level of pErbB3 (FIG. 3A) and phosphorylated AKT (pAKT) (FIG. 3B) in ACHN xenograft tumor samples frozen 0, 10, or 60 minutes after xenograft dissection, and levels of ErbB1 (FIG. 3C), ErbB2 (FIG. 3D) and ErbB3 (FIG. 3E) in EKVX xenograft tumor samples frozen 0, 10, 30 or 60 minutes after xenograft dissection.

As shown in FIGS. 3A and 3B, in the 10 minute samples, there already was a measurable decrease in pErbB3 and pAKT levels as compared to the 0 minute samples. In the 30 minute samples, a decrease in concentration of 40% was observed for pErbB3 as compared to control (immediate snap freezing of the tumor, 0 minute sample) and a decrease in concentration of 20% was observed for pAKT as compared to control. In contrast, in EKVX and ACHN tumor cell lysates, the total levels of ErbB1-3 remained constant and appeared unaffected by the time to freeze (see FIGS. 3C-3E). Thus, the observed instability of phosphoproteins in tumor samples and the observed stability of total protein measurements demonstrate the advantage of computing the phosphorylation level of ErbB3, rather than directly measuring the level in a tumor cell lysate. This computed level of pErbB3 is referred to as the Network Activation State (NAS) in the following examples using a mechanistic computational model constructed as described below in Example 4.

Example 4

Construction and Training of a Mechanistic Computational Model of the ErbB Signaling Pathway In the following example, the building of mechanistic computational biochemical models of signal transduction pathways is described. Based on literature knowledge about ErbB signaling, a mechanistic computational model was developed comprising all the protein-protein interactions describing ligand binding to the receptor, dimerization, receptor internalization and degradation as well as the binding of the adapter molecule Gab1 leading to the activation of the PI3K cascade. A cartoon of the ErbB signaling network implemented is depicted in FIG. 4A. The computational model is a set of non-linear ordinary differential equations (ODEs) using mass action kinetics. FIG. 4B shows a set of biochemical reactions from the signaling pathway and FIG. 4C shows a set of fluxes. The biochemical reactions and fluxes are translated into a set of nonlinear ODEs, illustrated in FIG. 4D. In general, the state of change of a protein concentration ci is equal to the rate of the production of the protein $v_{production}$ minus the rate of consumption $v_{consumption}$ of the protein as represented in Equation 1.

$$\frac{dci}{dt} = \sum v_{production} - \sum v_{consumption} \quad \text{(Eqn. 1)}$$

The computational model used to predict responses to Ab #6 in the following examples consists of the mammalian ErbB network that includes all four receptors (ErbB1-4) and the Akt signal transduction cascade.

ErbB receptors are single-pass Type I transmembrane receptors with extracellular ligand binding domains, an intracellular tyrosine kinase domain and a cytoplasmic tail that acts as a signaling scaffold. ErbB1 and ErbB4 are fully functional in ligand binding and tyrosine kinase activity but ErbB2 does not bind any known ligand, functioning instead as a dimerization-ready signal amplifier (Klapper, L. N. et al. (1999) *Proc. Natl. Acad. Sci. USA* 96:4995-5000). ErbB3 has a crippled kinase domain (Guy, P. M. et al. (1994) *Proc. Natl. Acad. Sci. USA* 91:8132-8136) and therefore lacks catalytic activity, instead transducing signals when phosphorylated by other ErbB receptors. Of the 13 known ErbB ligands, BTC and HRG have been implemented as the ligands that induced the highest ErbB3 phosphorylation levels. The 13 known ErbB ligands can be divided into three groups: (i) those that bind specifically to ErbB1, such as EGF, transforming growth factor alpha (TGFα), and amphiregulin (AR), (ii) those that exhibit dual specificity, binding to both ErbB1 and ErbB4, including BTC, HB-EGF, EPG and EPR, and (iii) the neuregulins (NRGs), which fall into two subgroups: NRG1 (also known as GGF2, SMDF or HRG) which binds ErbB3/ErbB4, a property also shared with NRG2, and NRG3/NRG4 which bind ErbB4 alone. Following ligand binding, receptors dimerize and undergo transphosphorylation on residues in their cytoplasmic tails, thereby creating docking sites for SH2-containing adapter molecules such as Shc, Grb2, GAP, Sos, and PI3K. ErbB1 has at least 20 sites of tyrosine phosphorylation on its cytoplasmic tail, 12 of which have been proposed to partner with SH2-containing adapter proteins and enzymes (Schulze, W. X. et al. (2005) *Mol. Syst. Biol.* 1:2005-2008). Other ErbB receptors undergo equally complex post-translational modification. Receptor-associated adapters such as Grb2 and PI3K activate RAS, and ultimately turn on ERK and AKT. AKT can also be activated in a RAS-independent manner via the direct binding of PI3K-p85 to multiple sites on ErbB3.

Although a number of computational models have been published (see e.g., Kholodenko, B. N. et al. (1999) *J. Biol. Chem.* 274:30169-30181; Hatakeyama, M. et al. (2003) *Biochem. J.* 373:451-463; Resat, H. et al. (2003) *Biophys. J.* 85:730-743; Hendriks, B. S. et al. (2005) *J. Biol. Chem.* 280:6157-6169); Sasagawa, S. et al. (2005) *Nat. Cell. Biol.* 7:365-373; Birtwistle, M. R. et al. (2007) *Molecular Systems Biology* 3:144), the computational model used herein is more extensive and includes all four ErbB receptors and two distinct classes of ligands (HRG and BTC) while nonetheless retaining the rigor of a mass-action formulation based on elementary reactions.

Seven ErbB hetero- and homo-dimers that have been described in the literature were implemented in the model: ErbB1/1, ErbB1/2, ErbB1/3, ErbB1/4, ErbB2/2, ErbB2/3 and ErbB2/4. The majority of these dimers are activated by ligand binding but several arise through a process of "lateral signaling" (or secondary dimerization) in which dimers phosphorylated in a ligand-dependent manner dissociate into monomers that then homo- or hetero-oligomerize with either activated or unactivated monomers to create active dimers. The computational model was trained with a set experimental data that allowed for the identification of the dimers that form in the presence of HRG or BTC using the ADRr cell line.

The computational model is based on non-linear ordinary differential equations, which require two types of parameters that must be measured or estimated: initial species number and rate constants. Prior to model calibration, the values of as many parameters as possible were specified based on literature information, e.g., the binding constants for ligands to their cognate receptors. Using qFACS analysis, the expression levels of the ErbB receptors was quantified across all the cell lines used in this application. Furthermore, ELISAs were used to quantitate levels of BTC and pErbB3. Moreover, mRNA levels of HRG-β1 were determined as compared to mRNA levels in the ZR-75 cell line (ATCC No. CRL-1500). The receptor and ligand expression levels, which information is used in the computational model, are summarized in Table 2 below. The methodologies for obtaining these expression levels are described in further detail below.

Tumor cell lines are obtained from the National Cancer Institute. All cell lines are grown as monolayer cultures in a humidified atmosphere of 5% $CO_2$, 95% air and 37 degrees Celsius in complete media: RPMI-1640 media (Gibco) supplemented with 10% fetal calf serum (FCS) (Hyclone), 2 mM L-glutamine (Gibco) and units/mL Pen-Strep (Gibco).

The receptor expression levels are quantified using the Quantum Simply Cellular Kit 816A (Bangs Laboratories), which allows for quantification of receptor expression levels by qFACS. It contains a series of 4 microsphere populations labeled with varying amounts of goat anti-human IgG plus a blank population. The IgG conjugated to the beads' surface is specific for the Fc portions of the IgG antibodies. The beads are stained just like the cell samples, and with the same antibody. Each of the different populations of microspheres binds a known amount of the labeled monoclonal antibody. By plotting each population's fluorescence intensity versus its assigned Antibody Binding Capacity (ABC) value, a standard ABC curve is generated and the ABC of stained cell samples is easily determined by using the software provided by Bangs Laboratories (QuickCal v 2.3). This program takes into consideration the make of the instrument used, the voltage for that sample and the fluorochrome used.

The BTC expression levels are measured by ELISA using the R&D Systems Dy261 DuoSet-IC human Betacellulin Kit. A 384 well plate is coated with 4 µg/ml capture antibody. The 384 well plate is blocked by adding 50 µl of 2% BSA/1×PBS (no-Tween-20) for 1 hour and a recombinant standard curve is prepared. After washing the plates, 16 µl of cell lysates is added, as well as an Anti-Phospho-Tyrosine-HRP (horse radish peroxidase) detection antibody, followed by incubation for 2 hours. Finally 20 µl of Pico luminescent substrate is added and the plates are read spectrophotemetrically.

As the commercially available assays to measure HRG-β1 protein expression levels were not sufficiently sensitive to obtain reliable data for the cell lines examined, the HRG-β1 mRNA levels are quantitated for the cell lines of interest. RNA is isolated from cell lysates using RNeasy Mini protocol (74104 RNEASY KIT from QUIAGEN). After converting isolated RNA to cDNA and making a master mix for quantitative PCR (QPCR) using the Applied Biosystems 430443 7 Taqman Master mix, QPCR is run and quantified the HRG-β1 mRNA expression relative to the mRNA levels in ZR75-1 cells. Primers for QPCR are purchased from Applied Biosystems.

The ErbB3 phosphorylation levels for the different cell lines shown in Table 2 are determined using the pErbB3 ELISA kit from R&D (Dyc1769-2 DuoSet-IC human phospho-ErbB3), using the methods described above in Example 2 or minor variations thereof.

Table 2 below summarizes the receptor and ligand expression level information obtained for the different cell lines using the methods described above or minor variations thereof, which information was used in the construction of the computational model of the ErbB signaling pathway. Column 1 shows the name of the cell line; column 2 shows the type of tumor; columns 3-5 show the number of receptors per cell for ErbB1, ErbB2 and ErbB3, respectively; column 6 shows the HRG-β1 mRNA levels, expressed as the fold compared to the mRNA levels in ZR-75 cells; and columns 7 and 8 show the amount of BTC and pErbB3 present in the cells, expressed as pg/cell.

TABLE 2

Summary of Receptor and Ligand Expression Levels for the Cell Lines Used in Xenograft Experiments

| cell line | tumor type | ErbB1 #/cell | ErbB2 #/cell | ErbB3 #/cell | HRG b-1 fold compared to ZR-75 | BTC pg/cell | pErbB3 pg/cell |
|---|---|---|---|---|---|---|---|
| ACHN | renal | 448283.5 | 45455.75 | 15200 | 2544.794306 | 3.34191E-05 | 4.15E-05 |
| ADRr | mammary | 177817.5 | 40792 | 33204.5 | 226 | 1.14529E-08 | 1.80E-05 |
| DU145 | prostate | 437841.25 | 69068 | 19422 | 2.219138944 | 9.87522E-06 | 1.50E-04 |
| IGROV1 | ovarian | 149031.25 | 158417.5 | 5355.25 | 0 | 2.61392E-06 | ND |
| MALME3M | melanoma | 2914.2 | 56422 | 67367 | 0.438302861 | 6.71181E-08 | 7.90E-06 |
| OVCAR8 | ovarian | 236156.75 | 53272.25 | 31812.75 | 343.3017338 | 5.88861E-07 | ND |
| SKOV3 | ovarian | 264132 | 1377660.5 | 13693.5 | 340 | 1.63191E-05 | ND |

For training of the computational model, a data set was used that comprises dose-time matrices in which phosphorylation of ErbB1, ErbB2, ErbB3 and AKT at multiple time points and at nine different concentrations of BTC or HRG stimulation in ADRr cells are measured by ELISA. For stimulation of the cells, the cells are seeded in 100 µl complete media at 35,000 cells per well in 96 well tissue culture plates and incubated overnight in a humidified atmosphere of 5% $CO_2$, 95% air and 37 degrees Celsius. Cells are then switched to serum free media: RPMI-1640 media (Gibco) supplemented with, 2 mM L-glutamine (Gibco) and units/mL Pen-Strep (Gibco). Starved cells are incubated in a humidified atmosphere of 5% $CO_2$, 95% air and 37 degrees Celsius for 20-24 hours prior to stimulation. For dose-time matrix studies, cells are stimulated with ligand (BTC or HRG) at 0, 1, 2, 3, 4, 5, 7, 10, 20, 30, 60 and 120 minutes. Following stimulation with 9 different concentrations of HRG (0.038 nM-250 nM) and BTC (0-700 nM) for each time course, cells are placed on ice, washed with cold PBS, then lysed in 30 µl cold M-PER Mammalian Protein Extraction Buffer (Thermo Scientific, Catalog #78501) supplemented with protease inhibitor cocktail (Sigma-Aldrich, P2714), 1 mM sodium orthovanadate (Sigma-Aldrich, S6508), 5 mM sodium pyrophosphate (Sigma-Aldrich, 221368), 50 µM oxophenylarsine (EMD Biosciences, 521000) and 10 µM bpV(phen) (EMD Biosciences, 203695).

Levels of protein phosphorylation in the stimulated cells are measured by ELISA. Capture antibodies against ErbB1 (R&D Systems, AF231), ErbB2 (R&D Systems, MAB1129), ErbB3 (R&D Systems, MAB3481) and AKT (Upstate, 05-591MG) are incubated in 384 well black flat-bottom polystyrene high-binding plates (Corning, Catalog #3708) overnight at room temperature. The ELISA plates are blocked with 2% bovine serum albumin (BSA) and phosphate buffered saline (PBS) for one hour then incubated with lysates diluted in 2% BSA, 0.1% Tween-20 and PBS for two hours at room temp. In between each incubation, the plates are washed three times with 0.05% Tween-20 in PBS. ELISAs for measuring phospho-ErbB1, -ErbB2 and -ErbB3 are incubated with phospho-tyrosine horseradish peroxidase (HRP) linked monoclonal antibody (R&D Systems, HAM1676) for two hours. ELISAs measuring phospho-AKT are incubated with primary serine 473 specific anti-phospho AKT mouse monoclonal antibody (Cell Signaling Technologies, Catalog #5102) for 2 hours, then incubated with Streptavidin-HRP (R&D Systems, Catalog #DY998,) for 30 minutes. All ELISAs are visualized with SuperSignal ELISA Pico Chemiluminescent Substrate (Pierce, Catalog #37069) and luminescent signal is measured using a luminometer.

Figure 5:
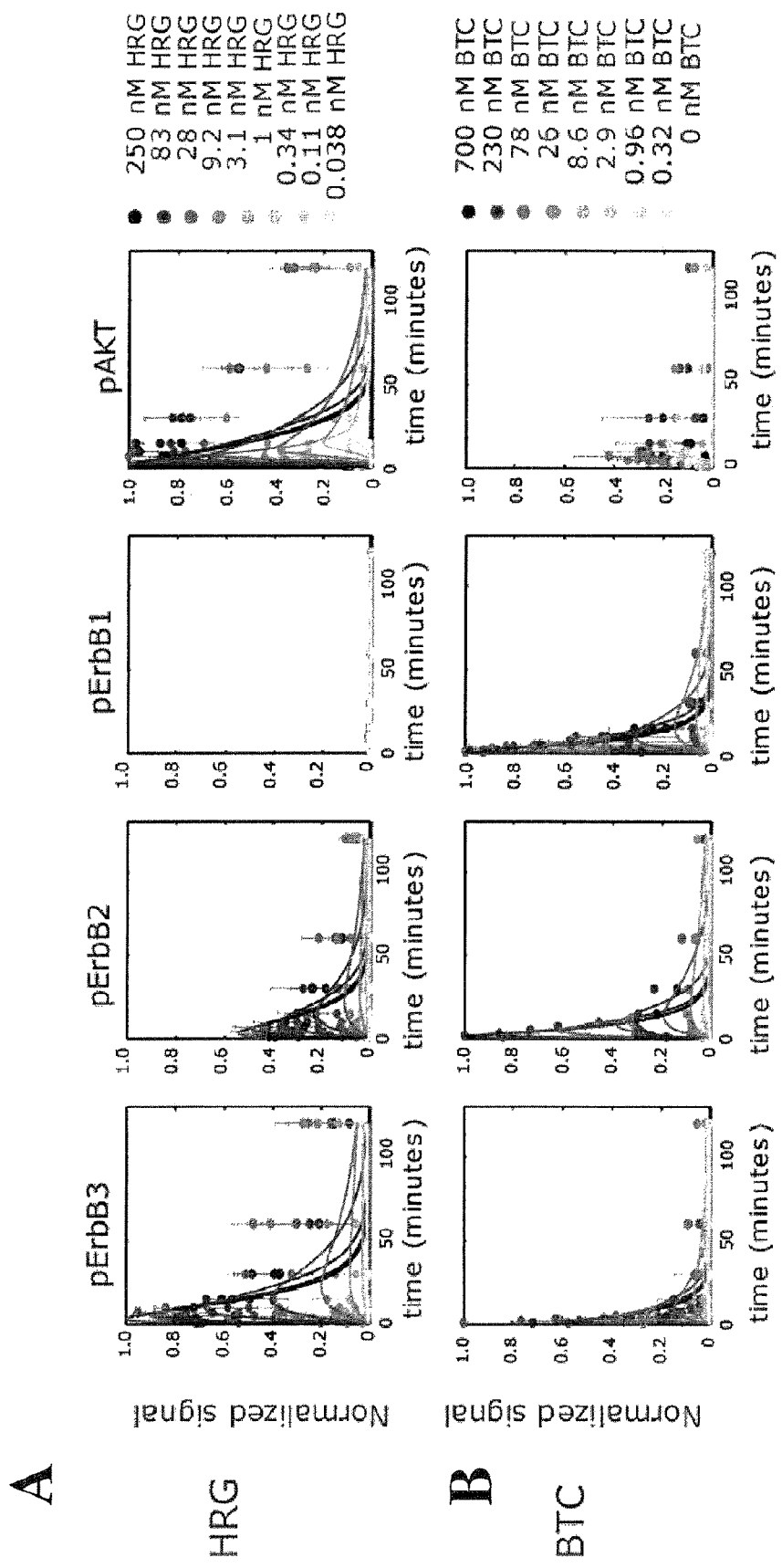
FIGS. 5A-5B are graphs showing the levels of phospho-ErbB3, phospho-ErbB2, phospho-ErbB1 and phospho-AKT over time in cells stimulated with nine different concentrations of heregulin (HRG) (FIG. 5A) or betacellulin (FIG. 5B) in ADRr ovarian cancer cells. The parameters of the computational model were calibrated for the simulation results (solid lines) to describe the experimental data (dots).

Results (obtained using the methods described above or minor variations thereof) for the data set of the protein phosphorylation at multiple time points and nine different concentrations of BTC or HRG are shown in FIGS. 5A-5B, wherein FIG. 5A shows the levels of phopho-ErbB3, phospho-ErbB2, phospho-ErbB3 and phospho-AKT for HRG-stimulated cells and FIG. 5B shows the levels of phopho-ErbB3, phospho-ErbB2, phospho-ErbB3 and phospho-AKT for BTC-stimulated cells. This data set was used to calibrate the computational model of the ErbB signaling pathway so that the simulation results (lines) describe the experimental data (dots) shown in FIGS. 5A-5B.

Further information on the development of a computational model of the ErbB receptor signaling network is provided below:

Model Structure

The ErbB receptor signaling network model consists of three receptors (ErbB1, ErbB2, ErbB3), a receptor phosphatase, phosphatidylinositol 3-kinase (PI3K, which binds the receptors) and components of the PI3K-AKT cascade (phosphatidylinositol bisphosphate, PIP2, phosphoinositide-dependent protein kinase, PDK1, PTEN deleted from chromosome 10, PTEN, serine, threonine protein kinase also known as protein kinase B, AKT, Protein phosphatase 2A, PP2A) (see Table 8 below). Two ErbB receptor ligands were included: heregulin (HRG1-β), which binds to ErbB3 and ErbB4 (not included in model because experimentally ErbB4 expression levels were very difficult to detect in cell lines (see Table 3 below) and Betacellulin (BTC), which binds primarily to ErbB1 (Beerli, R. R. and Hynes, N. E. (1996) *J. Biol. Chem.* 271:6071-6076; Jones, J. T. et al. (1999) *FEBS Lett.* 447:227-231). The mass-action kinetic reactions, listed in full in Table 11 below, were converted to ordinary differential equations using Matlab Simbiology 2.3 (Mathworks, Mass.).

Included in the model were the ligand-induced dimerization, internalization, recycling, and degradation as described in the literature for all homo- and heterodimers (Hendriks, B. S. et al. (2003) *J. Biol. Chem.* 278:23343-23351; Wang, Z. et al. (1999) *Mol. Biol. Cell* 10:1621-1636). Receptor dimer stabilities, using the relative scale as published in Shankaran, H. et al. (2008) *Biochem. Biophys. Res. Commun.* 371:220-224, were implemented, where the coexpression of ErbB1 with ErbB2 or ErbB3 biases signaling to the cell surface and retards signal downregulation and where the simultaneous coexpression of ErbB1-3 leads to an abundance of ErbB2-ErbB3 heterodimers. Therefore, ErbB3-containing dimers internalize and degrade slower than do ErbB1 homodimers or ErbB1-ErbB2 heterodimers. Constitutive dimerization was also included, although ligand-free dimers were assumed not to trigger any downstream signaling (Yu, X. et al. (2002) *Mol. Biol. Cell* 13:2547-2557) and to remain at the cell surface. ErbB ligands bind with different affinities to ErbB homo- and heterodimers (Teramura, Y. et al. (2006) *EMBO J.* 25:4215-4222), but to reduce the number of kinetic parameters to be estimated and to describe the experimental data with the simplest model possible, we constrained the binding affinity of the ligands to ErbB homo- and heterodimers to be the same.

Dimerized receptors undergo rapid phosphorylation and activate downstream pathways through binding of signaling adaptors to phosphotyrosine sites on the receptor cytoplasmic tail (Yarden Y. and Sliwkowski, M. X. (2001) *Nat. Rev. Mol. Cell. Biol.* 2:127-137). Here, a simplified PI3K-AKT cascade was implemented, whereby PI3K binds directly to ligand-bound heterodimers, activates PIP2, which forms a complex with PDK1 and AKT, leading to a two step double phosphorylation of AKT. ErbB3 has six sites for PI3K binding, whereas the other ErbB receptors only have one (Wallasch, C. et al. (1995) *EMBO J.* 14:4267-4275; Soltoff, S. P. et al. (1994) *Mol. Cell. Biol.* 14:3550-3558). Although it is not known whether six PI3K molecules can bind simultaneously to ErbB3, PI3K is activated 10-20 times more strongly by ErbB3 (Fedi, P. et al. (1994) *Mol. Cell. Biol.* 14:492-500) than by the other receptors. There is also evidence that PI3K binds to ErbB3 with greater affinity than it does to the other ErbB receptors (Jones, R. B. et al. (2006) *Nature* 439:168-174). We incorporated these phenomena into the model and avoided the combinatorial complexity of including six binding sites, by imposing the following stipulations on ErbB3-containing dimers: An enhanced PI3K-binding rate; enhanced PIP2-binding rate to PI3K, and enhanced activation rate of PIP3. PIP2 is not present in endosomes (Haugh, J. M. (2002) *Mol. Interv.* 2:292-307), thus, only plasma membrane-bound receptor dimers are capable of activating PIP2 in the model. Initial simulations accelerated AKT activation too slowly, making it necessary to almost completely deactivate the AKT phosphatase prior to simulation and incorporate a negative feedback loop whereby AKT activates its own phosphatase, a phenomenon described elsewhere (Camps, M. et al. (1998) *Science* 280:1262-1265). The MAPK cascade was neglected both for simplicity and because of our recent findings that AKT signaling is relatively insensitive to species and parameters in the MAPK cascade (Chen, W. W. et al. (2009) *Mol. Syst. Biol.* 5:239); therefore, MAPK-PI3K crosstalk is not required to describe AKT signaling dynamics. Initial species values were directly measured (ErbB receptors, PDK1, AKT), inferred from the literature (Birtwistle, M. R. et al. (2007) *Mol. Syst. Biol.* 3:144; Hatakeyama, M. et al. (2003) *Biochem. J.* 373:451-453) or set to non-rate-limiting values.

Model Calibration

Many of the reaction rate parameters are unknown in the cell system we studied and therefore had to be estimated (see Table 10 below). To avoid biasing the starting point, all parameters were set to default values (Aldridge, B. B. et al. (2006) *Nat. Cell. Biol.* 8:1195-1203). The number of parameters estimated was limited by performing the estimation in two stages: first the model was calibrated against the experimentally observed ErbB receptor phosphorylation data; second, the parameters sensitive to AKT phosphorylation were optimized against the experimental data. Estimated values were only accepted if the parameters were constrained under multiple parameter runs using a genetic algorithm with a population size of 50 and 25 generations (Mathworks, Mass.). The ligand binding rate constants of HRG1-β and BTC were estimated separately using known $K_d$s (Tzahar, E. et al. (1996) *Mol. Cell. Biol.* 16:5276-5287; Singer, E. et al. (2001) *J. Biol. Chem.* 276:44266-44274; Jones, J. T. et al. (1999) *FEBS Lett.* 447:227-231) and initial dose responses curves to approximate a forward binding rate of $1 \times 10^5 M^{-1} s^{-1}$ for both ligands. Sensitivity analyses (Mathworks, MA) were performed to identify parameters that strongly influenced the activities of ErbB1, ErbB2, ErbB3, and AKT phosphorylation with HRG1-β or BTC stimulation (see Table 11 below). Each parameter was permitted to vary separately while the system was stimulated with either 1 nM of HRG1-β or BTC. The normalized sensitivities of each species were integrated over the two hour stimulation, and parameters with normalized, integrated sensitivities greater than an arbitrary threshold of 1000 are listed in Table 11 below. As mentioned above, ErbB4 phosphorylation was not included into the parameter estimation because the cell line studied had barely detectable ErbB4 (see Table 3 below). ErbB4 reactions are parameterized according to ErbB3 reactions.

The ErbB receptor phosphorylation profiles were sensitive to dimerization, internalization, recycling, and degradation parameters (enzymatic reactions, dimer dissociation, and phosphatase rate constants were not sensitive). These parameters were fit using a high-density dataset. Each readout was normalized to the maximum activation achieved by either ligand, preserving the relative potency of each ligand. ErbB receptor dimerization rates were tightly constrained and parameter relationships were observed that paralleled literature findings: ErbB2 is the preferred dimerization partner for ligand-bound ErbB1 or ErbB3 (more noticeably with heregulin stimulation). From the available data, it was not possible to constrain both the recycling and internalization rates; therefore recycling rates were set to 0.005 s$^{-1}$ and only internalization rates were fit: The resulting observations therefore apply equally to recycling rates (in inverse). Internalization rates varied based on ligand stimulus, with HRG1-β-bound dimers exhibiting much slower internalization than BTC-bound homo- and heterodimers, a view supported elsewhere (Sorkin, A. and Goh, L. K. (2008) Exp. Cell Res. 314:3093-3106). Degradation rates were also well constrained, but were similar for all dimers, suggesting that individual dimer degradation rates are not required to explain the observed data. Phosphorylated AKT is sensitive to many parameters within the PI3K cascade and at the receptor level (see Table 11 below). Therefore, we restricted the calibration to model parameters that were in the PI3K-AKT cascade and trained against the time courses of AKT phosphorylation while we locked the parameter values already trained on the ErbB receptor profiles.

Following model training, local, manual adjustment of parameters was performed to decipher the impact of each parameter, to determine if further improvement was possible, and to restrict parameters to biologically plausible values. For standardization, parameters were rounded and condensed to similar values when conserved across a parameter type (as explained for degradation rates).

Inhibitor Implementation

ErbB network inhibitors were included in the model using the simplest interpretation of known mechanisms of action (see Table 12 below): the anti-ErbB3 monoclonal antibody Ab #6 sequesters ErbB3 by preventing ligand binding and induces internalization and degradation; cetuximab sequesters ErbB1 and prevents ligand binding; lapatinib inhibits activation of ErbB receptors but not dimerization or ligand binding; and pertuzumab blocks ErbB2 dimerization. For Ab #6, the rate constants measured by Kinexa were used and for the other inhibitors the rate constants reported in the literature (Wood, E. R. et al. (2004) Cancer Res. 64:6652-6659; Patel, D. et al. (2007) Anticancer Res. 27:3355-3366; Adams, C. W. et al. (2006) Cancer Immunol. Immunother. 55:717-727) and listed in Table 13 below were used; cetuximab parameters were experimentally confirmed by Kinexa.

Various additional information used in the development of the computational model of the ErbB signaling pathway is set forth below in Tables 3-13, as follows:

TABLE 3

Measured ErbB receptor expression and mutation status for investigated cell lines.

| cell line | Tumor Type | ErbB abundance (molecules/cell)[#] | | | | Mutation status[*] | | |
|---|---|---|---|---|---|---|---|---|
| | | ErbB1 | ErbB2 | ErbB3 | ErbB4 | KRAS | PI3K | PTEN |
| ADRr | ovarian | 177818 | 40792 | 33205 | 2094 | none | none | none |
| OvCAR8 | ovarian | 236157 | 53272 | 31813 | ND | none | none | none |
| ACHN | renal | 448284 | 45456 | 15200 | 2086 | none | none | none |
| MALME-3M | melanoma | 2914 | 56422 | 67367 | 584 | none | none | none |
| DU145 | prostate | 437841 | 69068 | 19422 | ND | none | none | none |

ND—non-detectable
[#]as measured by qFACS
[*]Web site used to determine the mutation status of the cell lines investigated - http://www.sanger.ac.uk/perl/genetics/CGP/core_line_viewer?action=nci60_list

TABLE 4

Characterization of ErbB1 phosphorylation dose response curves for ErbB1 binding ligands and HRG1-β.

| pErbB1 | | NCI-ADRr | % stimulation at 5 min relative to maximum |
|---|---|---|---|
| EGF | $EC_{50}$ [nM] | 6.0 | 100.0 |
| | 95% CI | 2.5-14 | |
| HB-EGF | $EC_{50}$ [nM] | 21.0 | 87.0 |
| | 95% CI | 12-38 | |
| Epigen | $EC_{50}$ [nM] | ND | 12.0 |
| | 95% CI | | |
| AR | $EC_{50}$ [nM] | 37.0 | 95.0 |
| | 95% CI | 21-68 | |
| BTC | $EC_{50}$ [nM] | 5.7 | 100.0 |
| | 95% CI | 2.3-14 | |
| TGFα | $EC_{50}$ [nM] | 30.0 | 100.0 |
| | 95% CI | 10-87 | |
| Epiregulin | $EC_{50}$ [nM] | ND | 9.0 |
| | 95% CI | | |
| HRG1-β | $EC_{50}$ [nM] | ND | 0.0 |

ND: could not be determined
CI: 95% Confidence Interval

TABLE 5

Characterization of ErbB2 phosphorylation dose response curves for ErbB1 binding ligands and HRG1-beta

| pErbB2 | | NCI-ADRr | % stimulation at 5 min relative to maximum |
|---|---|---|---|
| EGF | $EC_{50}$ [nM] | 27.0 | 100.0 |
| | 95% CI | 15-51 | |
| HB-EGF | $EC_{50}$ [nM] | 230.0 | 94.0 |
| | 95% CI | 74-730 | |
| Epigen | $EC_{50}$ [nM] | ND | 25.0 |
| | 95% CI | | |
| AR | $EC_{50}$ [nM] | ND | 54.0 |
| | 95% CI | | |
| BTC | $EC_{50}$ [nM] | 27.0 | 94.0 |
| | 95% CI | 4-190 | |
| TGFα | $EC_{50}$ [nM] | 41.0 | 36.0 |
| | 95% CI | 20-86 | |
| Epiregulin | $EC_{50}$ [nM] | ND | 18.0 |
| | 95% CI | | |
| HRG1-β | $EC_{50}$ [nM] | 7.0 | 43.0 |
| | 95% CI | 2.1-23 | |

ND: could not be determined
CI: 95% Confidence Interval

TABLE 6

Characterization of ErbB3 phosphorylation dose response curves for ErbB1 binding ligands and HRG1-beta

| pErbB3 | | NCI-ADRr | % stimulation at 5 min relative to maximum |
|---|---|---|---|
| EGF | $EC_{50}$ [nM] | ND | 7.0 |
| | 95% CI | | |
| HB-EGF | $EC_{50}$ [nM] | ND | 32.0 |
| | 95% CI | | |
| Epigen | $EC_{50}$ [nM] | ND | 3.0 |
| | 95% CI | | |
| AR | $EC_{50}$ [nM] | 380.0 | 17.0 |
| | 95% CI | 240-600 | |
| BTC | $EC_{50}$ [nM] | 100.0 | 35.0 |
| | 95% CI | 47-220 | |
| TGFα | $EC_{50}$ [nM] | ND | 9.0 |
| | 95% CI | | |
| Epiregulin | $EC_{50}$ [nM] | ND | 22.0 |
| | 95% CI | | |
| HRG1-β | $EC_{50}$ [nM] | 9.9 | 100.0 |
| | 95% CI | 7.9-12 | |

ND: could not be determined
CI: 95% Confidence Interval

TABLE 7

Characterization of AKT phosphorylation dose response curves for ErbB1 binding ligands and HRG1-beta

| pAKT | | NCI-ADRr | % stimulation at 5 min relative to maximum |
|---|---|---|---|
| EGF | $EC_{50}$ [nM] | ND | 26.0 |
| | 95% CI | | |
| HB-EGF | $EC_{50}$ [nM] | ND | 20.0 |
| | 95% CI | | |
| Epigen | $EC_{50}$ [nM] | ND | 11.0 |
| | 95% CI | | |
| AR | $EC_{50}$ [nM] | 0.0 | 28.0 |
| | 95% CI | 0.064-27 | |
| BTC | $EC_{50}$ [nM] | ND | 22.0 |
| | 95% CI | | |
| TGFα | $EC_{50}$ [nM] | ND | 27.0 |
| | 95% CI | | |
| Epiregulin | $EC_{50}$ [nM] | ND | 11.0 |
| | 95% CI | | |
| HRG1-β | $EC_{50}$ [nM] | 1.9 | 100.0 |
| | 95% CI | 0.23-17.1 | |

ND: could not be determined
CI: 95% Confidence Interval

TABLE 8

Initial amounts of non-zero species in the computational model.

| Species name | Initial Amount | Additional description |
|---|---|---|
| HRG | variable | Heregulin |
| BTC | variable | Betacellulin |
| E1 | 178000 | ErbB1 |
| E2 | 41000 | ErbB2 |
| E3 | 33000 | ErbB3 |
| RTKpase | 500000 | Receptor tyrosine kinase phosphatase |
| PI3K | 800000 | phosphatidylinositol 3-kinase |
| PIP2 | 700000 | phosphatidylinositol bisphosphate |
| PTEN | 350000 | PTEN deleted from chromosome 10 |
| PDK1 | 9500000 | phosphoinositide-dependent protein kinase |
| AKT | 900000 | Serine, threonine protein kinase also known as protein kinase B |
| PP2A | 4000 | Protein phosphatase 2A (AKT phosphatase) |
| PP2Aoff | 64000 | Inactive AKT phosphatase |

TABLE 9

Summary of biochemical reactions implemented into the computational model using mass action kinetics with corresponding parameters

| Reaction Number | Reaction | Forward parameter | Reverse parameter |
|---|---|---|---|
| Ligand Binding | | | |
| v1 | HRG + E3 <-> [E3:HRG] | kf1 | kr1 |
| v2 | HRG + [E2:E3] <-> [E2:E3:HRG] | kf2 | kr2 |
| v3 | BTC + E1 <-> [BTC:E1] | kf3 | kr3 |
| v4 | BTC + [E1:E1] <-> [BTC:E1:E1] | kf4 | kr3 |
| v5 | BTC + [E1:E2] <-> [BTC:E1:E2] | kf5 | kr3 |
| v6 | BTC + [E1:E3] <-> [BTC:E1:E3] | kf5 | kr3 |

TABLE 9-continued

Summary of biochemical reactions implemented into the computational model using mass action kinetics with corresponding parameters

| Reaction Number | Reaction | Forward parameter | Reverse parameter |
|---|---|---|---|
| Dimerization | | | |
| v7 | [E3:HRG] + E2 <-> [E2:E3:HRG] | kf7 | kr7 |
| v8 | [E3:HRG_p] + E2_p <-> [E2:E3:HRG_p] | kf7 | kr7 |
| v9 | [E3:HRG_p] + E2 -> [E2:E3:HRG_p] | kf7 | |
| v10 | [E3:HRG] + E1 <-> [E1:E3:HRG] | kf10 | kr7 |
| v11 | [E3:HRG_p] + E1 <-> [E1:E3:HRG_p] | kf10 | kr7 |
| v12 | E2_p + E2 -> [E2:E2_p] | kf12 | |
| v13 | E2_p + E2_p <-> [E2:E2_p] | kf12 | kr12 |
| v14 | [BTC:E1] + E1 <-> [BTC:E1:E1] | kf14 | kr14 |
| v15 | [BTC:E1_p] + E1 <-> [BTC:E1:E1_p] | kf14 | kr14 |
| v16 | [BTC:E1] + [BTC:E1] <-> [BTC:E1:E1:BTC] | kf16 | kr16 |
| v17 | [BTC:E1_p] + [BTC:E1] <-> [BTC:E1:E1:BTC_p] | kf16 | kr16 |
| v18 | [BTC:E1_p] + [BTC:E1_p] <-> [BTC:E1:E1:BTC_p] | kf16 | kr16 |
| v19 | [BTC:E1] + E2 <-> [BTC:E1:E2] | kf19 | kr19 |
| v20 | [BTC:E1] + E2_p -> [BTC:E1:E2_p] | kf19 | |
| v21 | [BTC:E1_p] + E2_p <-> [BTC:E1:E2_p] | kf19 | kr19 |
| v22 | [BTC:E1_p] + E2 -> [BTC:E1:E2_p] | kf19 | |
| v23 | [BTC:E1] + E3 <-> [BTC:E1:E3] | kf23 | kr19 |
| v24 | [BTC:E1_p] + E3 <-> [BTC:E1:E3_p] | kf23 | kr19 |
| v25 | E3 + E2 <-> [E2:E3] | kf12 | kr12 |
| v26 | E3 + E1 <-> [E1:E3] | kf12 | kr12 |
| v27 | E1 + E2 <-> [E1:E2] | kf12 | kr12 |
| v28 | E1 + E1 <-> [E1:E1] | kf12 | kr12 |
| v29 | E2 + E2 <-> [E2:E2] | kf12 | kr12 |
| Phosphorylation and dephosphorylation | | | |
| v30 | [E2:E3:HRG] -> [E2:E3:HRG_p] | kf30 | |
| v31 | [E1:E3:HRG] -> [E1:E3:HRG_p] | kf30 | |
| v32 | [BTC:E1:E1] -> [BTC:E1:E1_p] | kf30 | |
| v33 | [BTC:E1:E1:BTC] -> [BTC:E1:E1:BTC_p] | kf30 | |
| v34 | [BTC:E1:E2] -> [BTC:E1:E2_p] | kf30 | |
| v35 | [BTC:E1:E3] -> [BTC:E1:E3_p] | kf30 | |
| v36 | [E3:HRG_p] -> HRG + E3 | kr1 | |
| v37 | [BTC:E1_p] -> BTC + E1 | kr3 | |
| v38 | [E2:E3:HRG_p] + RTKpase <-> [E2:E3:HRG_p:RTKpase] | kf38 | kr38 |
| v39 | [E1:E3:HRG_p] + RTKpase <-> [E1:E3:HRG_p:RTKpase] | kf38 | kr38 |
| v40 | [BTC:E1:E1_p] + RTKpase <-> [BTC:E1:E1_p:RTKpase] | kf38 | kr38 |
| v41 | [BTC:E1:E1:BTC_p] + RTKpase <-> [BTC:E1:E1:BTC_p:RTKpase] | kf38 | kr38 |
| v42 | [BTC:E1:E2_p] + RTKpase <-> [BTC:E1:E2_p:RTKpase] | kf38 | kr38 |
| v43 | [BTC:E1:E3_p] + RTKpase <-> [BTC:E1:E3_p:RTKpase] | kf38 | kr38 |
| v44 | [E2:E2_p] + RTKpase <-> [E2:E2_p:RTKpase] | kf38 | kr38 |
| v45 | [E2:E3:HRG_p:RTKpase] -> [E2:E3:HRG] + RTKpase | kf45 | |
| v46 | [E1:E3:HRG_p:RTKpase] -> [E1:E3:HRG] + RTKpase | kf45 | |
| v47 | [BTC:E1:E1_p:RTKpase] -> [BTC:E1:E1] + RTKpase | kf45 | |
| v48 | [BTC:E1:E1:BTC_p:RTKpase] -> [BTC:E1:E1:BTC] + RTKpase | kf45 | |
| v49 | [BTC:E1:E2_p:RTKpase] -> [BTC:E1:E2] + RTKpase | kf45 | |
| v50 | [BTC:E1:E3_p:RTKpase] -> [BTC:E1:E3] + RTKpase | kf45 | |
| v51 | [E2:E2_p:RTKpase] -> [E2:E2] + RTKpase | kf45 | |
| PI3K binding and PIP2 activation | | | |
| v52 | [E2:E3:HRG_p] + PI3K <-> [E2:E3:HRG_p:PI3K] | kf52 | kr52 |
| v53 | [E1:E3:HRG_p] + PI3K <-> [E1:E3:HRG_p:PI3K] | kf52 | kr52 |
| v54 | [E2:E2_p] + PI3K <-> [E2:E2_p:PI3K] | kf54 | kr54 |
| v55 | [BTC:E1:E1_p] + PI3K <-> [BTC:E1:E1_p:PI3K] | kf54 | kr54 |
| v56 | [BTC:E1:E1:BTC_p] + PI3K <-> [BTC:E1:E1:BTC_p:PI3K] | kf54 | kr54 |
| v57 | [BTC:E1:E2_p] + PI3K <-> [BTC:E1:E2_p:PI3K] | kf54 | kr54 |
| v58 | [BTC:E1:E3_p] + PI3K <-> [BTC:E1:E3_p:PI3K] | kf52 | kr52 |
| v59 | [E2:E3:HRG_p:PI3K] + PIP2 <-> [E2:E3:HRG_p:PI3K:PIP2] | kf59 | kr59 |
| v60 | [E1:E3:HRG_p:PI3K] + PIP2 <-> [E1:E3:HRG_p:PI3K:PIP2] | kf59 | kr59 |
| v61 | [E2:E2_p:PI3K] + PIP2 <-> [E2:E2_p:PI3K:PIP2] | kf61 | kr61 |
| v62 | [BTC:E1:E1_p:PI3K] + PIP2 <-> [BTC:E1:E1_p:PI3K:PIP2] | kf61 | kr61 |
| v63 | [BTC:E1:E1:BTC_p:PI3K] + PIP2 <-> [BTC:E1:E1:BTC_p:PI3K:PIP2] | kf61 | kr61 |
| v64 | [BTC:E1:E2_p:PI3K] + PIP2 <-> [BTC:E1:E2_p:PI3K:PIP2] | kf61 | kr61 |
| v65 | [BTC:E1:E3_p:PI3K] + PIP2 <-> [BTC:E1:E3_p:PI3K:PIP2] | kf59 | kr59 |
| v66 | [E2:E3:HRG_p:PI3K:PIP2] -> [E2:E3:HRG_p:PI3K] + PIP3 | kf66 | |

TABLE 9-continued

Summary of biochemical reactions implemented into the computational model using mass action kinetics with corresponding parameters

| Reaction Number | Reaction | Forward parameter | Reverse parameter |
|---|---|---|---|
| v67 | [E1:E3:HRG_p:PI3K:PIP2] -> [E1:E3:HRG_p:PI3K] + PIP3 | kf66 | |
| v68 | [E2:E2_p:PI3K:PIP2] -> [E2:E2_p:PI3K] + PIP3 | kf68 | |
| v69 | [BTC:E1:E1_p:PI3K:PIP2] -> [BTC:E1:E1_p:PI3K] + PIP3 | kf68 | |
| v70 | [BTC:E1:E1:BTC_p:PI3K:PIP2] -> [BTC:E1:E1:BTC_p:PI3K] + PIP3 | kf68 | |
| v71 | [BTC:E1:E2_p:PI3K:PIP2] -> [BTC:E1:E2_p:PI3K] + PIP3 | kf68 | |
| v72 | [BTC:E1:E3_p:PI3K:PIP2] -> [BTC:E1:E3_p:PI3K] + PIP3 | kf66 | |
| AKT activation cascade | | | |
| v73 | PIP3 + PTEN <-> [PIP3:PTEN] | kf73 | kr73 |
| v74 | [PIP3:PTEN] -> PIP2 + PTEN | kf74 | |
| v75 | PIP3 + AKT <-> [PIP3:AKT] | kf75 | kr75 |
| v76 | [PIP3:AKT] + PDK1 <-> [PIP3:AKT:PDK1] | kf76 | kr76 |
| v77 | [PIP3:AKT:PDK1] -> AKT_p + [PIP3:PDK1] | kf77 | |
| v78 | [PIP3:PDK1] -> PIP3 + PDK1 | kf78 | |
| v79 | PIP3 + AKT_p <-> [PIP3:AKT_p] | kf75 | kr75 |
| v80 | [PIP3:AKT_p] + PDK1 <-> [PIP3:AKT_p:PDK1] | kf76 | kr76 |
| v81 | [PIP3:AKT_p:PDK1] -> AKT_p_p + [PIP3:PDK1] | kf81 | |
| v82 | AKT_p_p + PP2A <-> [AKT_p_p:PP2A] | kf82 | kr82 |
| v83 | [AKT_p_p:PP2A] -> AKT_p + PP2A | kf83 | |
| v84 | AKT_p + PP2A <-> [AKT_p:PP2A] | kf82 | kr82 |
| v85 | [AKT_p:PP2A] -> AKT + PP2A | kf83 | |
| v86 | AKT_p_p + PP2Aoff <-> [AKT_p_p:PP2Aoff] | kf86 | kr86 |
| v87 | [AKT_p_p:PP2Aoff] -> AKT_p_p + PP2A | kf87 | |
| Internalizaton | | | |
| v88 | [E3:HRG] <-> [iE3:HRG] | kf88 | kr88 |
| v89 | [E3:HRG_p] <-> [iE3:HRG_p] | kf88 | kr88 |
| v90 | E2_p <-> iE2_p | kf88 | kr88 |
| v91 | [BTC:E1] <-> [iBTC:E1] | kf88 | kr88 |
| v92 | [BTC:E1_p] <-> [iBTC:E1_p] | kf88 | kr88 |
| v93 | [E2:E3:HRG] <-> [iE2:E3:HRG] | kf93 | kr93 |
| v94 | [E2:E3:HRG_p] <-> [iE2:E3:HRG_p] | kf93 | kr93 |
| v95 | [E2:E3:HRG_p:RTKpase] <-> [iE2:E3:HRG_p:RTKpase] | kf93 | kr93 |
| v96 | [E2:E3:HRG_p:PI3K] <-> [iE2:E3:HRG_p:PI3K] | kf93 | kr93 |
| v97 | [E2:E3:HRG_p:PI3K:PIP2] <-> [iE2:E3:HRG_p:PI3K:PIP2] | kf93 | kr93 |
| v98 | [E1:E3:HRG] <-> [iE1:E3:HRG] | kf98 | kr98 |
| v99 | [E1:E3:HRG_p] <-> [iE1:E3:HRG_p] | kf98 | kr98 |
| v100 | [E1:E3:HRG_p:RTKpase] <-> [iE1:E3:HRG_p:RTKpase] | kf98 | kr98 |
| v101 | [E1:E3:HRG_p:PI3K] <-> [iE1:E3:HRG_p:PI3K] | kf98 | kr98 |
| v102 | [E1:E3:HRG_p:PI3K:PIP2] <-> [iE1:E3:HRG_p:PI3K:PIP2] | kf98 | kr98 |
| v103 | [E2:E2_p] <-> [iE2:E2_p] | kf93 | kr93 |
| v104 | [E2:E2_p:RTKpase] <-> [iE2:E2_p:RTKpase] | kf93 | kr93 |
| v105 | [E2:E2_p:PI3K] <-> [iE2:E2_p:PI3K] | kf93 | kr93 |
| v106 | [E2:E2_p:PI3K:PIP2] <-> [iE2:E2_p:PI3K:PIP2] | kf93 | kr93 |
| v107 | [BTC:E1:E1] <-> [iBTC:E1:E1] | kf107 | kr107 |
| v108 | [BTC:E1:E1:BTC] <-> [iBTC:E1:E1:BTC] | kf107 | kr107 |
| v109 | [BTC:E1:E1_p] <-> [iBTC:E1:E1_p] | kf107 | kr107 |
| v110 | [BTC:E1:E1:BTC_p] <-> [iBTC:E1:E1:BTC_p] | kf107 | kr107 |
| v111 | [BTC:E1:E1_p:RTKpase] <-> [iBTC:E1:E1_p:RTKpase] | kf107 | kr107 |
| v112 | [BTC:E1:E1:BTC_p:RTKpase] <-> [iBTC:E1:E1:BTC_p:RTKpase] | kf107 | kr107 |
| v113 | [BTC:E1:E1_p:PI3K] <-> [iBTC:E1:E1_p:PI3K] | kf107 | kr107 |
| v114 | [BTC:E1:E1:BTC_p:PI3K] <-> [iBTC:E1:E1:BTC_p:PI3K] | kf107 | kr107 |
| v115 | [BTC:E1:E1_p:PI3K:PIP2] <-> [iBTC:E1:E1_p:PI3K:PIP2] | kf107 | kr107 |
| v116 | [BTC:E1:E1:BTC_p:PI3K:PIP2] <-> [iBTC:E1:E1:BTC_p:PI3K:PIP2] | kf107 | kr107 |
| v117 | [BTC:E1:E2] <-> [iBTC:E1:E2] | kf117 | kr117 |
| v118 | [BTC:E1:E2_p] <-> [iBTC:E1:E2_p] | kf117 | kr117 |
| v119 | [BTC:E1:E2_p:RTKpase] <-> [iBTC:E1:E2_p:RTKpase] | kf117 | kr117 |
| v120 | [BTC:E1:E2_p:PI3K] <-> [iBTC:E1:E2_p:PI3K] | kf117 | kr117 |
| v121 | [BTC:E1:E2_p:PI3K:PIP2] <-> [iBTC:E1:E2_p:PI3K:PIP2] | kf117 | kr117 |
| v122 | [BTC:E1:E3] <-> [iBTC:E1:E3] | kf117 | kr117 |
| v123 | [BTC:E1:E3_p] <-> [iBTC:E1:E3_p] | kf117 | kr117 |
| v124 | [BTC:E1:E3_p:RTKpase] <-> [iBTC:E1:E3_p:RTKpase] | kf117 | kr117 |
| v125 | [BTC:E1:E3_p:PI3K] <-> [iBTC:E1:E3_p:PI3K] | kf117 | kr117 |
| v126 | [BTC:E1:E3_p:PI3K:PIP2] <-> [iBTC:E1:E3_p:PI3K:PIP2] | kf117 | kr117 |
| Endosomal ligand binding | | | |
| v127 | iHRG + iE3 <-> [iE3:HRG] | kf127 | kr1 |
| v128 | iHRG + [iE2:E3] <-> [iE2:E3:HRG] | kf127 | kr1 |
| v129 | iBTC + iE1 <-> [iBTC:E1] | kf129 | kr3 |
| v130 | iBTC + [iE1:E1] <-> [iBTC:E1:E1] | kf129 | kr3 |

TABLE 9-continued

Summary of biochemical reactions implemented into the computational model using mass action kinetics with corresponding parameters

| Reaction Number | Reaction | Forward parameter | Reverse parameter |
|---|---|---|---|
| v131 | iBTC + [iE1:E2] <-> [iBTC:E1:E2] | kf129 | kr3 |
| v132 | iBTC + [iE1:E3] <-> [iBTC:E1:E3] | kf129 | kr3 |
| Endosomal dimerization | | | |
| v133 | [iE3:HRG] + iE2 <-> [iE2:E3:HRG] | kf7 | kr7 |
| v134 | [iE3:HRG_p] + iE2_p <-> [iE2:E3:HRG_p] | kf7 | kr7 |
| v135 | [iE3:HRG_p] + iE2 -> [iE2:E3:HRG_p] | kf7 | |
| v136 | [iE3:HRG] + iE1 <-> [iE1:E3:HRG] | kf10 | kr7 |
| v137 | [iE3:HRG_p] + iE1 <-> [iE1:E3:HRG_p] | kf10 | kr7 |
| v138 | iE2_p + iE2 -> [iE2:E2_p] | kf12 | |
| v139 | iE2_p + iE2_p <-> [iE2:E2_p] | kf12 | kr12 |
| v140 | [iBTC:E1] + iE1 <-> [iBTC:E1:E1] | kf14 | kr14 |
| v141 | [iBTC:E1_p] + iE1 <-> [iBTC:E1:E1_p] | kf14 | kr14 |
| v142 | [iBTC:E1] + [iBTC:E1] <-> [iBTC:E1:E1:BTC] | kf16 | kr16 |
| v143 | [iBTC:E1_p] + [iBTC:E1] <-> [iBTC:E1:E1:BTC_p] | kf16 | kr16 |
| v144 | [iBTC:E1_p] + [iBTC:E1_p] <-> [iBTC:E1:E1:BTC_p] | kf16 | kr16 |
| v145 | [iBTC:E1] + iE2 <-> [iBTC:E1:E2] | kf19 | kr19 |
| v146 | [iBTC:E1_p] + iE2 -> [iBTC:E1:E2_p] | kf19 | |
| v147 | [iBTC:E1] + iE2_p -> [iBTC:E1:E2_p] | kf19 | |
| v148 | [iBTC:E1_p] + iE2_p <-> [iBTC:E1:E2_p] | kf19 | kr19 |
| v149 | [iBTC:E1] + iE3 <-> [iBTC:E1:E3] | kf23 | kr19 |
| v150 | [iBTC:E1_p] + iE3 <-> [iBTC:E1:E3_p] | kf23 | kr19 |
| v151 | iE3 + iE2 <-> [iE2:E3] | kf12 | kr12 |
| v152 | iE3 + iE1 <-> [iE1:E3] | kf12 | kr12 |
| v153 | iE1 + iE2 <-> [iE1:E2] | kf12 | kr12 |
| v154 | iE1 + iE1 <-> [iE1:E1] | kf12 | kr12 |
| v155 | iE2 + iE2 <-> [iE2:E2] | kf12 | kr12 |
| Endosomal phosphorylation and dephosphorylation | | | |
| v156 | [iE2:E3:HRG] -> [iE2:E3:HRG_p] | kf30 | |
| v157 | [iE1:E3:HRG] -> [iE1:E3:HRG_p] | kf30 | |
| v158 | [iBTC:E1:E1] -> [iBTC:E1:E1_p] | kf30 | |
| v159 | [iBTC:E1:E1:BTC] -> [iBTC:E1:E1:BTC_p] | kf30 | |
| v160 | [iBTC:E1:E2] -> [iBTC:E1:E2_p] | kf30 | |
| v161 | [iBTC:E1:E3] -> [iBTC:E1:E3_p] | kf30 | |
| v162 | [iE3:HRG_p] -> iHRG + iE3 | kr1 | |
| v163 | [iBTC:E1_p] -> iBTC + iE1 | kr3 | |
| v164 | [iE2:E3:HRG_p] + RTKpase <-> [iE2:E3:HRG_p:RTKpase] | kf38 | kr38 |
| v165 | [iE:E3:HRG_p] + RTKpase <-> [iE1:E3:HRG_p:RTKpase] | kf38 | kr38 |
| v166 | [iE2:E2_p] + RTKpase <-> [iE2:E2_p:RTKpase] | kf38 | kr38 |
| v167 | [iBTC:E1:E1_p] + RTKpase <-> [iBTC:E1:E1_p:RTKpase] | kf38 | kr38 |
| v168 | [iBTC:E1:E1 :BTC_p] + RTKpase <-> [iBTC:E1:E1:BTC_p:RTKpase] | kf38 | kr38 |
| v169 | [iBTC:E1:E2_p] + RTKpase <-> [iBTC:E1:E2_p:RTKpase] | kf38 | kr38 |
| v170 | [iBTC:E1:E3_p] + RTKpase <-> [iBTC:E1:E3_p:RTKpase] | kf38 | kr38 |
| v171 | [iE2:E3:HRG_p:RTKpase] -> [iE2:E3:HRG] + RTKpase | kf45 | |
| v172 | [iE1:E3:HRG_p:RTKpase] -> [iE1 E3:HRG] + RTKpase | kf45 | |
| v173 | [iE2:E2_p:RTKpase] -> [iE2:E2] + RTKpase | kf45 | |
| v174 | [iBTC:E1:E1_p:RTKpase] -> [iBTC:E1:E1] + RTKpase | kf45 | |
| v175 | [iBTC:E1:E1:BTC_p:RTKpase] -> [iBTC:E1:E1:BTC] + RTKpase | kf45 | |
| v176 | [iBTC:E1:E2_p:RTKpase] -> [iBTC:E1:E2] + RTKpase | kf45 | |
| v177 | [iBTC:E1:E3_p:RTKpase] -> [iBTC:E1:E3] + RTKpase | kf45 | |
| Endosomal PI3K binding | | | |
| v178 | [iE2:E3:HRG_p] + PI3K <-> [iE2:E3:HRG_p:PI3K] | kf52 | kr52 |
| v179 | [iE1:E3:HRG_p] + PI3K <-> [iE1:E3:HRG_p:PI3K] | kf52 | kr52 |
| v180 | [iE2:E2_p] + PI3K <-> [iE2:E2_p:PI3K] | kf54 | kr54 |
| v181 | [iBTC:E1:E1_p] + PI3K <-> [iBTC:E1:E1_p:PI3K] | kf54 | kr54 |
| v182 | [iBTC:E1:E1:BTC_p] + PI3K <-> [iBTC:E1:E1:BTC_p:PI3K] | kf54 | kr54 |
| v183 | [iBTC:E1:E2_p] + PI3K <-> [iBTC:E1:E2_p:PI3K] | kf54 | kr54 |
| v184 | [iBTC:E1:E3_p] + PI3K <-> [iBTC:E1:E3_p:PI3K] | kf52 | kr52 |
| Degradation | | | |
| v185 | iHRG -> dHRG | kf185 | |
| v186 | iBTC -> dBTC | kf185 | |
| v187 | [iE3:HRG] -> [dE3:HRG] | kf187 | |
| v188 | [iBTC:E1] -> [dBTC:E1] | kf187 | |
| v189 | [iE3:HRG_p] -> [dE3:HRG_p] | kf187 | |
| v190 | [iBTC:E1_p] -> [dBTC:E1_p] | kf187 | |
| v191 | iE2_p -> dE2_p | kf187 | |
| v192 | [iE2:E3:HRG] -> [dE2:E3:HRG] | kf192 | |
| v193 | [iE2:E3:HRG_p] -> [dE2:E3:HRG_p] | kf192 | |
| v194 | [iE2:E3:HRG_p:RTKpase] -> [dE2:E3:HRG_p:RTKpase] | kf192 | |

TABLE 9-continued

Summary of biochemical reactions implemented into the computational model using mass action kinetics with corresponding parameters

| Reaction Number | Reaction | Forward parameter | Reverse parameter |
|---|---|---|---|
| v195 | [iE2:E3:HRG_p:PI3K] -> [dE2:E3:HRG_p:PI3K] | kf192 | |
| v196 | [iE2:E3:HRG_p:PI3K:PIP2] -> [dE2:E3:HRG_p:PI3K:PIP2] | kf192 | |
| v197 | [iE2:E2_p] -> [dE2:E2_p] | kf192 | |
| v198 | [iE2:E2_p:RTKpase] -> [dE2:E2_p:RTKpase] | kf192 | |
| v199 | [iE2:E2_p:PI3K] -> [dE2:E2_p:PI3K] | kf192 | |
| v200 | [iE2:E2_p:PI3K:PIP2] -> [dE2:E2_p:PI3K:PIP2] | kf192 | |
| v201 | [iE1:E3:HRG] -> [dE1:E3:HRG] | kf201 | |
| v202 | [iE1:E3:HRG_p] -> [dE1:E3:HRG_p] | kf201 | |
| v203 | [iE1:E3:HRG_p:RTKpase] -> [dE1:E3:HRG_p:RTKpase] | kf201 | |
| v204 | [iE1:E3:HRG_p:PI3K] -> [dE1:E3:HRG_p:PI3K] | kf201 | |
| v205 | [iE1:E3:HRG_p:PI3K:PIP2] -> [dE1:E3:HRG_p:PI3K:PIP2] | kf201 | |
| v206 | [iBTC:E1:E1] -> [dBTC:E1:E1] | kf206 | |
| v207 | [iBTC:E1:E1_p] -> [dBTC:E1:E1_p] | kf206 | |
| v208 | [iBTC:E1:E1_p:RTKpase] -> [dBTC:E1:E1_p:RTKpase] | kf206 | |
| v209 | [iBTC:E1:E1_p:PI3K] -> [dBTC:E1:E1_p:PI3K] | kf206 | |
| v210 | [iBTC:E1:E1_p:PI3K:PIP2] -> [dBTC:E1:E1_p:PI3K:PIP2] | kf206 | |
| v211 | [iBTC:E1:E1:BTC] -> [dBTC:E1:E1:BTC] | kf206 | |
| v212 | [iBTC:E1:E1:BTC_p] -> [dBTC:E1:E1:BTC_p] | kf206 | |
| v213 | [iBTC:E1:E1:BTC_p:RTKpase] -> [dBTC:E1:E1:BTC_p:RTKpase] | kf206 | |
| v214 | [iBTC:E1:E1:BTC_p:PI3K] -> [dBTC:E1:E1:BTC_p:PI3K] | kf206 | |
| v215 | [iBTC:E1:E1:BTC_p:PI3K:PIP2] -> [dBTC:E1:E1:BTC_p:PI3K:PIP2] | kf206 | |
| v216 | [iBTC:E1:E2] -> [dBTC:E1:E2] | kf201 | |
| v217 | [iBTC:E1:E2_p] -> [dBTC:E1:E2_p] | kf201 | |
| v218 | [iBTC:E1:E2_p:RTKpase] -> [dBTC:E1:E2_p:RTKpase] | kf201 | |
| v219 | [iBTC:E1:E2_p:PI3K] -> [dBTC:E1:E2_p:PI3K] | kf201 | |
| v220 | [iBTC:E1:E2_p:PI3K:PIP2] -> [dBTC:E1:E2_p:PI3K:PIP2] | kf201 | |
| v221 | [iBTC:E1:E3] -> [dBTC:E1:E3] | kf201 | |
| v222 | [iBTC:E1:E3_p] -> [dBTC:E1:E3_p] | kf201 | |
| v223 | [iBTC:E1:E3_p:RTKpase] -> [dBTC:E1:E3_p:RTKpase] | kf201 | |
| v224 | [iBTC:E1:E3_p:PI3K] -> [dBTC:E1:E3_p:PI3K] | kf201 | |
| v225 | [iBTC:E1:E3_p:PI3K:PIP2] -> [dBTC:E1:E3_p:PI3K:PIP2] | kf201 | |

Definition of abbreviations used:
: indicates a protein complex e.g. ligand bound to receptor
_p indicates that a protein is phosphorylated
iy indicates that a species y is internalized
<-> indicates a reversible reaction
-> indicates an irreversible reaction

TABLE 10

Description of parameters with values. Parameter number corresponds to first reaction in which that parameter appears

| Name | Value | Units | Description |
|---|---|---|---|
| Av | $6.0 \times 10^{23}$ | | Avogadro's number |
| Vmedia | $1.00 \times 10^{-04}$ | Liters | Media volume per well |
| Vcell | $1.00 \times 10^{-12}$ | Liters | Cell volume |
| Num cells | 30000 | | Number of cells per well. |
| kf1 | $5.00 \times 10^{-11}$ | molecules−1 sec−1 | HRG binding to E3 or E4. Unit conversion calculated as 1e5M−1s−1/ (Vmedia * Av/Num_cells). |
| kr1 | 0.001 | sec−1 | HRG dissociation from E3 |
| kf2 | $5.00 \times 10^{-11}$ | molecules−1 sec−1 | HRG binding to E3:E2 dimers |
| kr2 | 0.001 | sec−1 | HRG dissociation from E3:E2 dimers |
| kf3 | $5.00 \times 10^{-11}$ | molecules−1 sec−1 | BTC binding to E1 |
| kr3 | 0.001 | sec−1 | BTC dissociation from E1 |
| kf4 | $5.00 \times 10^{-11}$ | molecules−1 sec−1 | BTC binding to E1 homodimers |
| kf5 | $5.00 \times 10^{-11}$ | molecules−1 sec−1 | BTC binding to E1 heterodimers |
| kf7 | $3.00 \times 10^{-06}$ | molecules−1 sec−1 | Dimerization of E2 to HRG:E3 |
| kr7 | 0.001 | sec−1 | Dissociation of E2 to HRG:E3 |
| kf10 | $3.00 \times 10^{-08}$ | molecules−1 sec−1 | Dimerization of E1 to HRG:E3 |
| kf12 | $4.20 \times 10^{-09}$ | molecules−1 sec−1 | Dimerization-constitutive and ligand free |
| kr12 | 0.001 | sec−1 | Dissociation-constitutive and ligand free |
| kf14 | $1.70 \times 10^{-05}$ | molecules−1 sec−1 | Dimerization of E1 to BTC:E1 |
| kr14 | 0.001 | sec−1 | Dissociation of E1 to BTC:E1 |
| kf16 | $1.70 \times 10^{-05}$ | molecules−1 sec−1 | Dimerization of BTC:E1 to BTC:E1 |
| kr16 | 0.001 | sec−1 | Dissociation of BTC:E1 to BTC:E1 |
| kf19 | $3.30 \times 10^{-05}$ | molecules−1 sec−1 | Dimerization of E2 to BTC:E1 |
| kr19 | 0.001 | sec−1 | Dissociation of E2 or E3 to BTC:E1 |
| kf23 | $4.70 \times 10^{-06}$ | molecules−1 sec−1 | Dimerization of E3 to BTC:E1 |
| kf30 | 1 | sec−1 | Enzymatic auto-phosphorylation rate of ligand-bound dimers |

TABLE 10-continued

Description of parameters with values. Parameter number corresponds to first reaction in which that parameter appears

| Name | Value | Units | Description |
|---|---|---|---|
| kf38 | $5.00 \times 10^{-06}$ | molecules-1 sec-1 | Receptor phosphatase binding |
| kr38 | 0.1 | sec-1 | Receptor phosphatase dissociation |
| kf45 | 1 | sec-1 | Enzymatic rate for receptor dephosphorylation |
| kf52 | $3.00 \times 10^{-06}$ | molecules-1 sec-1 | PI3K binding to E3 containing dimers |
| kr52 | 0.1 | sec-1 | PI3K dissociation from E3 containing dimers |
| kf54 | $7.50 \times 10^{-06}$ | molecules-1 sec-1 | PI3K binding to non-E3 containing dimers |
| kr54 | 0.1 | sec-1 | PI3K dissociation from non-E3 dimers |
| kf59 | $5.00 \times 10^{-06}$ | molecules-1 sec-1 | PIP2 binding to E3 containing heterodimers |
| kr59 | 0.1 | sec-1 | PIP2 dissociation from E3 containing heterodimer |
| kf61 | $5.00 \times 10^{-07}$ | molecules-1 sec-1 | PIP2 binding to non-E3 containing heterodimers |
| kr61 | 0.1 | sec-1 | PIP2 dissociation from non-E3 containing heterodimer |
| kf66 | 0.2 | sec-1 | PIP3 activation by E3 containing dimers |
| kf68 | 0.013 | sec-1 | PIP3 activation rate by non E3 containing dimers |
| kf73 | $5.00 \times 10^{-06}$ | molecules-1 sec-1 | PIP3 binding to PTEN |
| kr73 | 0.1 | sec-1 | PIP3 dissociating from PTEN |
| kf74 | 0.1 | sec-1 | PIP3 inactivation by PTEN |
| kf75 | $2.60 \times 10^{-04}$ | molecules-1 sec-1 | PIP3 binding to Akt or Akt_p |
| kr75 | 0.1 | sec-1 | PIP3 dissociation from Akt or Akt_p |
| kf76 | $6.70 \times 10^{-05}$ | molecules-1 sec-1 | PDK1 binding to PIP3:Akt |
| kr76 | 0.1 | sec-1 | PDK1 dissociation from PIP3:Akt |
| kf77 | 1 | sec-1 | Enzymatic phosphorylation rate for Akt |
| kf78 | 0.2 | sec-1 | PDK1 dissociating from PIP3 |
| kf81 | 1 | sec-1 | Enzymatic phosphorylation rate for Akt_p |
| kf82 | $1.70 \times 10^{-06}$ | molecules-1 sec-1 | PP2A binding to phosphorylated Akt |
| kr82 | 0.1 | sec-1 | PP2A dissociation from phosphorylated Akt |
| kf83 | 1.5 | sec-1 | Akt dephosphorylation and dissociation |
| kf86 | $8.30 \times 10^{-09}$ | molecules-1 sec-1 | binding of AKT_p_p to PP2Aoff |
| kr86 | 0.5 | sec-1 | Dissociation of AKT_p_p from PP2Aoff |
| kf87 | 0.1 | sec-1 | Activation of PP2Aoff by AKT_p_p |
| kf88 | 0.1 | sec-1 | Internalization rate for ligand-bound or active monomers |
| kr88 | 0.005 | sec-1 | Recycling rate ligand-bound or active monomers |
| kf93 | 0.005 | sec-1 | Internalization rate for HRG-bound E2:E3 heterodimers and E2 homodimers |
| kr93 | 0.005 | sec-1 | Recycling rate for HRG-bound E2:E3 heterodimers and E2 homodimers |
| kf98 | 0.005 | sec-1 | Internalization rate for HRG-bound E1:E3 heterodimers |
| kr98 | 0.005 | sec-1 | Recycling rate for HRG-bound E1:E3 heterodimers |
| kf107 | 0.1 | sec-1 | Internalization rate for BTC-bound E1 homodimers |
| kr107 | 0.005 | sec-1 | Recycling rate for BTC-bound E1 homodimers |
| kf117 | 0.1 | sec-1 | Internalization rate for BTC-bound E1 heterodimers |
| kr117 | 0.005 | sec-1 | Recycling rate for BTC-bound E1 containing heterodimers |
| kf127 | 3.8 | molecules-1 sec-1 | HRG binding in the endosome |
| kf129 | 3.8 | molecules-1 sec-1 | BTC binding in the endosome |
| kf185 | 0.002 | sec-1 | Degradation rate for ligand |
| kf187 | 0.002 | sec-1 | Degradation rate for ligand bound monomers |
| kf192 | 0.002 | sec-1 | Degradation rate for ligand-bound E2 containing homo or heterodimers |
| kf201 | 0.002 | sec-1 | Degradation rate for ligand-bound E1 containing heterodimers |
| kf206 | 0.002 | sec-1 | Degradation of ligand-bound E1 homodimers |

TABLE 11

ErbB3, ErbB2, ErbB1. and AKT sensitive parameters.

| pErbB3 sensitivity during Heregulin stimulation | | pErbB3 sensitivity during Betacellulin stimulation | |
|---|---|---|---|
| kf1 | 4799 | kf5 | 3824 |
| kr93 | 2163 | kf23 | 2353 |
| kf7 | 1902 | kf3 | 1821 |
| kr88 | 1277 | kf12 | 1389 |
| kr12 | 1192 | kr12 | -1343 |
| kf12 | 1111 | kf14 | -1742 |
| kf187 | -1136 | kf14 | -6462 |
| kf88 | -1907 | | |
| kf93 | -3122 | | |
| kf192 | -4452 | | |

| pErbB2 sensitivity during Heregulin stimulation | | pErbB2 sensitivity during Betacellulin stimulation | |
|---|---|---|---|
| kf1 | 4747 | kf3 | 3878 |
| kr93 | 2245 | kf19 | 3124 |
| kf7 | 2136 | kf5 | 1060 |
| kr88 | 1267 | kf14 | -2768 |
| kr12 | 1155 | kf14 | -6515 |
| kf12 | -1071 | | |
| kf187 | -1137 | | |
| kf88 | -1892 | | |
| kf93 | -3239 | | |
| kf192 | -4617 | | |

| pErbB1 sensitivity during Heregulin stimulation | | pErbB1 sensitivity during Betacellulin stimulation | |
|---|---|---|---|
| kf10 | 6990 | kf3 | 2847 |
| kf1 | 6222 | kf4 | 1044 |
| kr12 | 2224 | kf14 | -1665 |
| kr98 | 2174 | kf206 | -4983 |
| kr88 | 1616 | | |
| kf187 | -423 | | |
| kf12 | -2189 | | |
| kf88 | -2414 | | |
| kf98 | -3155 | | |
| kf14 | -4457 | | |
| kf7 | -4469 | | |

TABLE 11-continued

ErbB3, ErbB2, ErbB1. and AKT sensitive parameters.

| pAKT sensitivity during Heregulin stimulation | | pAKT sensitivity during Betacellulin stimulation | |
|---|---|---|---|
| kf66 | 6657 | kf75 | 5462 |
| kf75 | 5418 | kf66 | 5395 |
| kf1 | 4799 | kr117 | 4420 |
| kr93 | 3937 | kf5 | 3250 |
| kr73 | 2705 | kr86 | 2854 |
| kf7 | 2022 | kr73 | 2726 |
| kr86 | 1918 | kf3 | 2351 |
| kf78 | 1584 | kf68 | 1815 |
| kr88 | 1209 | kf23 | 1804 |
| kr12 | 1127 | kf78 | 1750 |
| kf2 | −1044 | kr107 | 1024 |
| kf187 | −1073 | kf83 | −1019 |
| kf87 | −1929 | kf14 | −1338 |
| kf88 | −1967 | kf107 | −1552 |
| kf86 | −2302 | kf74 | −2720 |
| kf83 | −2520 | kf87 | −2861 |
| kf74 | −2719 | kf86 | −3425 |
| kf192 | −3667 | kf14 | −3890 |
| kf82 | −4458 | kf73 | −5459 |
| kf73 | −5416 | kf82 | −5921 |
| kf93 | −5748 | kf117 | −6849 |

TABLE 12

Implementation scheme for Ab

| Reaction Number | Reaction | Forward parameter | Reverse parameter |
|---|---|---|---|
| Ab #6 implementation | | | |
| Ab #6 _v1 | Ab #6 + E3 <-> [E3:Ab #6] | kfAb #6 _1 | krAb #6 _1 |
| Ab #6 _v2 | [E3:Ab #6] + E3 <-> [iE3:Ab #6:E3] | kfAb #6 _2 | krAb #6 _2 |
| Ab #6 _v3 | [E3:Ab #6:E3] <-> [iE3:Ab #6:E3] | kfAb #6 _3 | krAb #6 _3 |
| Ab #6 _v4 | [iE3:Ab #6:E3] <-> [dE3:Ab #6:E3] | kfAb #6 _4 | |
| Cetuximab implementation | | | |
| Cetuximab_v1 | Cetuximab + E1 <-> [E1:Cetuximab] | kfCetuximab_1 | krCetuximab_1 |
| Cetuximab_v2 | [E1:Cetuximab] + E1 <-> [E1:Cetuximab:E1] | kfCetuximab_2 | krCetuxmab_2 |
| Pertuzumab implementation | | | |
| Pertuzumab_v1 | [Pertuzumab] + E2 <-> [E2:Pertuzumab] | kfPertuzumab_1 | krPertuzumab_1 |
| Pertuzumab_v2 | [E2:Pertuzumab] + E2 <-> [E2:Pertuzumab:E2] | kfPertuzumab_2 | krPertuzumab_2 |
| Lapatinib implementation | | | |
| Lapatinib_v1 | Lapatinib + E1 <-> [Lapatinib:E1] | kfLapatinib_1 | krLapatinib_1 |
| Lapatinib_v2 | Lapatinib + E2 <-> [Lapatinib:E2] | kfLapatinib_2 | krLapatinib_2 |
| Lapatinib_v3 | Lapatinib + [E1:E1] <-> [Lapatinib:E1:E1] | kfLapatinib_3 | krLapatinib_1 |
| Lapatinib_v4 | Lapatinib + [E1:E2] <-> [Lapatinib:E1:E2] | kfLapatinib_3 | krLapatinib_1 |
| Lapatinib_v5 | Lapatinib + [E1:E3] <-> [Lapatinib:E1:E3] | kfLapatinib_1 | krLapatinib_1 |
| Lapatinib_v6 | Lapatinib + [E2:E2] <-> [Lapatinib:E2:E2] | kfLapatinib_4 | krLapatinib_2 |
| Lapatinib_v7 | Lapatinib + [E2:E3] <-> [Lapatinib:E2:E3] | kfLapatinib_2 | krLapatinib_2 |
| Lapatinib_v8 | Lapatinib + [Lapatinib:E1:E1] <-> [Lapatinib:E1:E1:Lapatinib] | kfLapatinib_1 | krLapatinib_1 |
| Lapatinib_v9 | Lapatinib + [Lapatinib:E1:E2] <-> [Lapatinib:E1:E2:Lapatinib] | kfLapatinib_1 | krLapatinib_1 |
| Lapatinib_v10 | Lapatinib + [Lapatinib:E2:E2] <-> [Lapatinib:E2:E2:Lapatinib] | kfLapatinib_2 | krLapatinib_2 |
| Lapatinib_v11 | Lapatinib + [BTC:E1] <-> [Lapatinib:BTC:E1] | kfLapatinib_1 | krLapatinib_1 |
| Lapatinib_v12 | Lapatinib [TC:E1:E1] <-> [Lapatinib:B TC:E1:E1] | kfLapatinib_3 | krLapatinib_1 |
| Lapatinib_v13 | Lapatinib + [BTC:E1:E1:BTC] <-> [Lapatinib:BTC:E1:E1:BTC] | kfLapatinib_3 | krLapatinib_1 |
| Lapatinib_v14 | Lapatinib + [BTC:E1:E2] <-> [Lapatinib:BTC:E1:E2] | kfLapatinib_3 | krLapatinib_1 |
| Lapatinib_v15 | Lapatinib + [BTC:E1:E3] <-> [Lapatinib:BTC:E1:E3] | kfLapatinib_1 | krLapatinib_1 |
| Lapatinib_v16 | Lapatinib + [E2:E3:HRG] <-> [Lapatinib:E2:E3:HRG] | kfLapatinib_2 | krLapatinib_2 |
| Lapatinib_v17 | Lapatinib + [E1:E3:HRG] <-> [Lapatinib:E1:E3:HRG] | kfLapatinib_1 | krLapatinib_1 |
| Lapatinib_v18 | Lapatinib + [Lapatinib:BTC:E1:E1] <-> [Lapatinib:BTC:E1:E1:Lapatinib] | kfLapatinib_1 | krLapatinib_1 |
| Lapatinib_v19 | Lapatinib + [Lapatinib:BTC:E1:E1:BTC] <-> [Lapatinib:BTC:E1:E1:BTC:Lapatinib] | kfLapatinib_1 | krLapatinib_1 |

TABLE 12-continued

Implementation scheme forAb

| Reaction Number | Reaction | Forward parameter | Reverse parameter |
|---|---|---|---|
| Lapatinib_v20 | Lapatinib + [Lapatinib:BTC:E1:E2] <-> [Lapatinib:BTC:E1:E2:Lapatinib] | kfLapatinib_1 | krLapatinib_1 |
| Lapatinib_v21 | [Lapatinib:E1] + E1 <-> [Lapatinib:E1:E1] | kf12 | kr12 |
| Lapatinib_v22 | [Lapatinib:E1] + E2 <-> [Lapatinib:E1:E2] | kf12 | kr12 |
| Lapatinib_v23 | [Lapatinib:E1] + E3 <-> [Lapatinib:E1:E3] | kf12 | kr12 |
| Lapatinib_v24 | [Lapatinib:E2] + E1 <-> [Lapatinib:E1:E2] | kf12 | kr12 |
| Lapatinib_v25 | [Lapatinib:E2] + E3 <-> [Lapatinib:E2:E3] | kf12 | kr12 |
| Lapatinib_v26 | [Lapatinib:E1] + [Lapatinib:E1] <-> [Lapatinib:E1:E1:Lapatinib] | kf12 | kr12 |
| Lapatinib_v27 | [Lapatinib:E1] + [Lapatinib:E2] <-> [Lapatinib:E1:E2:Lapatinib] | kf12 | kr12 |
| Lapatinib_v28 | [Lapatinib:E2] + [Lapatinib:E2] <-> [Lapatinib:E2:E2:Lapatinib] | kf12 | kr12 |
| Lapatinib_v29 | [Lapatinib:BTC:E1] + E1 <-> [Lapatinib:BTC:E1:E1] | kf14 | kr14 |
| Lapatinib_v30 | [Lapatinib:BTC:E1] + E2 <-> [Lapatinib:BTC:E1:E2] | kf19 | kr19 |
| Lapatinib_v31 | [Lapatinib:BTC:E1] + E3 <-> [Lapatinib:BTC:E1:E3] | kf23 | kr19 |
| Lapatinib_v32 | [Lapatinib:BTC:E1] + [BTC:E1] <-> [Lapatinib:BTC:E1:E1:BTC] | kf16 | kr16 |
| Lapatinib_v33 | [Lapatinib:BTC:E1] + [Lapatinib:BTC:E1] <-> [Lapatinib:BTC:E1:E1:BTC:Lapatinib] | kf16 | kr16 |
| Lapatinib_v34 | [Lapatinib:BTC:E1] + [Lapatinib:E2] <-> [Lapatinib:BTC:E1:E2:Lapatinib] | kf19 | kr19 |
| Lapatinib_v35 | [Lapatinib:E2] + [HRG:E3] <-> [Lapatinib:E2:E3:HRG] | kf7 | kr7 |
| Lapatinib_v36 | [Lapatinib:E1] + [HRG:E3] <-> [Lapatinib:E1:E3:HRG] | kf10 | kr7 |
| Lapatinib_v37 | [Lapatinib:E1] + BTC <-> [Lapatinib:BTC:E1] | kf3 | kr3 |
| Lapatinib_v38 | [Lapatinib:E1:E1] + BTC <-> [Lapatinib:BTC:E1:E1] | kf4 | kr3 |
| Lapatinib_v39 | [Lapatinib:E1:E2] + BTC <-> [Lapatinib:BTC:E1:E2] | kf5 | kr3 |
| Lapatinib_v40 | [Lapatinib:E1:E3] + BTC <-> [Lapatinib:BTC:E1:E3] | kf5 | kr3 |
| Lapatinib_v41 | [Lapatinib:BTC:E1:E1] + BTC <-> [Lapatinib:BTC:E1:E1:BTC] | kf4 | kr4 |
| Lapatinib_v42 | [Lapatinib:E2:E3] + HRG <-> [Lapatinib:E2:E3:HRG] | kf2 | kr1 |

TABLE 13

Inhibitor parameter values.

| Name | Value | Units | Description |
|---|---|---|---|
| Vcell | 1.0E−12 | Liters | Cell volume. |
| Vshell | 4.8E−15 | Liters | Reduced volume Vshell for $2^{nd}$ arm of IgG binding. Vshell = 4/3*pi*((Cell_radius + Cell_shellheight)^3 − cell_radius) Cell radius (Vcell*3/(4*pi()))^(1/3) in decimeters. Cell_shellheight = 1e−7 decimeters. Cell_shellhight represents the average distance between antibody binding sites. |
| MM-121 parameters | | | |
| kf Ab #6 _1 | 7.15E−11 | molecules$^{-1}$ sec$^{-1}$ | Ab #6 inhibitor binding to ErbB3. Unit conversion calculated as 1.43e5M$^{-1}$s$^{-1}$/(Vmedia*Av/Num_cells). Num_cells = 30,000 per well. |
| kr Ab #6 _1 | 1.10E−04 | sec$^{-1}$ | Ab #6 inhibitor dissociation from ErbB3 |
| kf Ab #6 _2 | 4.96E−05 | molecules$^{-1}$ sec$^{-1}$ | Ab #6 inhibitor binding to a second ErbB3. Avidity due to volume reduction = kr Ab #6 _1* (Vmedia/Numcells)/Vshell. |
| kr Ab #6 _2 | 2.20E−04 | sec$^{-1}$ | Ab #6 inhibitor dissociation from a second ErbB3 (2*krmm121_1) |

TABLE 13-continued

Inhibitor parameter values.

| Name | Value | Units | Description |
|---|---|---|---|
| kf Ab #6 _3 | 5.56E−04 | sec$^{-1}$ | Internalization rate for Ab #6 bound to two ErbB3 molecules |
| kr Ab #6 _3 | 5.00E−03 | sec$^{-1}$ | Recycling rate for Ab #6 bound to two ErbB3 molecules |
| kf Ab #6 _4 | 2.00E−04 | sec$^{-1}$ | Degradation of Ab #6 bound species |
| Cetuximab parameters | | | |
| kfCetuximab_1 | 1.10E−10 | molecules$^{-1}$ sec$^{-1}$ | Cetuximab inhibitor binding to ErbB1. Unit conversion calculated as 2.2e5M$^{-1}$s$^{-1}$/ (Vmedia*Av/Num_cells). |
| krCetuximab_1 | 1.10E−03 | sec$^{-1}$ | Cetuximab inhibitor dissociation from ErbB1 |
| kfCetuximab2 | 7.64E−05 | molecules$^{-1}$ sec$^{-1}$ | Cetuximab inhibitor binding to a second ErbB1. Avidity due to volume reduction = krCetuximab_1*(Vmedia/Numcells)/Vshell. |
| krCetuximab_2 | 2.20E−03 | sec$^{-1}$ | Cetuximab inhibitor dissociation when bound to two ErbB1 molecules (2*krcetuximab_1) |
| Pertuzumab parameters | | | |
| kfPertuzumab_1 | 5.60E−11 | molecules$^{-1}$ sec$^{-1}$ | Pertuzumab inhibitor binding to ErbB2. Unit conversion calculated as 1.12e5M$^{-1}$s$^{-1}$/ (Vmedia*Av/Num_cells). |
| krPertuzumab_1 | 9.50E−04 | sec$^{-1}$ | Pertuzumab inhibitor dissociation from ErbB2 |
| kfPertuzumab_2 | 3.90E−05 | molecules$^{-1}$ sec$^{-1}$ | Pertuzumab inhibitor binding to a second ErbB2. Avidity due to volume reduction = krPertuzumab_1*(Vmedia/Numcells)/Vshell. |
| krPertuzumab_2 | 1.90E−03 | sec$^{-1}$ | Pertuzumab inhibitor dissociation from a second ErbB2 (2*krpertuzumab_1). |
| Lapatinib parameters | | | |
| kfLapatinib-1 | 6.40E−12 | molecules$^{-1}$ sec$^{-1}$ | Lapatinib inhibitor binding to ErbB1 or 1-3 dimers. Unit conversion calculated as 1.28e4M$^{-1}$s$^{-1}$/ (Vmedia*Av/Num_cells). |
| krLapatinib_1 | 3.83E−05 | sec$^{-1}$ | Lapatinib inhibitor dissociation from ErbB1 or 1-3 dimers. |
| kfLapatinib_2 | 1.50E−12 | molecules$^{-1}$ sec$^{-1}$ | Lapatinib inhibitor binding from ErbB2 or 2-3 dimers. Unit conversion calculated as 2.95e3M$^{-1}$s$^{-1}$/ (Vmedia*Av/Num_cells). |
| krLapatinib_2 | 3.83E−05 | sec$^{-1}$ | Lapatinib inhibitor dissociation to ErbB2 or 2-3 dimers. |
| kfLapatinib_3 | 1.28E−11 | molecules$^{-1}$ sec$^{-1}$ | Lapatinib inhibitor binding to 1-1 or 1-2 dimers |
| kfLapatinib_4 | 3.00E−12 | molecules$^{-1}$ sec$^{-1}$ | Lapatinib inhibitor binding to 2-2 dimers |

Example 5

Selection of Markers Predictive of Activation of pErbB3

In this example, a set of protein markers that are predictive for activation of ErbB3, as indicated by pErbB3, were identified using the mechanistic computational model of the ErbB signaling pathway that was described in Example 4.

As the level of ErbB3 phosphorylation was demonstrated in Example 2 to correlate with tumor response rate, a sensitivity analysis was conducted on the trained computational model to identify the key proteins that determine the level of ErbB3 phosphorylation.

In this local sensitivity analysis, cells were virtually stimulated in silico with 0.4 nM of either HRG or BTC, both of which are ligands that activate the ErbB signaling pathway. The sensitivity of pErbB3 with respect to the following cellular receptors, kinases and other proteins was determined: ErbB3, ErbB2, ErbB1, PI3K, PIP2, PTEN, PDK1, PP2A, AKT, RTKpase and the ligands (BTC and HRG).

The local sensitivity analysis is a mathematical tool that measures changes in an output in response to changes in protein concentrations and kinetic parameters within the pathway. The fully normalized sensitivity ($s_{ij}(t)$) of the $i^{th}$ observable $c_i(t)$ with respect to a change in the $j^{th}$ rate constant ($k_j$) is given by the following equation:

$$s_{ij}(t) \equiv \frac{\partial \ln(c_i(t))}{\partial \ln(k_j)} \quad \text{(Eqn. 2)}$$

Model calibration was then performed using local and global optimization methods (Genetic Algorithms, simulated annealing, Levenberg-Marquardt optimization) that minimized the distance between the experimental data and the simulation results by varying the parameters and initial protein concentrations identified in the sensitivity analysis.

Figure 6:
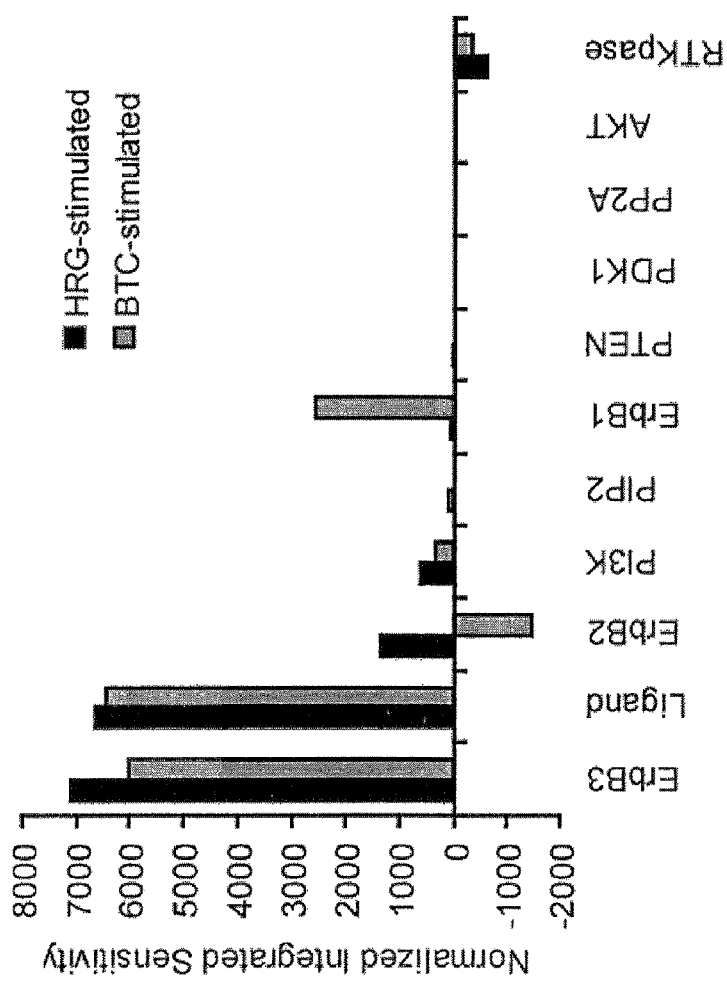
FIG. 6 is a bar graph showing the results of the local sensitivity analysis to identify key markers for activation of ErbB3.

The results of the local sensitivity analysis are summarized in the bar graph of FIG. 6. The results indicated that the following five proteins are the key set of markers that are predictive for activation of ErbB3 (e.g., formation of pErbB3): ErbB1, ErbB2, ErbB3, HRG and BTC.

Example 6

Use of a Mechanistic Computational Model to Compute pErbB3 Levels

Based on the results obtained in Example 5, in which ErbB1, ErbB2, ErbB3, HRG and BTC were identified as the key markers for prediction of pErbB3 using the computational model, the measurements of the protein expression levels depicted in Table 2 were used as inputs into the computational model to compute pErbB3 levels for different tumor cell lines.

Input of BTC and HRG expression levels into the computational model required conversion from dimensionless units or pg/μg into a concentration [M]. Thus, conversion factors needed to be established. The conversion factors that converted HRG mRNA levels and BTC protein expression levels into a molar concentration were extrapolated in the linear range between experimentally measured and predicted pErbB3 levels. For the experimentally measured values, the constitutive ErbB3 phosphorylation levels (pg/μg) were measured in the four cell lines (MALME3M, DU145, ADRr and ACHN) in 10% fetal bovine serum (FBS). These experimentally measured results are shown in Example 4 in Table 2, column 7. For ligand conversion factor training, the normalized predicted pErbB3 signal integrated over time was plotted versus the experimentally measured pErbB3 in 10% FBS in vitro, using a BTC conversion factor of 6.1e-005 and a HRG mRNA conversion factor of 3.1e-013. The ligand conversion factors were trained by optimizing the linear relationship between predicted pErbB3 and measured constitutive pErbB3 levels (by ELISA) in the cell lines ADRr, MALME3M, ACHN and DU145.

Figure 7:
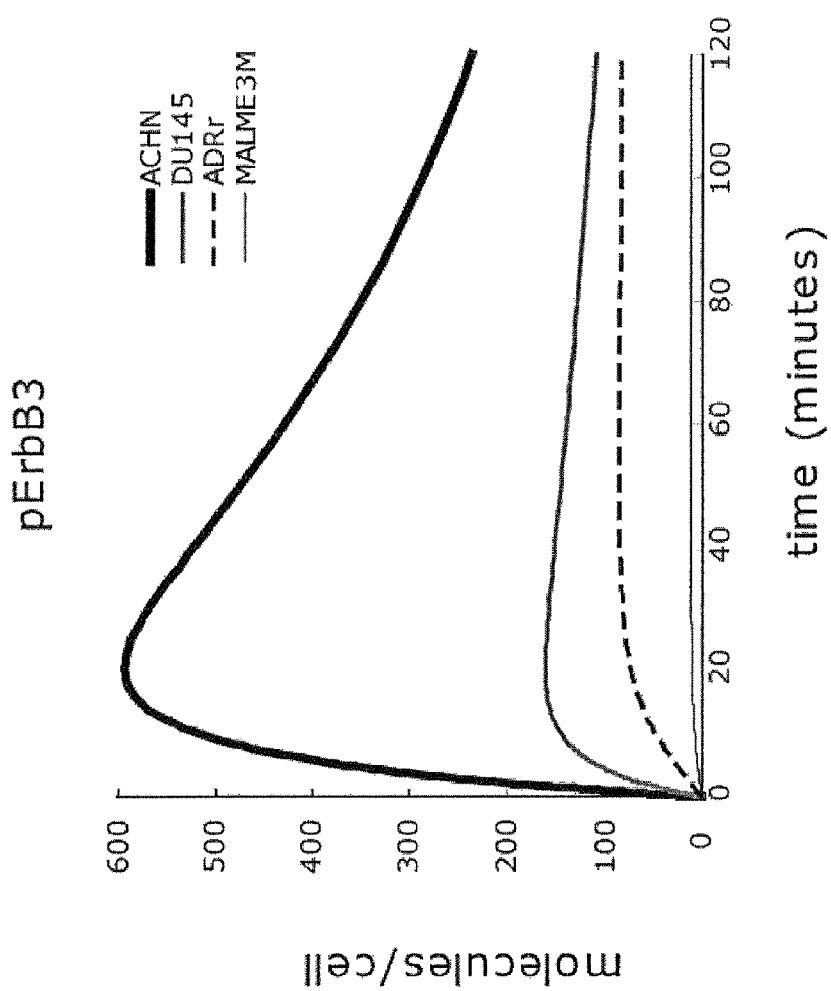
FIG. 7 is a graph showing the computed levels of pErbB3 in the MALME3M, DU145, ADRr and ACHN cell lines.

Thus, the activation of the pathway by HRG and BTC was simulated using the model and the Network Activation State (NAS), as indicated by computed pErbB3 levels, was obtained as the output. In this case, the NAS was defined as the amount of time-integrated pErbB3 simulated in the model over the first two hours of stimulation by HRG and BTC. The results for the computed pErbB3 levels are shown in the graph of FIG. 7. The simulated NAS for ADRr cells was initially set as the threshold between responder and non-responder to Ab #6 treatment, since of the four cell lines tested in the xenograft models, the ADRr cell line was a non-responder with the highest pErbB3 level.

Example 7

Setting NAS Threshold Values Using Xenograft Responses and Predicting Responsiveness Based on NAS Thresholds In this example, the xenograft responses for the four tumor cell lines described in Example 1 were combined with the NAS values (normalized, time-integrated pErbB3 levels) computed as described in Example 6 to set NAS threshold values for responders to Ab #6 treatment and non-responders to Ab #6 treatment.

More specifically, the growth rate reduction (GRR) values determined for the ADRr, ACHN, DU145 and MALME3 cell lines (described further in Example 1) were converted to a binary outcome for stratification training by setting "responders" as having a pErbB3 level that is greater than the level of pErbB3 in ADRr cells (i.e., a pErbB3>pErbB3(ADRr)), wherein "non-responders" were set as having a pErbB3 level that is less than the level of pErbB3 in ADRr cells (i.e., a pErbB3<pErbB3(ADRr)). It should be noted that this was not a model prediction; rather, this was part of the stratification training process.

For the four cell lines, the experimentally determined GRR values were plotted against the computed NAS values (normalized, time-integrated pErbB3). The GRR values, on the x-axis, were divided into the responders (pErbB3>pErbB3(ADRr)) and the non-responders (pErbB3<pErbB3(ADRr)).

The NAS training data (obtained as described in Example 4) allowed for division of the Network Activation State y-axis into three categories: Simulated Responder ("Sim R"), Simulated Non-Responder ("Sim NR") and Simulated Indeterminate ("Sim I"). Two xenograft cell lines were characterized by Growth Rate Reduction values of more than 20% (DU145, ACHN) and of these, the DU145 cell line had the lowest Network Activation State. Consequently, the threshold for classifying a cell line as a Simulated Responder was set at a Network Activation State greater than or equal to the ADRr level. Similarly, the MALME3 cell line xenograft was a non-responder (pErbB3<pErbB3(ADRr)) and, therefore, Network Activation States of cell lines that are lower than the ADRr level were classified as Simulated Non-Responders. Network Activation States between these the ADRr and DU145 thresholds are classified as Simulated Indeterminate.

Figure 8:
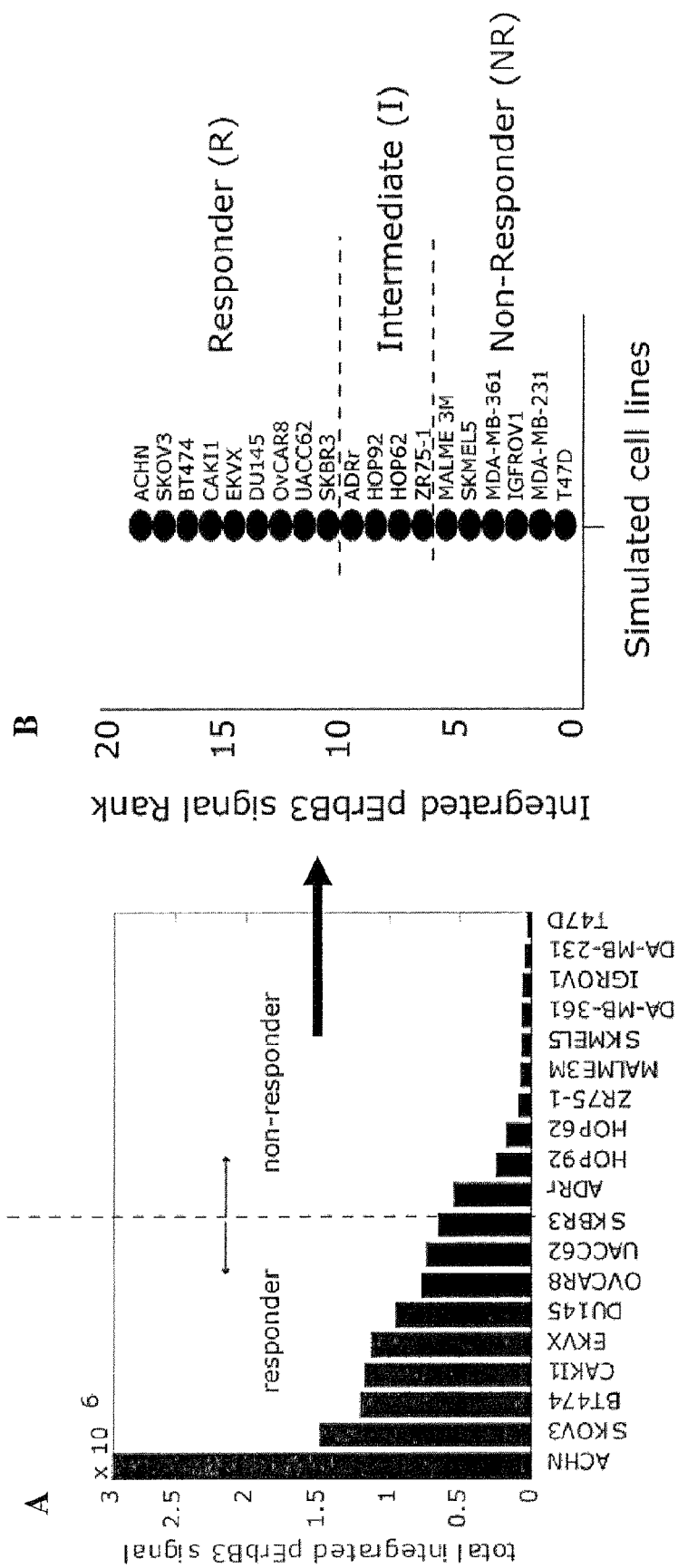
FIGS. 8A-8B are graphs showing use of NAS values to predict responsiveness of 15 cell lines to Ab #6 treatment, based on threshold NAS values established from the 4 training cell lines (MALME3M, DU145, ADRr and ACHN).

The Network Activation State, as indicated by computed pErbB3 levels, was simulated for a panel of 15 cell lines for which experimental measurements of HRG, BTC, ErbB1, ErbB2 and ErbB3 were available. The integrated pErbB3 levels computed for the cells were plotted, along with the levels for the 4 training cell lines, in the bar graph shown in FIG. 8A, from highest to lowest pErbB3 levels. The computed NAS values for these 15 cell lines were then ranked against the NAS values previously determined for the four training cell lines ADRr, ACHN, DU145 and MALME3M. The NAS results for the 19 cell lines in total are ranked as shown in the graph of FIG. 8B. NAS values equal to or below that of the MALME3M cell line were set as simulated non-responders ("Sim NR"), NAS values between those of the MALME3M and DU145 cell lines were set as simulated indeterminate ("Sim I") and NAS values equal to or above that of the DU145 cell line were set as simulated responders ("Sim R"). Thus, as illustrated in FIG. 8B, the IGROV1 (NCI-60, cosmic sample ID No. 905968), MDA-MB-361 (ATCC No. HTB-27), SKMEL-5 (ATCC No. HTB-70), MDA-MB-231 (ATCC No. HTB-26) and T47D (ATCC No. HTB-133) cell lines were predicted to be simulated non-responders, since their computed NAS values were below those of MALME3M. Moreover, the ZR75-1 (ATCC No. CRL-1500), HOP92 (NCI-60, cosmic sample ID No. 905973) and HOP62 (NCI-60, cosmic sample ID No. 905972) cell lines were predicted to be simulated indeterminate, since their computed NAS values were between those of ADRr and DU145. Finally, the SKBR3 (ATCC No. HTB-30), UACC62 (NCI-60, cosmic sample ID No. 905976), EKVX (NCI-60, cosmic sample ID No. 905970), BT474 (ATCC No. HTB-20), SKOV3 (ATCC No. HTB-77), OVCAR8 (obtained from the National Cancer Institute, Division of Cancer Treatment and Diagnostics) and CAK11 (NCI-60, cosmic sample ID No. 905963) cell lines were predicted to be simulated responders, since their computed NAS values were higher than that of ADRr.

Figure 9:
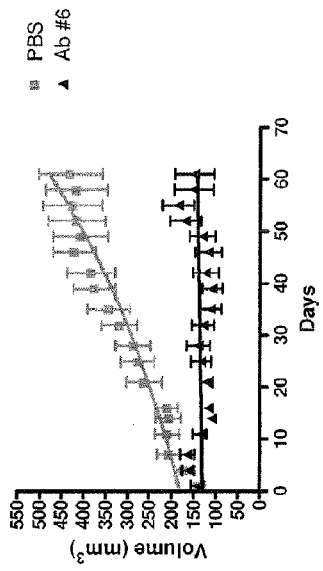
FIGS. 9A-9C are graphs showing the inhibition of xenograft tumor growth by treatment with the Ab #6 antibody.
Figure 9:
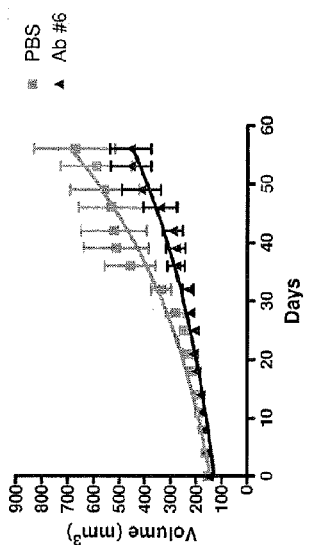
Figure 9:
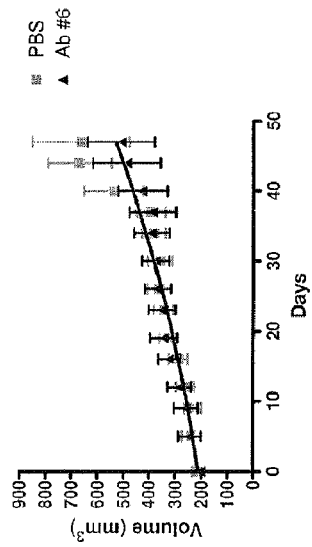
Figure 10:
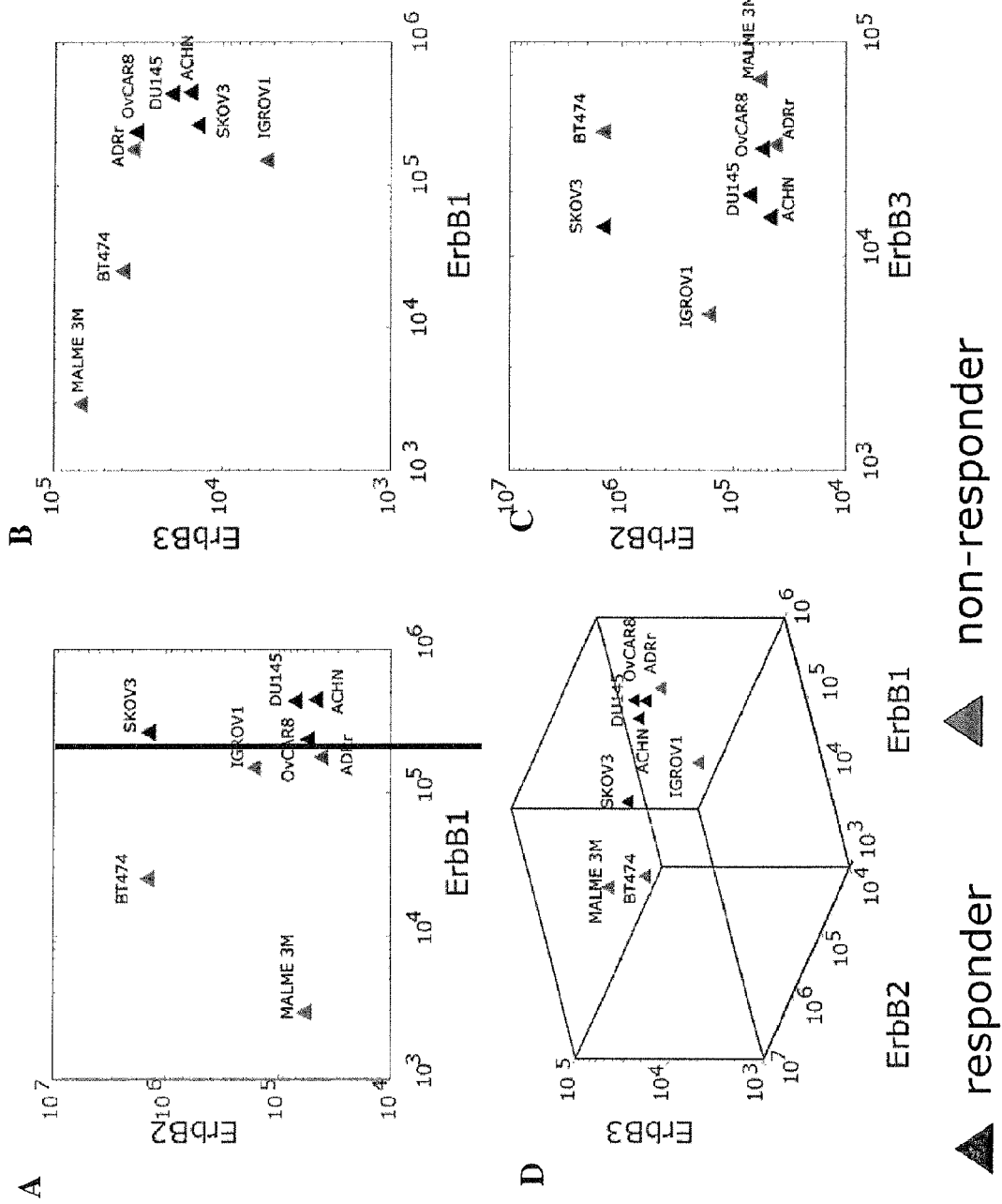
FIGS. 10A-10D are graphs in which the log of the concentration of one ErbB receptor is plotted against the log of the concentration of one or more of the other ErbB receptors. Receptor values are shown for cell lines classified as Ab #6 responders or non-responders.

To test these model predictions, three additional in vivo xenograft studies were performed. The IGROV1, OVCAR8 and SKOV3 cell lines were used in xenograft studies conducted as described in Example 1, wherein mice were treated with 600 μg of Ab #6 every 3 days or with PBS as a control. The xenograft responses, as determined by changes in tumor volume (in mm$^3$) over time, are summarized in the graphs of FIGS. 9A-9C. Again, the Growth Rate Reduction (GRR) value for each cell line was calculated using the following formula:

Growth Rate Reduction=1−(Ab #6 Growth Rate)/(PBS Growth Rate)

The GRR values for the four cell lines tested are summarized in Table 14 below:

TABLE 14

Summary of Tumor Growth Rate Reduction for Predicted Set of Xenograft Studies

| Cell Line | GRR [%] |
|---|---|
| IGROV1 | 6.3 |
| OVCAR8 | 91.4 |
| SKOV3 | 19.6 |

Regarding the prediction of Ab #6 responsiveness for each cell line, based on the criteria that a xenograft responder must have a simulated pErbB3 level greater than the simulated pErbB3 for ADRr, the IGROV1 xenograft was categorized as a non-responder, whereas the OVCAR8 and SKOV3 xenografts were categorized as responders.

These data demonstrate that the predictions made based on the computed NAS values precisely corresponded to the experimentally observed responsiveness of the three test cell lines to Ab #6 treatment in vivo in the xenograft studies. More specifically, the IGROV1 cell line was predicted to be a simulated non-responder based on its computed NAS value, and was experimentally observed to be a non-responder based on its GRR value. Similarly, the OVCAR8, and SKOV3 cell lines were predicted to be simulated responders based on their computed NAS values, and were experimentally observed to be responders based on their GRR values.

Accordingly, these experiments confirmed the effectiveness of the computational model, and the computed NAS value of normalized time-integrated pErbB3 levels, as being predictive of responsiveness to Ab #6 treatment in vivo.

Example 8

Identification of Direct Biomarkers for Ab #6 Responsiveness

In this example, the data obtained for the four cell lines examined in the xenograft studies described in Example 1 (ADRr, ACHN, DU154 and MALME3M) and the three cell lines examined in the xenograft studies described in Example 7 (IGROV1, OVCAR8 and SKOV3) were further examined to determine whether direct biomarkers for Ab #6 responsiveness could be identified.

First, it was examined whether the receptor concentrations for ErbB1, ErbB2 and ErbB3 effectively classified the xenograft data into responders and non-responders. As illustrated in the graphs of FIGS. 10A-10D (in which the log of the concentration of one receptor is plotted against the log of the concentration of one or more of the other receptors), only ErbB1 receptor measurements appeared to classify the xenograft data into responders and non-responders, while none of the other receptors did so.

Figure 11:
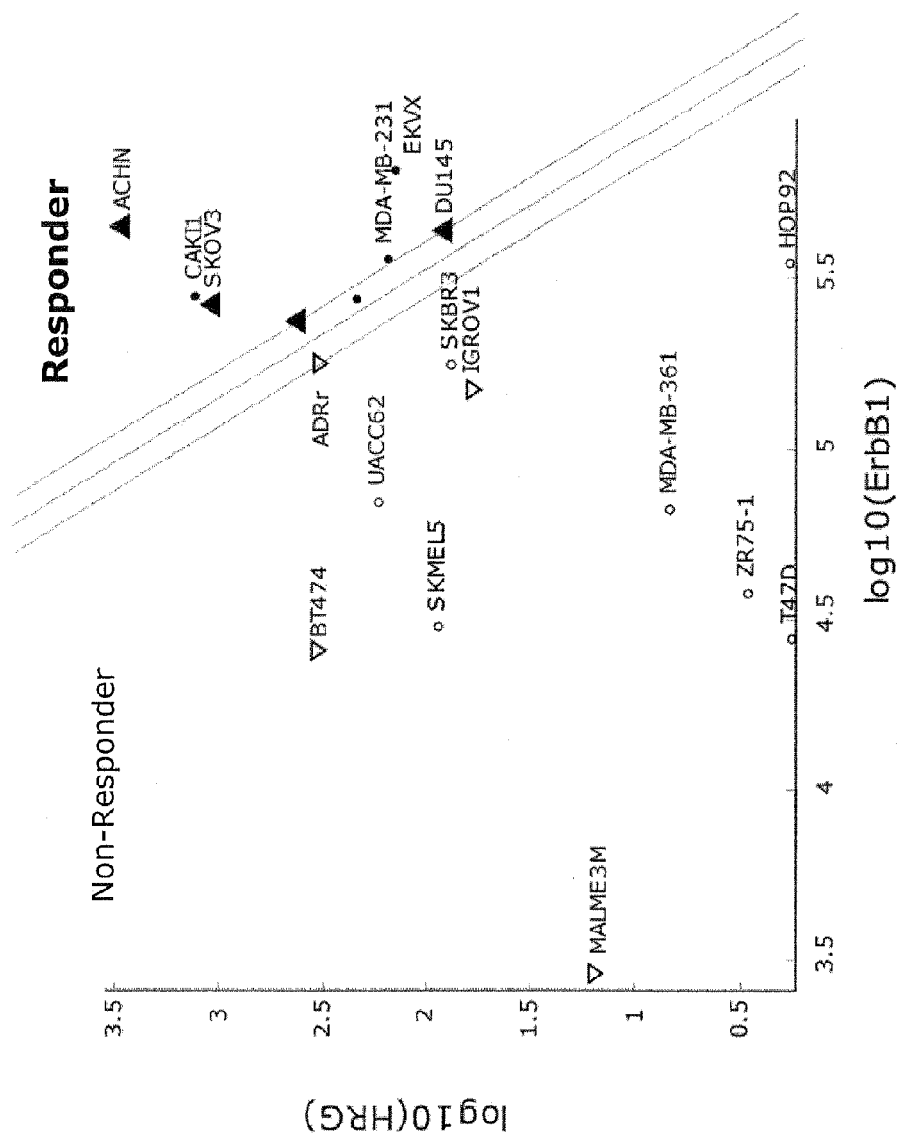
FIG. 11 shows a graph in which the log concentration of HRG is plotted against the log concentration of ErbB1. In the graph, responding vs. non-responding cell lines tested in xenograft studies segregate.

Next, it was examined whether the concentration of HRG in combination with one receptor concentration (e.g., ErbB1, ErbB3) effectively classified the xenograft data into responders and non-responders. As illustrated in the graph of FIG. 11 (in which the log of the concentration of HRG is plotted against the log of the concentration of ErbB1), these two concentration measurements, HRG and one of the ErbB receptors, were able to accurately classify the xenograft data into responders and non-responders. More specifically, the data for the three non-responders MALME3, ADRr and IGROV1, was separable from the data for the six responders, thereby allowing for classification of non-responders versus responders.

Accordingly, direct biomarkers for Ab #6 responsiveness were identified as HRG in combination with one of the ErbB pathway receptors (e.g., ErbB1, ErbB3).

Table 15 below summarizes the predicted responders and non-responders for the cell lines studied in Example 7 using the direct biomarkers for Ab #6 to make the predictions. The prediction determined using the direct biomarkers corresponded well with the predictions determined using the NAS values (as described in Example 7). For example, the ACHN, DU145, OVCAR8 and SKOV3 cell lines previously had been identified as responders using the NAS values and were also predicted to be responders using the direct biomarkers. Similarly, the ADRr, MALME3M and IGROV1 cell lines previously had been identified as non-responders using the NAS values and were also predicted to be non-responders using the direct biomarkers.

TABLE 15

Predicted Responders and Non-responders using the Direct Biomarkers for Ab #6

| Responders | In between | Non-Responders |
|---|---|---|
| ACHN | SKBR3 | ADRr |
| CAKI1 | | BT474 |
| DU145 | | HOP92 |
| EKVX | | IGROV1 |
| HOP62 | | MALME3M |
| MDA-MB-231 | | MDA-MB-361 |
| OVCAR8 | | SKMEL5 |
| SKOV3 | | T47D |
| | | UACC62 |
| | | ZR75-1 |

Comparing the results from Example 7 using the NAS to segregate between responders and non-responders with the results from Example 8 using the direct biomarkers for the segregation, the only discrepancies were for the BT474, MDA-MB-231 and UACC62 cell lines. It is not surprising that there are some differences between these two distinct methods of classification. In this situation, the disputed cell lines are considered responders since, in the context in patient stratification, false positives are preferable to false negatives.

Example 9

Comparison of Protein Expression Levels Between Xenografts and Human Tumors by ELISA and qIHC In this example, the similarity or differences in the protein expression profiles observed in xenografts compared to protein expression profiles observed in human tumors were assessed. This was done to determine whether the protein levels observed in the xenografts were comparable to the protein levels observed in human tumors.

Figure 12:
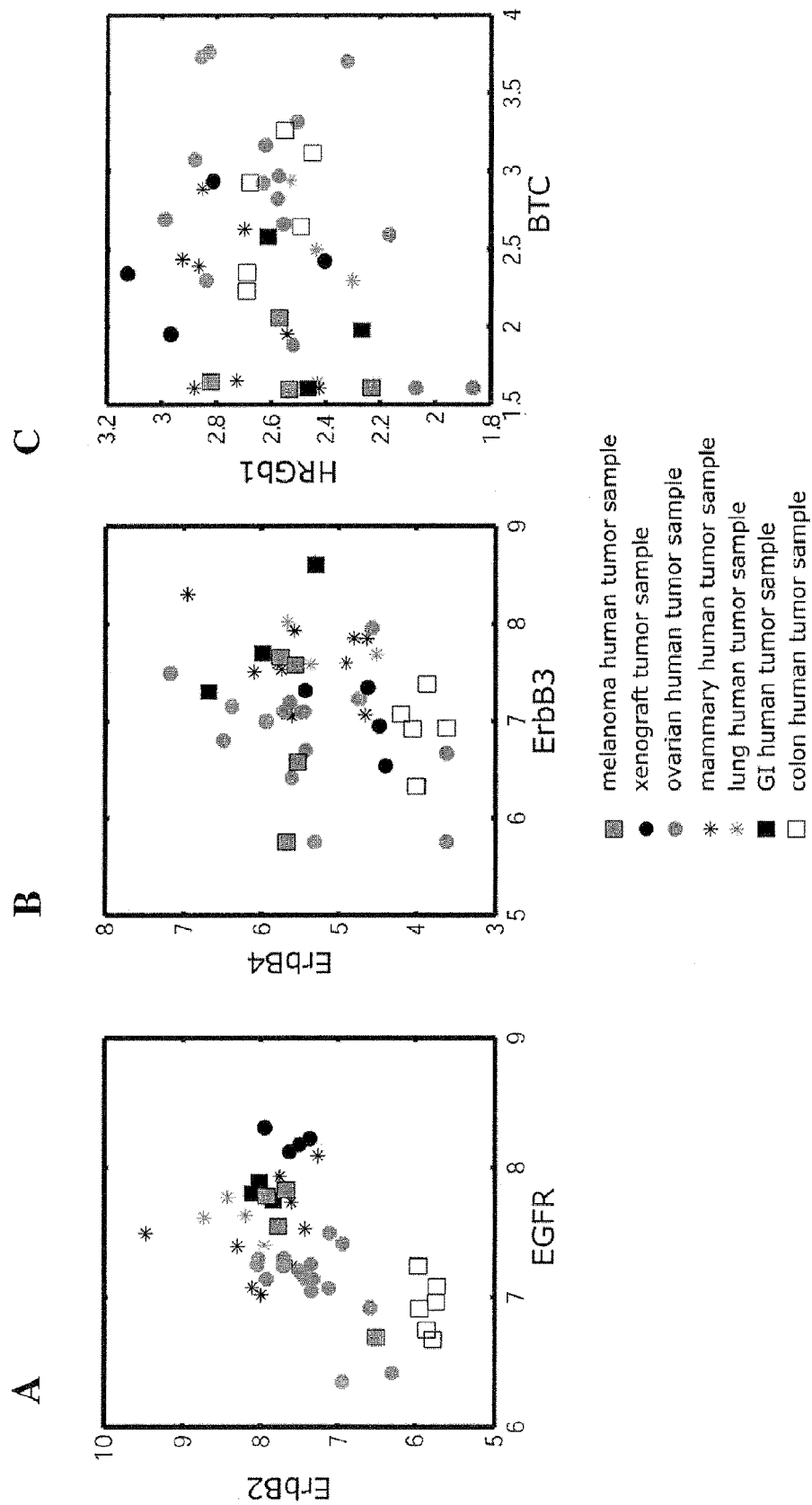
FIGS. 12A-12C are graphs in which the log normalized expression levels (in pg/µg, determined by ELISA) of different components of the ErbB signaling pathway in xenograft cell lines and human tumor samples are plotted.

In a first set of experiments, protein expression levels are measured by ELISA. Lysates are prepared from snap frozen tumors from human tumor samples or from xenografts, substantially as described in detail in Example 2, and are analyzed by ELISA for protein levels for ErbB1-4, HRG-β1 and BTC, also as substantially described in Example 2. The results (obtained using the methods described above or minor variations thereof) are plotted in the graphs of FIGS. 12A-12C. The results demonstrate that the values obtained for the protein levels in the xenograft samples are largely interspersed with the values obtained for the protein levels in the human tumor samples from different tissue origin, indicating that the protein levels observed in the xenografts are comparable to the protein levels observed in human tumors. Based on these data, it is asserted that the NAS thresholds determined for the prediction of responsiveness in xenografts can be applied to predict responders using human tumor tissue samples.

Figure 13:
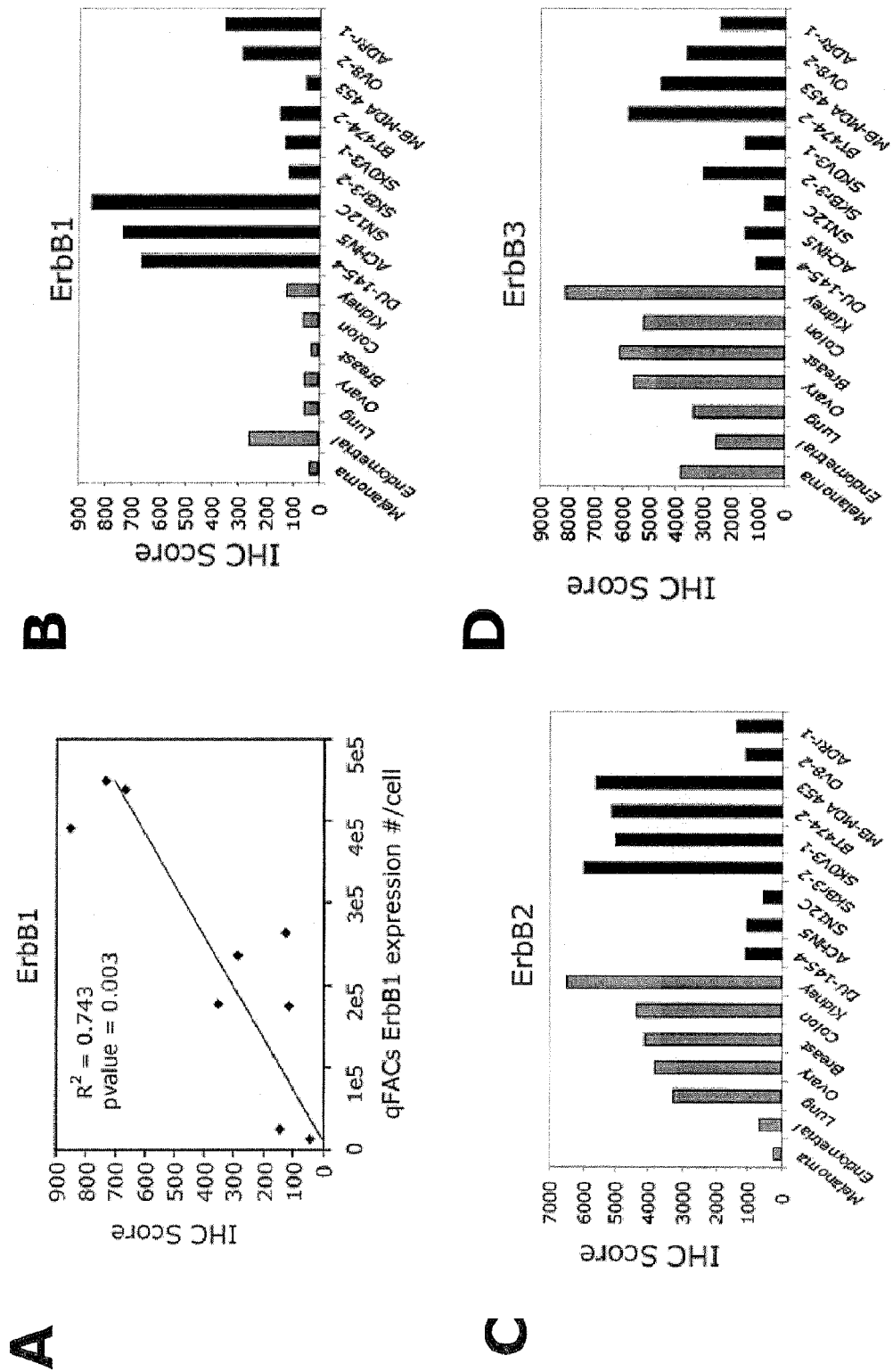
FIGS. 13A-13D are graphs showing quantitative immunohistochemistry (qIHC) results for xenograft cell lines and human tumor samples.

As frozen tissue samples can be difficult to obtain in a clinical setting, a second set of experiments were performed using measurement techniques that allow for protein quantitation in Formalin Fixed and Paraffin Embedded (FFPE) samples. More specifically, quantitative immunohistochemistry (qIHC) was performed using the AQUA® system (HistoRx, Inc., New Haven, Conn.). Using immunofluorescence and a cell line panel with representative protein expression levels, a cell line standard curve was prepared. The cell line standard curve then allowed for back-calculation of protein expression level in tumor samples and xenografts. The results are shown in FIGS. 13A-13D. FIG. 13A shows a cell line standard curve for ErbB1. FIGS. 13B, 13C and 13D show bar graphs plotting the qIHC scores for ErbB1, ErbB2 and ErbB3, respectively, in the xenograft cell lines (red bars) and human tumor samples (blue bars). The qIHC results demonstrated the similarity in protein expression levels between the human tumor samples and the xenograft samples, which span a wide range of protein expression levels. These results again support the assertion that the NAS thresholds determined for the prediction of responsiveness in xenografts can be applied to predict responders using human tumor tissue samples.

Example 10

Correlation of Responsiveness to Phosphorylated Heterodimers

In this example, integrated levels of phosphorylated ErbB homo- and heterodimers were computed as NAS values to determine whether they correlated with responsiveness to Ab #6 treatment.

The same computational model prepared as described in Example 4 was used. This model was generated based on experimentally determined measurements for the levels of ErbB1, ErbB2, ErbB3, HRG-β1 and BTC. As discussed in Example 4, seven ErbB hetero- and homo-dimers that have been described in the literature were implemented in the model: ErbB1/1, ErbB1/2, ErbB1/3, ErbB1/4, ErbB2/2, ErbB2/3 and ErbB2/4. The majority of these dimers are activated by ligand binding but several arise through a process of "lateral signaling" (or secondary dimerization) in which dimers phosphorylated in a ligand-dependent manner dissociate into monomers that then homo- or hetero-oligomerize with either activated or unactivated monomers to create active dimers. The computational model was trained with a set experimental data that allowed for the identification of the dimers that form in the presence of HRG or BTC using the ADRr cell line.

Figure 14:
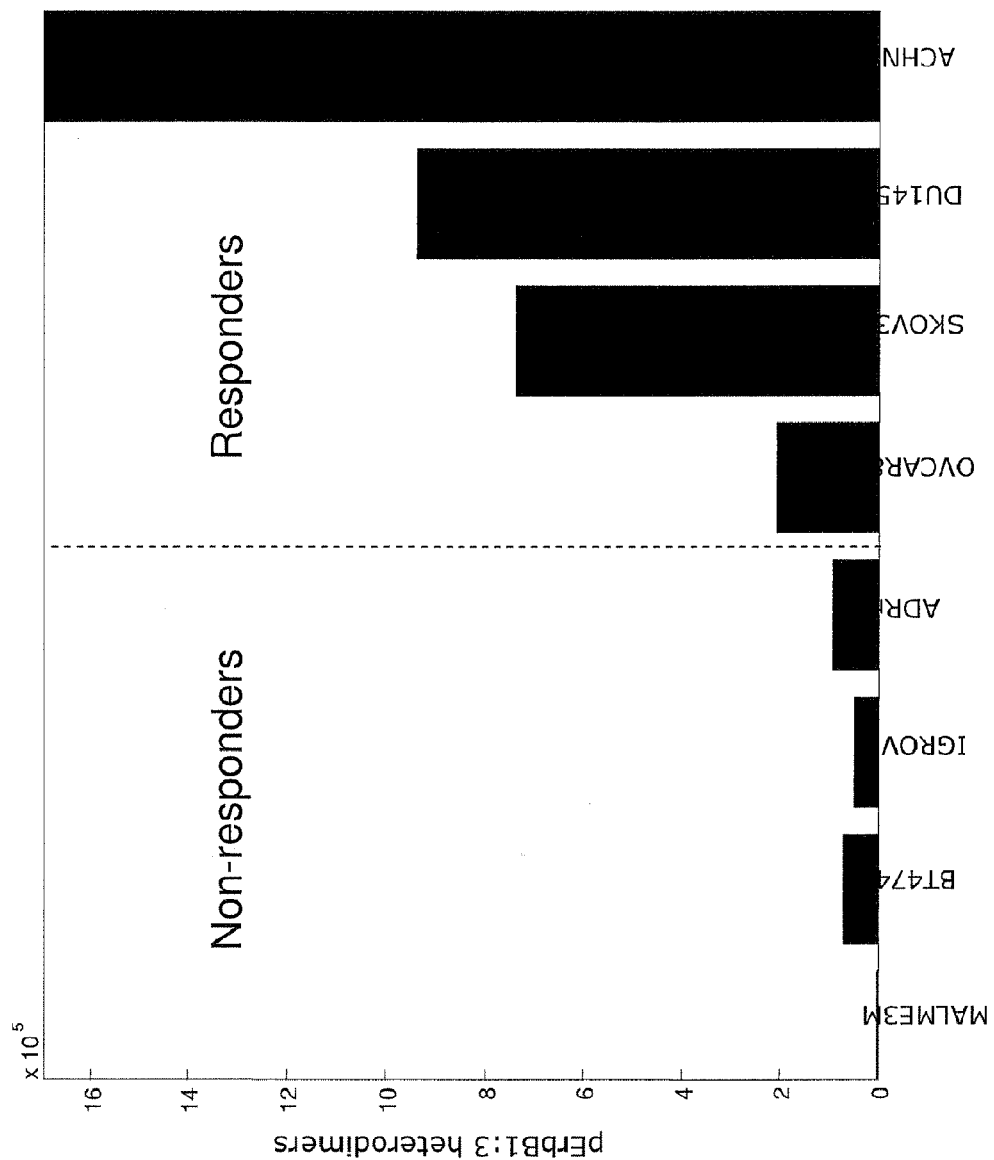
FIG. 14 is a bar graph showing the integrated phosphorylated ErbB1:3 heterodimer level (amount of time-integrated heterodimers per cell) computed for eight cell lines, which segregated them into Ab #6 non-responders (MALME3M, BT474, IGROV1 and ADRr) and responders (OVCAR8, SKOV3, DU145 and ACHN).

Thus, integrated levels of phosphorylated homo- and heterodimers were computed as a measure of the Network Activation State (NAS) for the following cell lines: MALME3M, BT474, IGROV1, ADRr, OVCAR8, SKOV3, DU145 and ACHN. As shown in the graph of FIG. 14, the computed levels of phosphorylated ErbB1/3 heterodimers (pErbB1:3) segregated the eight cell lines into Ab #6 non-responders (MALME3M, BT474, IGROV1, ADRr) and responders (OVCAR8, SKOV3, DU145 and ACHN). This segregation based on computed pErbB1:3 levels correlated identically with the predicted non-responders and responders determined using the direct biomarkers as described in Example 8. This segregation based on computed pErbB1:3 levels also correlated almost identically with the predicted non-responders and responders determined using the computed pErbB3 level for the NAS value as described in Example 7, with the only difference being for the BT474 cell line, which was identified as a non-responder using both the direct biomarkers and the computed pErbB1:3 levels but was identified as a responder using the computed pErbB3 levels.

The levels of ErbB1/1, ErbB1/2, ErbB1/3, ErbB1/4, ErbB2/2, ErbB2/3 and ErbB2/4 dimers also were computed using the computational model, but none of the levels of any of these homo- or heterodimers segregated the cell lines into responders and non-responders for Ab #6 treatment. Thus, the results observed with the ErbB1/3 heterodimers were unique among the dimers examined.

These results demonstrate that integrated levels of phosphorylated ErbB homo- or heterodimer can be used as the NAS value in the predictive methods of the invention and, more specifically, that the computed level of pErbB1:3 is a preferred NAS value for predicting responsiveness to treatment with Ab #6. These results are interpreted to mean that Ab #6 is particularly effective in cancers with high levels of ErbB1:3 heterodimers and, therefore, that direct measurement of total ErbB1:3 heterodimers or pErbB1:3 heterodimer levels also can be used as direct biomarkers for predicting the efficacy of Ab #6 treatment.

Example 11

Construction and Training of a Computational Model of the Effects of a Therapeutic Agent on the ErbB Signaling Pathway In this example, the approach described in Example 4 for constructing a mechanistic computational model was used to construct and train a model of the ErbB signaling pathway and, furthermore, to develop a computational representation of the mechanism by which a particular therapeutic agent inhibits the signaling pathway.

The therapeutic agent used in this example is the bispecific antibody H3×B1D2 (the amino acid sequence of which is shown in SEQ ID NO: 41 and which is described further in U.S. Pat. No. 7,332,585, U.S. Pat. No. 7,332,580 and PCT Application PCT/US2006/023479, published as WO 2007/084187 and PCT Application PCT/US2007/024287, published as WO 2008/140493). This bispecific antibody is composed of an anti-ErbB3 single chain antibody linked to an anti-ErbB2 single chain antibody.

The H3×B1D2 agent was predicted to preferentially target ErbB2-overexpressing tumors. Thus, a computational model of the ErbB signaling network in the presence of overexpressed ErbB2 was constructed using the methods and model described in Example 4. The model incorporated interactions between HRG and ErbB1, ErbB2, and ErbB3 receptors, leading to receptor trafficking and intracellular signaling downstream to AKT, producing phosphorylated AKT (pAKT). The included interactions were substantially identical to those found in the model of Example 4. In contrast to the model of Example 4, reactions related to the ligand BTC were not included in this model.

This model was calibrated to match experimental data for the ErbB2-overexpressing breast cell line BT474-M3 (the cell line is described in, e.g., Drummond et al. (2005) *Clin. Cancer Res.* 11:3392; Park et al. (2002) *Clin. Cancer Res.* 8:1172; Kirpotin et al. (2006) *Cancer Res.* 66:6732). Model calibration resulted in only minor differences in parameter values as compared to the model of Example 4. The most significant difference was a reduction in the rates of ErbB receptor internalization and degradation. This change is consistent with known data suggesting that ErbB2 overexpression reduces the internalization/trafficking rates of other ErbB receptors, such as ErbB1 (see e.g., Hendriks et al. (2003) *J. Biol. Chem.* 278:23343-23351; Wang et al. (1999) *Mol. Biol. Cell* 10:1621-1636; Haslekas et al. (2005) *Mol. Biol. Cell* 16:5832-5842).

For training the model, a data set was used that comprised dose-time matrices in which phosphorylation of ErbB1, ErbB2, ErbB3 and AKT at multiple time points and at six different concentrations of HRG stimulation in BT474-M3 cells was measured by ELISA.

For stimulation of the cells, the cells are seeded in duplicate wells with 1000 µl complete media at 150,000 cells per well in 12 well tissue culture plates (for 96 half well ELISA) or in duplicate plate of 100 µl complete media at 20,000 cells per well in 96 well tissue culture plates (for 384 well ELISA). These cells are incubated overnight in a humidified atmosphere of 5% $CO_2$, 95% air and 37 degrees Celsius. Cells are then switched to serum free media: RPMI-1640 media (Gibco) supplemented with, 2 mM L-glutamine (Gibco) and units/mL Pen-Strep (Gibco). Starved cells are incubated in a humidified atmosphere of 5% $CO_2$, 95% air and 37 degrees Celsius for 20-24 hours prior to stimulation. For dose-time matrix studies, cells are stimulated with ligand (HRG) at 0, 1, 2, 3, 4, 5, 7, 10, 20, 30, 60 and 120 minutes. Following stimulation with six different concentrations of HRG (0.098 nM-100 nM) for each time course, cells are placed on ice, washed with cold PBS, then lysed in 200 µl for 12 well plates and 45 µl for 96 well plates in cold M-PER Mammalian Protein Extraction Buffer (Thermo Scientific, Catalog #78501) supplemented with protease inhibitor cocktail (Sigma-Aldrich, P2714), 1 mM sodium orthovanadate (Sigma-Aldrich, S6508), 5 mM sodium pyrophosphate (Sigma-Aldrich, 221368), 50 µM oxophenylarsine (EMD Biosciences, 521000) and 10 µM bpV(phen) (EMD Biosciences, 203695).

Levels of protein phosphorylation in the stimulated cells are measured by ELISA. ErbB1, ErbB2, and ErbB3 are measured using R&D Systems Duoset IC kits (ErbB1 DYC1095-E, ErbB2 DYC1768-E, ErbB3 DYC1769-E). Capture antibodies against ErbB1 (R&D Systems, 841402), ErbB2 (R&D Systems, 841425), ErbB3 (R&D Systems, 841428) and AKT (Upstate, 05-591MG) are incubated in 96 half well plates (Greiner, Catalog #82050-046) or 384 well plates (Nunc Cat # 40518) that are black flat-bottom polystyrene high-binding plates overnight at room temperature. The ELISA plates are blocked with 2% bovine serum albumin (BSA) and phosphate buffered saline (PBS) for one hour then incubated with lysates diluted in 2% BSA, 0.1% Tween-20 and PBS for two hours at room temp. In between each incubation, the plates are washed three times with 0.05% Tween-20 in PBS. ELISAs for measuring phospho-ErbB1, -ErbB2 and -ErbB3 are incubated with Anti-Phospho-Tyrosine-HRP Detection antibody (R&D Systems, 841403) for two hours. ELISAs measuring phospho-AKT are incubated with primary serine 473 specific anti-phospho AKT mouse monoclonal antibody (Cell Signaling Technologies, Catalog #5102) for 2 hours, then incubated with Streptavidin-HRP (R&D Systems, Catalog #DY998,) for 20 minutes. All ELISAs are visualized with SuperSignal ELISA Pico Chemiluminescent Substrate (Pierce, Catalog #37069) and luminescent signal is measured using a luminometer.

Figure 21:
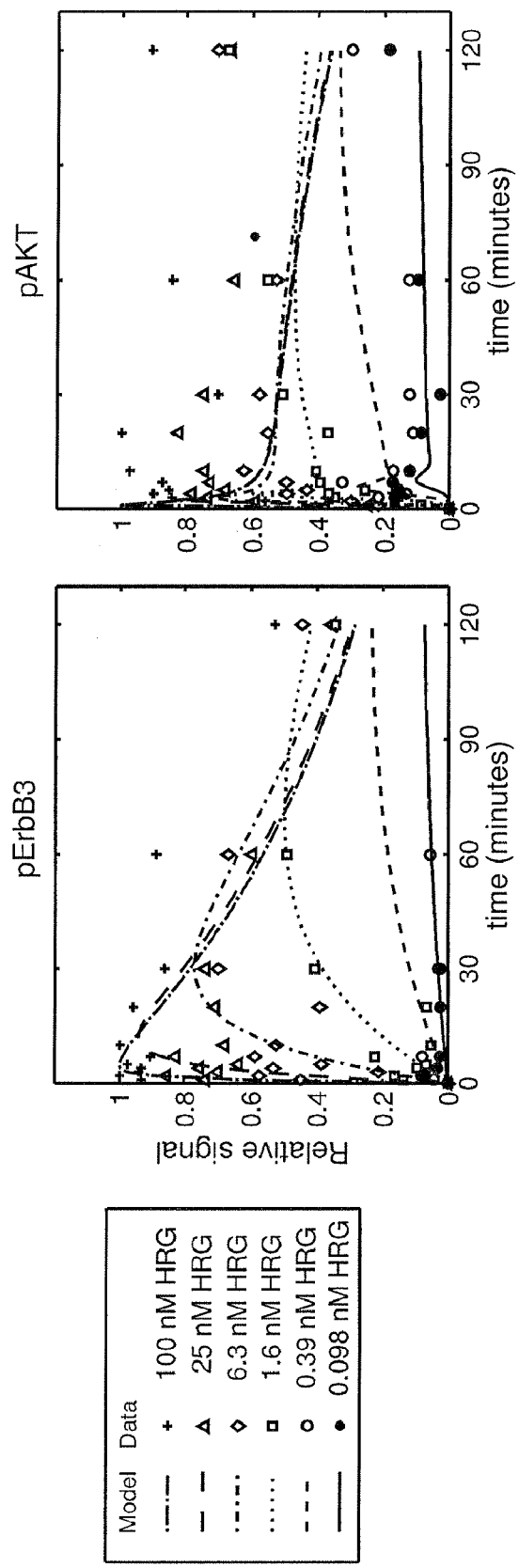
FIG. 21 provides graphic representations of predicted (plotted lines) and actual (data points) HRG-induced pErbB3 and pAKT signaling data from the ErbB2-overexpresing cell line BT474-M3 at HRG doses as indicated, as detailed in Example 11.

As shown in FIG. 21, the model matched the HRG-induced pErbB3 signaling data in the ErbB2-overexpresing cell line BT474-M3 at all doses of HRG examined experimentally. Additionally, the model matched the HRG-induced pAKT signaling data in BT474-M3 cells at HRG doses of approximately 5 nM and lower.

Next, a computational representation of the mechanism by which H3×B1D2 inhibits HRG-dependent signaling of the ErbB pathway was developed. The computational representation of the inhibitor was constructed using mass-action reaction equations that describe the binding of inhibitor to ErbB2 and ErbB3 and subsequent inhibition of HRG-induced signaling. Parameters for the binding events were obtained by a combination of direct measurement (using techniques widely known in the art) and computational training of the model to match data for the inhibition of HRG-induced pErbB3 in cells by H3×B1D2. In particular, the on-rate and off-rate for binding of the H3 single chain arm of the bispecific antibody to ErbB3 and the on-rate and off-rate for the binding of the B1D2 single chain arm of the bispecific antibody to ErbB2 were experimentally determined by standard BIACore and KinExA technology. Reactions and parameters for the computational model of H3×B1D2 appear in Tables 16a and 16b.

TABLE 16a

H3 x B1D2 implementation

| Reaction Number | Reaction | Forward parameter | Reverse parameter |
|---|---|---|---|
| H3 x B1D2_v1 | E2 + (H3 x B1D2) <-> E2:(H3 x B1D2) | h3xb1d2_kf1 | h3xb1d2_kr1 |
| H3 x B1D2_v2 | (H3 x B1D2) + E3 <-> (H3 x B1D2):E3 | h3xb1d2_kf2 | h3xb1d2_kr2 |
| H3 x B1D2_v3 | E2 + (H3 x B1D2):E3 <-> E2:(H3 x B1D2):E3 | h3xb1d2_kf3 | h3xb1d2_kr1 |
| H3 x B1D2_v4 | E2:(H3 x B1D2) + E3 <-> E2:(H3 x B1D2):E3 | h3xb1d2_kf4 | h3xb1d2_kr2 |
| H3 x B1D2_v5 | E2:(H3 x B1D2) + E2:(H3 x B1D2) -> E2:E2 | h3xb1d2_kf5 | |
| H3 x B1D2_v6 | E2:(H3 x B1D2) + E2 -> E2:E2 | h3xb1d2_kf5 | |
| H3 x B1D2_v7 | E2:(H3 x B1D2) + E2_p -> E2:E2_p | h3xb1d2_kf5 | |
| H3 x B1D2_v8 | E2:(H3 x B1D2) + E1 -> E1:E2 | h3xb1d2_kf6 | |
| H3 x B1D2_v9 | E2:(H3 x B1D2) + E3 -> E2:E3 | h3xb1d2_kf6 | |
| H3 x B1D2_v10 | E2 + (H3 x B1D2):E3 -> E2:E3 | h3xb1d2_kf6 | |
| H3 x B1D2_v11 | E2:(H3 x B1D2) + E3:HRG -> E2:E3:HRG | h3xb1d2_kf7 | |
| H3 x B1D2_v12 | E2:(H3 x B1D2) + E3:HRG_p <-> E2:E3:HRG_p | h3xb1d2_kf7 | |
| H3 x B1D2_v13 | E1 + (H3 x B1D2):E3 -> E1:E3 | h3xb1d2_kf8 | |

\*\*In this reaction scheme, the amount of free (H3 x B1D2) is held constant.

TABLE 16B

H3 x B1D2 parameters

| Name | Value | Units |
|---|---|---|
| h3xb1d2_kf1 | 3.13E+04 | (mol/L)−1 sec−1 |
| h3xb1d2_kr1 | 1.50E−04 | sec−1 |

TABLE 16B-continued

H3 x B1D2 parameters

| Name | Value | Units |
|---|---|---|
| h3xb1d2_kf2 | 3.50E+05 | (mol/L)−1 sec−1 |
| h3xb1d2_kr2 | 2.20E−02 | sec−1 |
| h3xb1d2_kf3 | 1.08E−06 | (molecules/cell)−1 sec−1 |
| h3xb1d2_kf4 | 1.20E−05 | (molecules/cell)−1 sec−1 |
| h3xb1d2_kf5 | 1.67E−08 | (molecules/cell)−1 sec−1 |
| h3xb1d2_kf6 | 5.00E−08 | (molecules/cell)−1 sec−1 |
| h3xb1d2_kf7 | 5.00E−07 | (molecules/cell)−1 sec−1 |
| h3xb1d2_kf8 | 5.00E−08 | (molecules/cell)−1 sec−1 |

Figure 17:
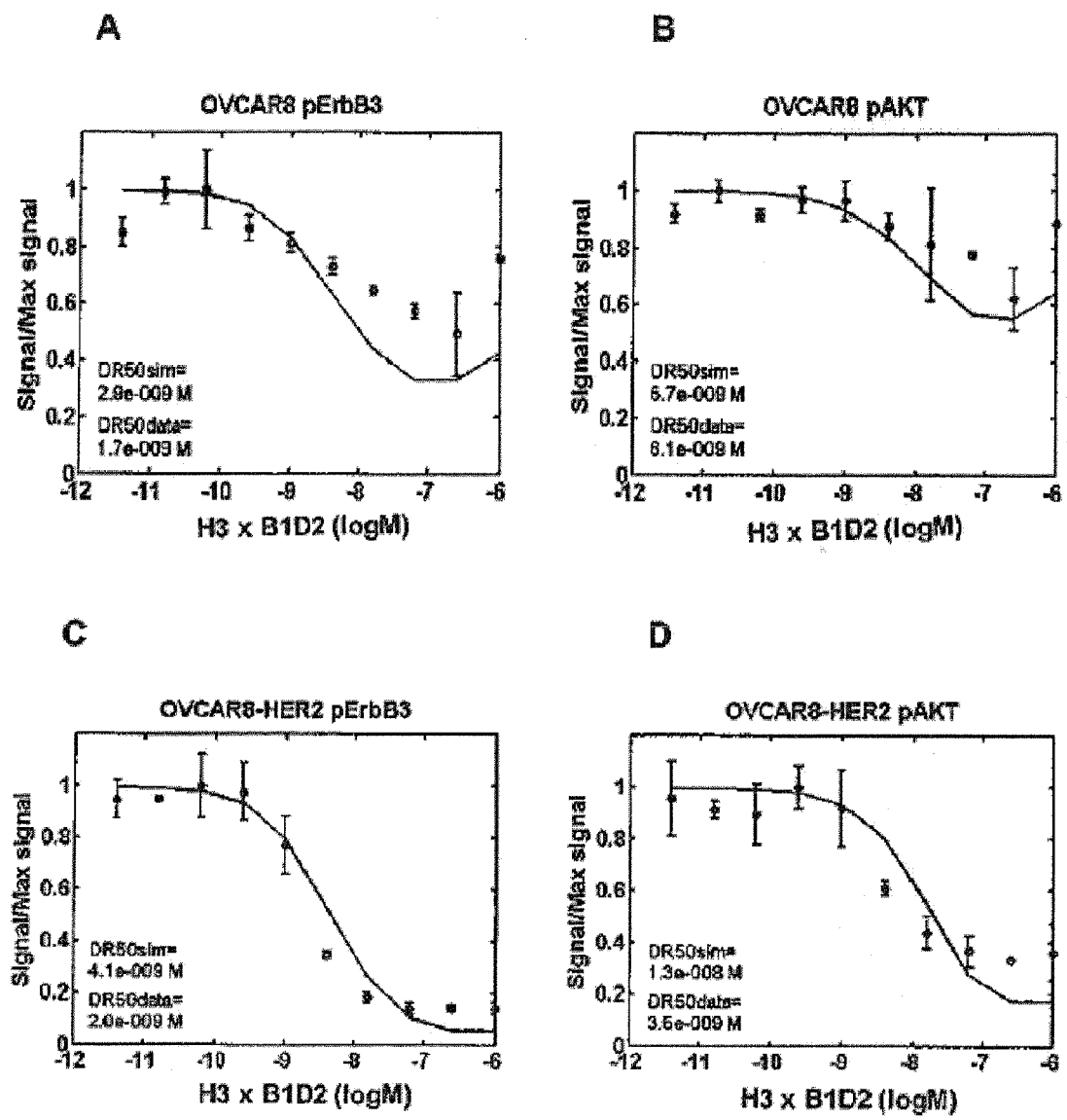
FIGS. 17A-D are graphs of inhibition curves for cells treated with the bispecific antibody H3×B1D2.

The ErbB signaling model was combined with the inhibitor model and used to predict experimental data for the inhibition of pErbB3 and pAKT signaling by H3×B1D2. The experimental data was generated using the same methodology as described above, except that concentrations of H3×B1D2 ranging from 15 pM to 1 μM were added during serum starvation. Additionally, inhibition data was generated using a ten-minute lysis timepoint after 5 nM HRG stimulation. The model successfully recapitulated experimental results showing that the $IC_{50}$ of inhibition for H3×B1D2 did not greatly change in different cell lines, but the percentage of inhibition did shift greatly. A primary cause of the change of percentage inhibition was the level of expression of ErbB2. This was demonstrated in experiments where ErbB2 was transfected into the OVCAR8 cell line to create an ErbB2-overexpressing cell line (referred to as OVCAR8-HER2). The pErbB3 and pAKT inhibition curves for OVCAR8 cells treated with H3×B1D2 were compared to the same inhibition curves for OVCAR8-HER2 cells treated with H3×B1D2. The results are shown in FIGS. 17A-D, wherein FIGS. 17A and 17B show the inhibition curves for pErbB3 and pAKT, respectively, in OVCAR8 cells treated with H3×B1D2 (either experimentally or simulated in the model) and FIGS. 17C and 17D show the inhibition curves for pErbB3 and pAKT, respectively, in OVCAR8-HER2 cells treated with H3×B1D2 (either experimentally or simulated in the model). The $IC_{50}$s for the experimentally treated cells ("DR50 data") and the simulated treated cells ("DR50sim") are also shown. The data show that higher levels of ErbB2 expression result in greater inhibition percentage by H3×B1D2 treatment.

Figure 18:
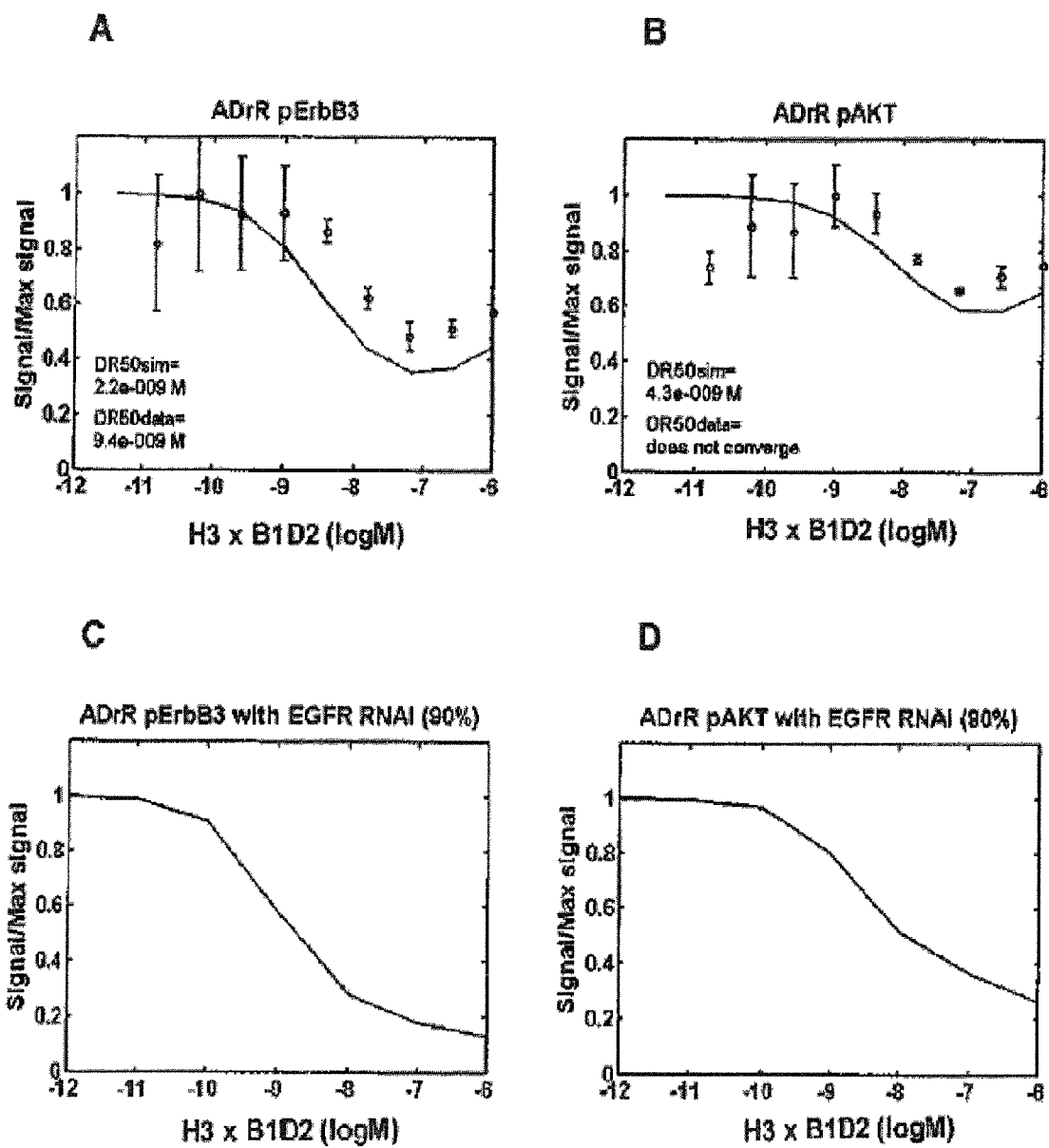
FIGS. 18A-D are graphs of inhibition curves for cells treated with the bispecific antibody H3×B1D2.

In addition to the primary role of ErbB2 in modulating percentage inhibition, an unexpected role for ErbB1 was revealed by the computational model. This role for ErbB1 was exemplified by a simulation showing the effect of adding ErbB1 RNAi to ADRr cells, to simulate downregulation of ErbB1. ADRr cells express only low levels of ErbB2 and exhibited a poor percentage of inhibition by H3×B1D2 in both the computational model and in experimentally determined data. This data is shown in FIGS. 18A and 18B, which show the inhibition curves for pErbB3 and pAKT, respectively, in ADRr cells treated with H3×B1D2, either experimentally or simulated in the model. The $IC_{50}$s for the experimentally treated cells ("DR50 data") and the simulated treated cells ("DR50sim") are also shown. However, downregulation of ErbB1 expression (by simulation of RNAi addition) resulted in a greater inhibition percentage in the simulation, as shown in FIGS. 18C and 18D, which show the inhibition curves for pErbB3 and pAKT, respectively, in ADRr cells simulated for treatment with ErbB1 RNA1 and H3×B1D2. The implication of the results from the ErbB1 RNAi simulation is that ErbB1 expression is a negative response biomarker for H3×B1D2.

In summary, the computational model and the experimental data indicated that there are two mechanisms for negatively modulating responsiveness to H3×B1D2 in vitro: (i) an insufficiently high ErbB2 level; and (ii) high ErbB1 levels. Conversely, high levels of ErbB2 expression and low levels of ErbB1 expression correlated with increased responsiveness to H3×B1D2.

Example 12

In Vivo Responsiveness to Treatment with H3×B1D2 Correlates with Predicted Responsiveness from a Computational Model In this example, the in vivo responsiveness of tumors to H3×B1D2 treatment was correlated with the computed levels of various components in the ErbB pathway to identify direct and indirect biomarkers for responsiveness to H3×B1D2 treatment.

To characterize the in vivo response of tumors to H3×B1D2 treatment, a panel of tumor cell lines was tested in a xenograft tumor model such as described in Example 1. In the xenograft tumor models, mice (nu/nu mice: 4-5 week old female mice, athymic, nude, outbred background; Albino; purchased from Charles River Labs, Wilmington, Mass.) are implanted in the flank with $5 \times 10^6$-$2 \times 10^7$ cells/mouse (depending on cell line) in 200 μl via subcutaneous injection. Mice are monitored for initial tumor growth. Tumors are allowed to grow for several days until the mean tumor volume is approximately 150-200 mm³. The tumor volume is calculated as $V=(\pi/6(L \times W^2)$. The mice are treated with the H3×B1D2 antibody at a dosage of 600 μg/injection every 3 days (q3d). Control mice are treated with phosphate buffered saline (PBS) or with wild-type HSA (human serum albumin). Tumor volume is measured for 40-80 days.

The following twelve tumor cell lines were examined: ACHN, ADRr, IGROV1, LS180, MIA PaCa2, ZR75-1, MDA-MB-361, ADrR-HER2 (ADrR cells transfected to overexpress HER2), NCI-N87, CALU-3, SKOV-3 and BT474-M3. For use of these cell lines in the computational model, the levels of ErbB1, ErbB2 and ErbB3 expression in each cell line was experimentally determined using the methods described above or minor variations thereof, the results of which are shown below in Table 17:

TABLE 17

ErbB ReceptorLevels

| Cell line | ErbB1 | ErbB2 | ErbB3 |
|---|---|---|---|
| ACHN | 448284 | 45456 | 15200 |
| ADrR | 177818 | 40792 | 33205 |
| BT474-M3 | 129436 | 1706601 | 49238 |
| SKOV3 | 264132 | 1377661 | 13694 |
| ZR75-1 | 37409 | 199132 | 39492 |
| IGROV1 | 149031 | 158418 | 5355 |
| OVCAR8 | 236157 | 53272 | 31813 |
| MDA-MB-361 | 65855 | 371731 | 32981 |
| NCI-N87 | 417753 | 1233479 | 34678 |
| Calu-3 | 161357 | 1196976 | 30031 |
| LS180 | 122520 | 143339 | 28841 |
| MIAPaCa-2 | 138563 | 84865 | 5735 |
| ADrR-HER2 | 271000 | 722000 | 34400 |

The control and treatment data from the in vivo xenograft experiments was fitted to exponential growth curves, using the following formula: $V=V_o*\exp(k*t)$ wherein V is the tumor volume, Vo is the tumor volume at time zero, k is the exponential growth rate and t is the time. The potency of H3×B1D2 in inhibiting tumor growth was represented as the ratio of treatment and control exponential growth rates for each cell line tested. This ratio was denoted "relative growth rate" (RGR) and is represented as:

$$RGR = k_{H3 \times B1D2}/k_{control}$$

A relative growth rate (RGR) of 1 meant the agent had no effect. An RGR of 0 meant that the agent halted tumor growth entirely. A negative RGR meant that the agent caused tumor regression.

Of the twelve cell lines examined, only BT474-M3 had a negative RGR (i.e., H3×B1D2 caused tumor regression only in this cell line). Two cell lines, IGROV1 and LS180, had RGR values greater than 1, indicating H3×B1D2 had no effect on tumor growth for these cell lines. The remaining nine cell lines had RGR values between 0 and 1, indicating that H3×B1D2 partially inhibited tumor growth for these cell lines.

Figure 19A:
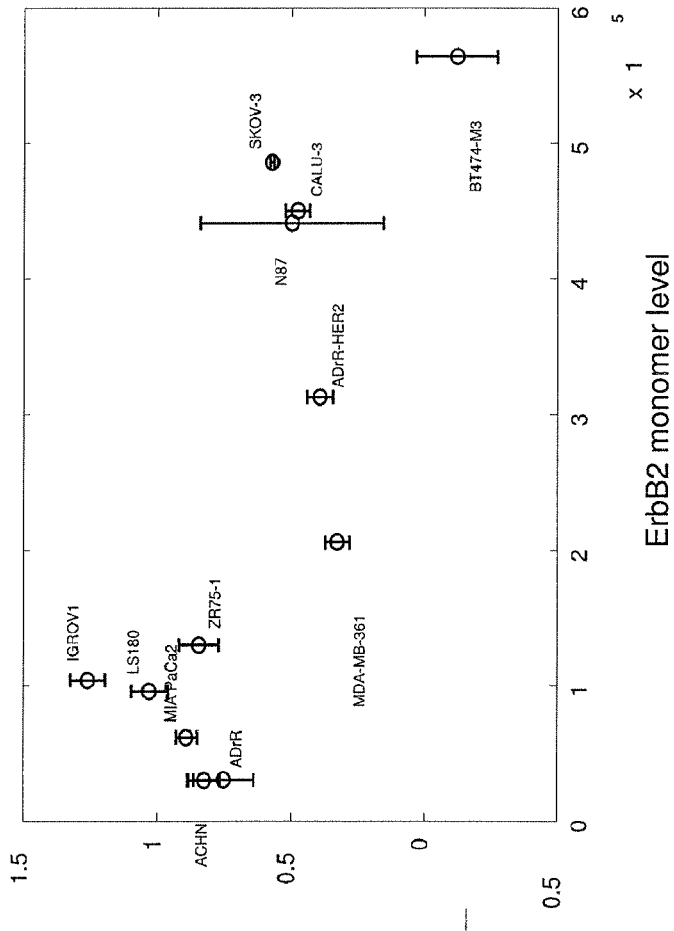
FIGS. 19A-C are graphs of the in vivo-determined relative growth rates (RGR) for a panel of tumor cells in a xenograft model treated with H3×B1D2 plotted against the computed levels of ErbB2 monomers (FIG. 19A), ErbB2:ErbB2 homodimers (FIG. 19B) and ErbB2:ErbB3 heterodimers (FIG. 19C) in the panel of tumor cells in the absence of H3×B1D2.
Figure 19B:
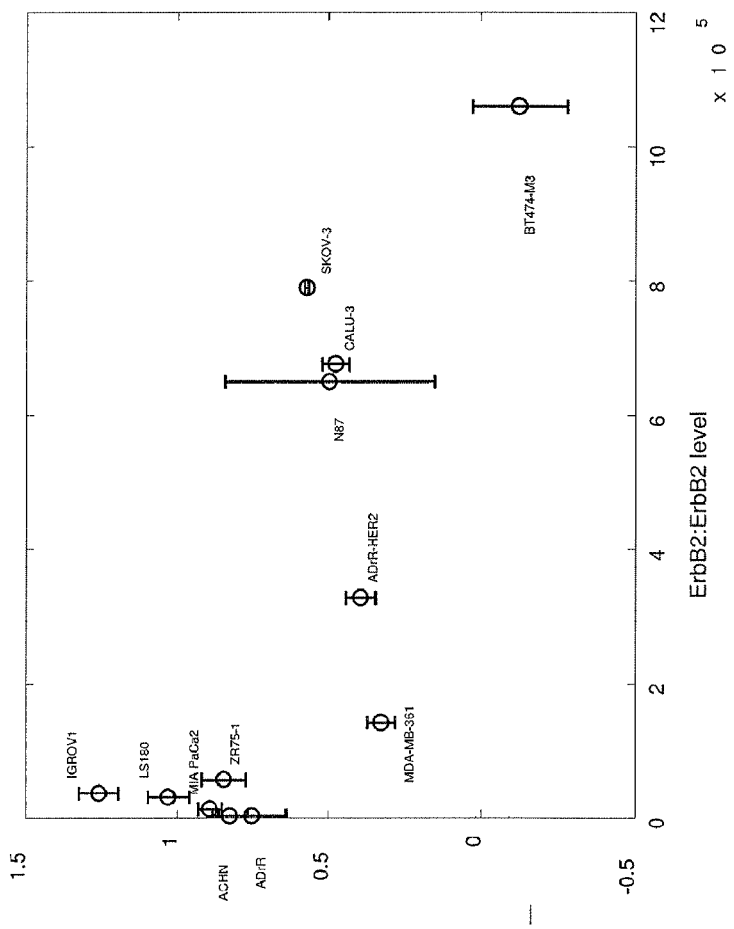
Figure 19C:
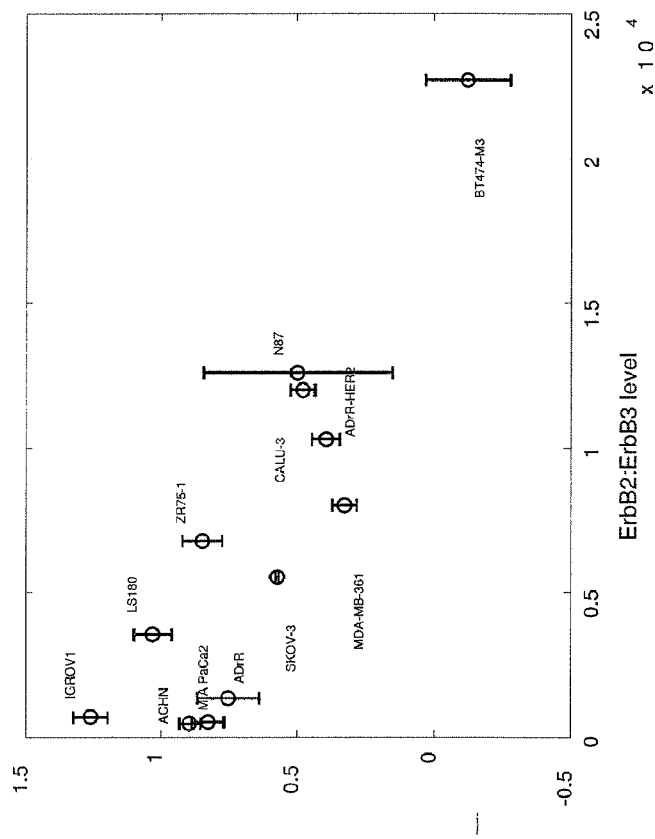

The RGR values for the twelve cell lines were plotted against model-computed levels of ErbB2 monomer, ErbB2:ErbB2 homodimer and ErbB2:ErbB3 heterodimer in the cell lines in the absence of the H3×B1D2 inhibitor, based on the measured levels of ErbB1, ErbB2 and ErbB3 in each of the cell lines. The results are illustrated in FIGS. 19A-C, which show graphs of the in vivo-determined relative growth rates (RGR) for the panel of tumor cells in the xenograft model treated with H3×B1D2 plotted against the computed levels of ErbB2 monomers (FIG. 19A), ErbB2:ErbB2 homodimers (FIG. 19B) and ErbB2:ErbB3 heterodimers (FIG. 19C) in the panel of tumor cells in the absence of H3×B1D2.

The results in FIG. 19 show that there is a linear relationship between RGR and computed levels of ErbB2 monomers, ErbB2:ErbB2 homodimers and ErbB2:ErbB3 heterodimers. In view of this observation, direct measurement of ErbB2 monomers, ErbB2:ErbB2 homodimers and/or ErbB2:ErbB3 heterodimers can be used as direct biomarkers of H3×B1D2 responsiveness. Furthermore, measurement of ErbB1, ErbB2 and ErbB3 in a tumor sample can be used to compute the levels of ErbB2:ErbB2 homodimers and/or ErbB2:ErbB3 heterodimers to stratify tumor responsiveness to H3×B1D2 treatment (i.e., measured levels of ErbB1, ErbB2 and ErbB3 can be used as indirect biomarkers of H3×B1D2 responsiveness, which are used to compute levels of ErbB2:ErbB2 homodimers and/or ErbB2:ErbB3 heterodimers). Thus, computed levels of, for example, ErbB2:ErbB2 homodimers and/or ErbB2:ErbB3 heterodimers can be used as a Network Activation State (NAS) value upon which responsiveness to H3×B1D2 treatment can be predicted.

Figure 20A:
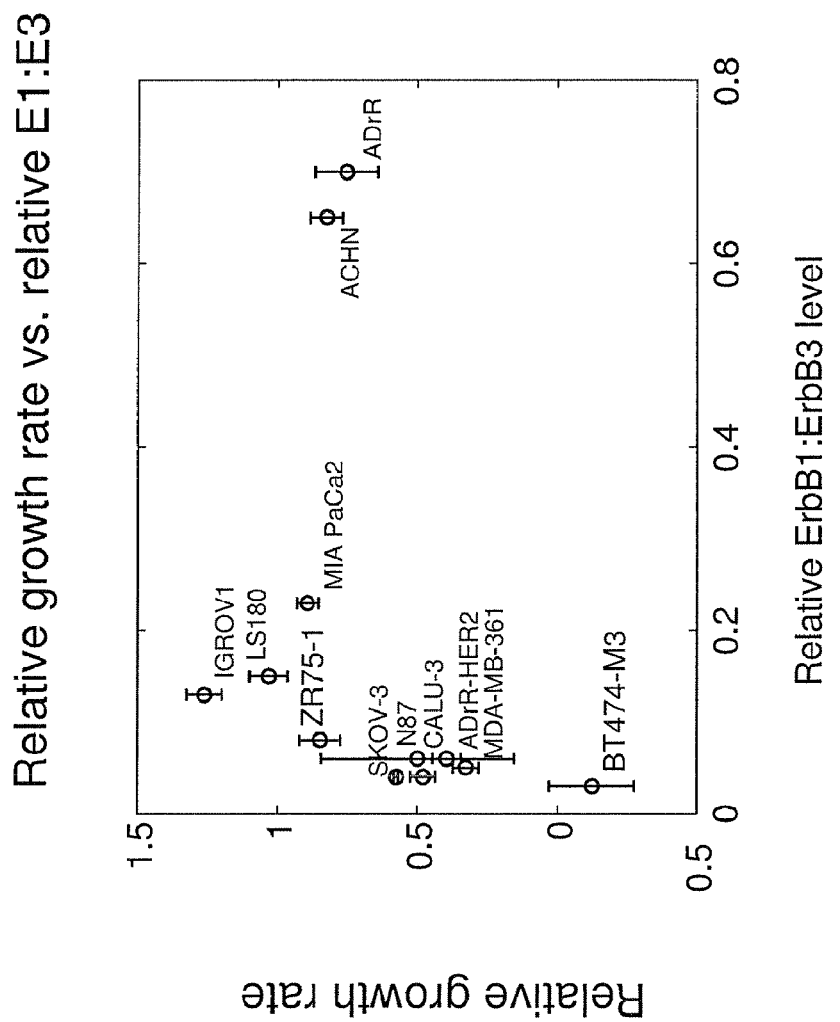
FIGS. 20A-B are graphs of the in vivo-determined relative growth rates (RGR) for a panel of tumor cells in a xenograft model treated with H3×B1D2 plotted against the computed relative levels of ErbB2:ErbB3 heterodimers (FIG. 20A) and ErbB1:ErbB3 heterodimers (FIG. 20B) in the panel of tumor cells in the simulated absence and presence of H3×B1D2.
Figure 20B:
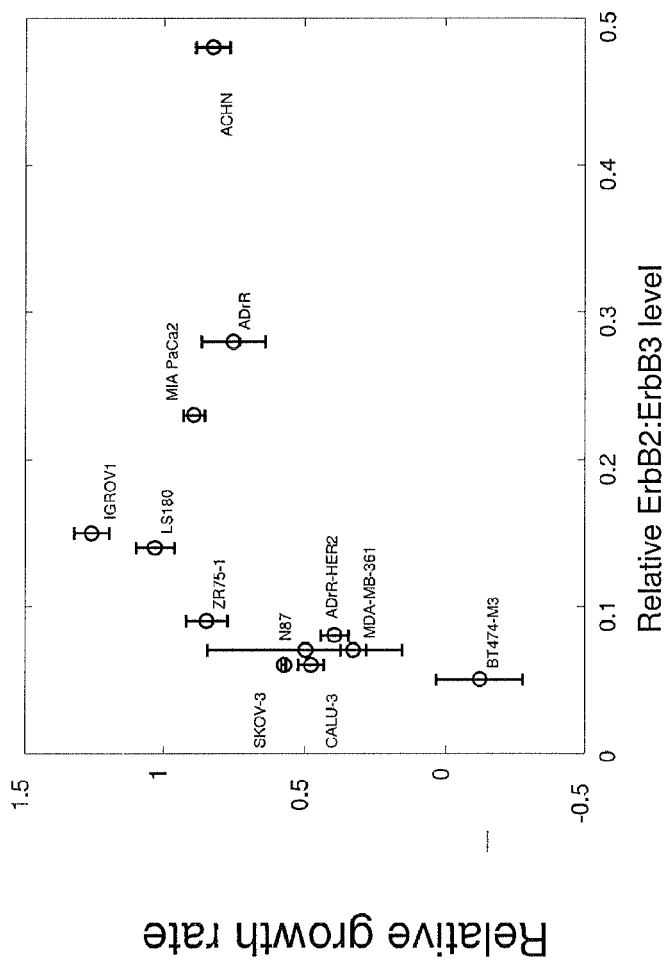

The RGR values for the twelve cell lines also were plotted against the computed relative levels (e.g., ratio) of ErbB2:ErbB2 heterodimer and ErbB1:ErbB3 heterodimer in the cell lines in the simulated absence and presence of the H3×B1D2 inhibitor. A lower relative level indicates that H3×B1D2 can more potently inhibit formation of that species of heterodimer. The results are illustrated in FIGS. 20A-B, which show graphs of the in vivo-determined relative growth rates (RGR) for a panel of tumor cells in a xenograft model treated with H3×B1D2 plotted against the computed relative levels of ErbB2:ErbB3 heterodimers (FIG. 20A) and ErbB1:ErbB3 heterodimers (FIG. 20B) in the panel of tumor cells in the simulated presence of H3×B1D2, as compared to the simulated levels of the heterodimers in the simulated absence of H3×B1D2.

The results in FIG. 20 demonstrate a correlation between the ability of the inhibitor to disrupt ErbB2:ErbB3 and ErbB1:ErbB3 heterodimers and the relative growth rate of the tumors. That is, tumor cells (e.g., BT474-M3 cells) in which the computed relative levels of ErbB2:ErbB3 and ErbB1:ErbB3 heterodimer are low in the simulated presence of the H3×B1D2 inhibitor (i.e., heterodimer disruption is high by the inhibitor) exhibit lower RGR values (indicating a greater effect of the inhibitor on tumor growth). In contrast, tumor cells (e.g., ACHN cells) in which the computed relative levels of ErbB2:ErbB3 and ErbB1:ErbB3 heterodimer are high in the simulated presence of the H3×B1D2 inhibitor (i.e., heterodimer disruption is low by the inhibitor) exhibit higher RGR values (indicating less of an effect of the inhibitor on tumor growth). These results demonstrate that simulating the presence of the therapeutic agent in the computational model of the signaling pathway, as compared to the simulated absence of the therapeutic agent, allows for generation of a Network Inhibition State (NIS), based on the relative levels of ErbB2:ErbB3 or ErbB1:ErbB3 heterodimer, which NIS can be used as a predictor of the responsiveness of tumor cells to the therapeutic agent in vivo.

Example 13

Measurement of Binding Affinity ($K_D$)

The dissociation constants of anti-ErbB antibodies may be measured using either or both of two independent techniques, a Surface Plasmon Resonance Assay and a cell binding assay.

Surface Plasmon Resonance Assay

The Surface Plasmon Resonance Assay is performed as described in Wassaf et al. (2006) *Analytical Biochem.*, 351:241-253. A preferred implementation uses a BIACORE 3000 instrument (GE Healthcare) using a recombinant ErbB protein as the analyte and the anti-ErbB antibody as the ligand The $K_D$ value is calculated based on the formula $K_D = K_d/K_a$.

Cell Binding Assay

A cell binding assay is performed using A-431 cells for ErbB1 binding, ZR-75-1 cells for ErbB2 binding or MALME-3M cells for ErbB3 binding (all from ATCC). The assay is performed substantially as follows.

Cells are detached with 2 mLs trypsin-EDTA+2 mLs RMPI+5 mM EDTA at room temperature for 5 minutes. Complete RPMI (10 mLs) is added immediately to the trypsinized cells, resuspended gently and spun down in a Beckman tabletop centrifuge at 1100 rpm for 5 minutes. Cells are resuspended in BD stain buffer (PBS+2% FBS+0.1% sodium azide, Becton Dickinson) at a concentration of $2 \times 10^6$ cells per ml and 50 µl ($1 \times 10^5$ cells) aliquots are plated in a 96-well titer plate.

A 150 µl solution of 200 nM anti-ErbB antibody in BD stain buffer is prepared and serially diluted 2-fold into 75 µl BD stain buffer. The concentrations of the diluted antibody ranged from 200 nM to 0.4 nM. 50 µl aliquots of the different protein dilutions are then added directly to the 50 ul cell suspension giving the final concentrations of 100 nM, 50 nM, 25 nM, 12 nM, 6 nM, 3 nM, 1.5 nM, 0.8 nM, 0.4 nM and 0.2 nM of the antibody.

Aliquoted cells in the 96-well plate are incubated with the protein dilutions for 30 minutes at room temperature on a platform shaker and washed 3 times with 300 µl BD stain buffer. Cells are then incubated with 100 µl of secondary antibody (e.g., a 1:750 dilution of Alexa 647-labeled goat anti-human IgG in BD stain buffer) for 45 minutes on a platform shaker in the cold room. Finally, cells are washed twice, pelleted and resuspended in 250 µl BD stain buffer+0.5 µg/ml propidium iodide. Analysis of 10,000 cells is done in a FACSCALIBUR flow cytometer using the FL4 channel. MFI values and the corresponding concentrations of the anti-ErbB-antibody are plotted on the y-axis and x-axis, respectively. The $K_D$ of the molecule is determined using GraphPad PRISM software using the one-site binding model for a non-linear regression curve.

The $K_D$ value is calculated based on the formula Y=Bmax*X/$K_D$+X(Bmax=fluorescence at saturation. X=antibody concentration. Y=degree of binding).

What is claimed is:

1. A method of selecting anti-ErbB3 therapy for a patient having a neoplastic tumor, said method comprising:
 (a) obtaining a sample of the tumor,
 (b) determining a level of pErbB3 in the sample by indirect measurement that includes: measuring total protein in the sample and levels of (i) at least one receptor selected from ErbB1, ErbB2, and ErbB3 and (ii) at least one of heregulin and betacellulin,
 (c) comparing the level of pErbB3 in the sample to a level of pErbB3 directly measured in a culture of ACHN cells following culture for 20-24 hours in serum-free medium, and subsequently administering an anti-ErbB3 therapeutic agent to the patient only when the level of pErbB3 determined in the sample is no lower than 50% of the level of pErbB3 measured in the culture of ACHN cells following culture for 20-24 hours in serum-free medium.

2. The method of claim 1, wherein the at least one receptor is ErbB3.

3. The method of claim 1, wherein the at least one receptor is ErbB3 and the at least one of heregulin and betacelulin is heregulin.

4. A method according to claim 1, wherein the anti-ErbB3 therapeutic agent is an anti-ErbB3 antibody.

5. A method according to claim 4, wherein the anti-ErbB3 antibody comprises at least one of:
 (i) an antibody comprising heavy chain variable region ($V_H$) and light chain variable region ($V_L$) sequences as shown in SEQ ID NOs: 1 and 2, respectively, or an antibody comprising $V_H$ and $V_L$ CDR sequences as shown in SEQ ID NOs: 7-9 and 10-12, respectively;
 (ii) an antibody comprising $V_H$ and $V_L$ sequences as shown in SEQ ID NOs: 3 and 4, respectively, or an antibody comprising $V_H$ and $V_L$ CDR sequences shown in SEQ ID NOs: 13-15 and 16-18, respectively;
 (iii) an antibody comprising $V_H$ and $V_L$ sequences as shown in SEQ ID NOs: 5 and 6, respectively, or an antibody comprising $V_H$ and $V_L$ CDR sequences shown in SEQ ID NOs: 19-21 and 22-24, respectively;
 (iv) an antibody comprising $V_H$ and $V_L$ sequences as shown in SEQ ID NOs: 25 and 26, respectively, or an antibody comprising $V_H$ and $V_L$ CDR sequences shown in SEQ ID NOs: 27-29 and 30-32, respectively; and
 (v) an antibody comprising $V_H$ and $V_L$ sequences as shown in SEQ ID NOs: 33 and 34, respectively, or an antibody comprising $V_H$ and $V_L$ CDR sequences shown in SEQ ID NOs: 35-37 and 38-40, respectively.

6. A method according to claim 4, wherein the anti-ErbB3 antibody comprises MM-121.

7. A method according to claim 1, wherein at least one of the at least one receptor selected from ErbB1, ErbB2, and ErbB3 and the at least one of ligands heregulin and betacellulin for which a level is measured is at least one protein and wherein the level of the at least one protein is measured by quantitative fluorescence activated cell sorting, enzyme linked immunosorbent assay, immunohistochemistry, quantitative immunohistochemistry, fluorescence resonance energy transfer, Forster resonance energy transfer, biomolecular fluorescence complementation, mass spectrometry, immunoblot assay or coimmunoprecipitation assay.

8. A method according to claim 1, wherein at least one of the at least one receptor selected from ErbB1, ErbB2, and ErbB3 and the at least one of heregulin and betacellulin for which a level is measured is an mRNA.

9. A method according to claim 1, wherein the tumor is a breast cancer tumor.

10. A method according to claim 1, wherein the tumor is a tumor of a tissue selected from of lung, rectum, gall bladder, brain, spinal cord, breast, kidney, pancreas, stomach, colon, liver, bone, skin, spleen, ovary, testis, prostate and muscle.

11. A method according to claim 1, wherein the sample of the tumor is selected from tumor tissue, fine needle aspirate, nipple aspirate, circulating tumor cells isolated from a blood sample, whole blood, serum, plasma, lymph, saliva and urine, or shed or circulating tumor cells isolated therefrom.

* * * * *

UNITED STATES PATENT AND TRADEMARK OFFICE
CERTIFICATE OF CORRECTION

PATENT NO. : 8,623,592 B2  
APPLICATION NO. : 13/058687  
DATED : January 7, 2014  
INVENTOR(S) : Schoeberl et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 187 days.

Signed and Sealed this
Twenty-fifth Day of August, 2015

Michelle K. Lee
*Director of the United States Patent and Trademark Office*

```
                          SEQUENCE LISTING

<160> NUMBER OF SEQ ID NOS: 53

<210> SEQ ID NO 1
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser
        115

<210> SEQ ID NO 2
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Ile Phe Val Ile Phe Gly Gly Gly Thr Lys Val Thr Val Leu
            100                 105                 110

<210> SEQ ID NO 3
```

```
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Arg Trp Val Arg Gln Ala Pro Gly Lys Gly Leu Glu Trp Val
        35                  40                  45

Ser Val Ile Tyr Pro Ser Gly Gly Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Tyr Gly Met Asp Val Trp Gly Gln Gly Thr
            100                 105                 110

Leu Val Thr Val Ser Ser
            115

```
<210> SEQ ID NO 4
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

Gln Ser Val Leu Thr Gln Pro Pro Ser Ala Ser Gly Thr Pro Gly Gln
1               5                   10                  15

Arg Val Thr Ile Ser Cys Ser Gly Ser Asp Ser Asn Ile Gly Arg Asn
            20                  25                  30

Tyr Ile Tyr Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Ile Ser
    50                  55                  60

Gly Ser Lys Ser Gly Thr Ser Ala Ser Leu Ala Ile Ser Gly Leu Arg
65                  70                  75                  80

Ser Glu Asp Glu Ala Glu Tyr His Cys Gly Thr Trp Asp Asp Ser Leu
                85                  90                  95

Ser Gly Pro Val Phe Gly Gly Gly Thr Lys Leu Thr Val Leu
            100                 105                 110

```
<210> SEQ ID NO 5
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5
```

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Ser Ala Tyr
            20                  25                  30

Gly Met Gly Trp Val Arg Gln Ala Pro Gly Lys Gly Leu Glu Trp Val
            35                  40                  45

Ser Tyr Ile Ser Pro Ser Gly His Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Glu Thr Gly Leu Leu Val Asp Ala Phe Asp Ile Trp
            100                 105                 110

Gly Gln Gly Thr Met Val Thr Val Ser Ser
            115                 120

<210> SEQ ID NO 6
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Tyr Glu Leu Thr Gln Pro Pro Ser Val Ser Val Tyr Pro Gly Gln
1               5                   10                  15

Thr Ala Ser Ile Thr Cys Ser Gly Asp Gln Leu Gly Ser Lys Phe Val
            20                  25                  30

Ser Trp Tyr Gln Gln Arg Pro Gly Gln Ser Pro Val Leu Val Met Tyr
            35                  40                  45

Lys Asp Lys Arg Arg Pro Ser Glu Ile Pro Glu Arg Phe Ser Gly Ser
        50                  55                  60

Asn Ser Gly Asn Thr Ala Thr Leu Thr Ile Ser Gly Thr Gln Ala Ile
65                  70                  75                  80

Asp Glu Ala Asp Tyr Tyr Cys Gln Ala Trp Asp Ser Ser Thr Tyr Val
                85                  90                  95

Phe Gly Thr Gly Thr Lys Val Thr Val Leu
            100                 105

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

His Tyr Val Met Ala
1               5

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 8

Ser Ile Ser Ser Ser Gly Gly Trp Thr Leu Tyr Ala Asp Ser Val Lys
1               5                   10                  15
Gly

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Leu Lys Met Ala Thr Ile Phe Asp Tyr
1               5                   10

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Gly Thr Ser Ser Asp Val Gly Ser Tyr Asn Val Val Ser
1               5                   10

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Glu Val Ser Gln Arg Pro Ser
1               5

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Cys Ser Tyr Ala Gly Ser Ser Ile Phe Val Ile
1               5                   10

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13
```

```
Ala Tyr Asn Met Arg
1               5
```

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Val Ile Tyr Pro Ser Gly Gly Ala Thr Arg Tyr Ala Asp Ser Val Lys
1               5                   10                  15
Gly
```

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

```
Gly Tyr Tyr Tyr Tyr Gly Met Asp Val
1               5
```

<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

```
Ser Gly Ser Asp Ser Asn Ile Gly Arg Asn Tyr Ile Tyr
1               5                   10
```

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

```
Arg Asn Asn Gln Arg Pro Ser
1               5
```

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

```
Gly Thr Trp Asp Asp Ser Leu Ser Gly Pro Val
1               5                   10
```

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ala Tyr Gly Met Gly
1               5

<210> SEQ ID NO 20
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Tyr Ile Ser Pro Ser Gly Gly His Thr Lys Tyr Ala Asp Ser Val Lys
1               5                   10                  15

Gly

<210> SEQ ID NO 21
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Leu Glu Thr Gly Leu Leu Val Asp Ala Phe Asp Ile
1               5                   10

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Gly Asp Gln Leu Gly Ser Lys Phe Val Ser
1               5                   10

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Tyr Lys Asp Lys Arg Arg Pro Ser
1               5

<210> SEQ ID NO 24
<211> LENGTH: 9

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Ala Trp Asp Ser Ser Thr Tyr Val
1               5

<210> SEQ ID NO 25
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gly Met Gly Trp Val Arg Gln Ala Pro Gly Lys Gly Leu Glu Trp Val
        35                  40                  45

Ser Tyr Ile Ser Pro Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asn Tyr Tyr Tyr Gly Leu Asp Val Trp Gly Gln Gly Thr
            100                 105                 110

Thr Val Thr Val Ser Ser
            115

<210> SEQ ID NO 26
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Asp Ile Gln Met Thr Gln Ser Pro Ser Ser Leu Ser Ala Ser Val
1               5                   10                  15

Gly Asp Arg Ile Thr Ile Thr Cys Gln Ala Ser Gln Asp Ile Gly Asp
            20                  25                  30

Ser Leu Asn Trp Tyr Gln Gln Lys Pro Gly Lys Ala Pro Arg Leu Leu
        35                  40                  45

Ile Tyr Asp Ala Ser Asn Leu Glu Thr Gly Val Pro Pro Arg Phe Ser
    50                  55                  60

Gly Ser Gly Ser Gly Thr Asp Phe Thr Phe Thr Phe Arg Ser Leu Gln
65                  70                  75                  80

Pro Glu Asp Ile Ala Thr Tyr Phe Cys Gln Gln Ser Ala Asn Ala Pro
                85                  90                  95

Phe Thr Phe Gly Pro Gly Thr Lys Val Asp Ile Lys
            100                 105
```

```
<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Trp Tyr Gly Met Gly
1               5

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Tyr Ile Ser Pro Ser Gly Gly Ile Thr Val Tyr Ala Asp Ser Val Lys
1               5                   10                  15

Gly

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Leu Asn Tyr Tyr Tyr Gly Leu Asp Val
1               5

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Ala Ser Gln Asp Ile Gly Asp Ser Leu Asn
1               5                   10

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Asp Ala Ser Asn Leu Glu Thr
1               5

<210> SEQ ID NO 32
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Gln Ser Ala Asn Ala Pro Phe Thr
1               5

<210> SEQ ID NO 33
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Trp Trp Val Arg Gln Ala Pro Gly Lys Gly Leu Glu Trp Val
        35                  40                  45

Ser Tyr Ile Gly Ser Ser Gly Gly Pro Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Gly Thr Pro Tyr Tyr Phe Asp Ser Trp Gly Gln Gly
            100                 105                 110

Thr Leu Val Thr Val Ser Ser
        115

<210> SEQ ID NO 34
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Tyr Glu Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Arg Trp
            20                  25                  30

Asn Ile Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
```

```
<210> SEQ ID NO 35
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Arg Tyr Gly Met Trp
1               5

<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Tyr Ile Gly Ser Ser Gly Gly Pro Thr Tyr Tyr Val Asp Ser Val Lys
1               5                   10                  15

Gly

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Arg Gly Thr Pro Tyr Tyr Phe Asp Ser
1               5                   10

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Thr Gly Thr Ser Ser Asp Ile Gly Arg Trp Asn Ile Val Ser
1               5                   10

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Val Ser Asn Arg Pro Ser
1               5
```

```
<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ser Ser Tyr Thr Ser Ser Ser Thr Trp Val
1               5                   10

<210> SEQ ID NO 41
<211> LENGTH: 1095
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Glu Ala Asp Tyr
    210                 215                 220

Tyr Cys Ser Ser Tyr Gly Ser Ser Thr His Val Ile Phe Gly Gly
225                 230                 235                 240

Gly Thr Lys Val Thr Val Leu Gly Ala Ala Ser Asp Ala His Lys Ser
                245                 250                 255

Glu Val Ala His Arg Phe Lys Asp Leu Gly Glu Glu Asn Phe Lys Ala
            260                 265                 270

Leu Val Leu Ile Ala Phe Ala Gln Tyr Leu Gln Gln Ser Pro Phe Glu
        275                 280                 285
```

```
Asp His Val Lys Leu Val Asn Glu Val Thr Glu Phe Ala Lys Thr Cys
290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
                340                 345                 350

Phe Leu Gln His Lys Asp Asp Asn Pro Asn Leu Pro Arg Leu Val Arg
            355                 360                 365

Pro Glu Val Asp Val Met Cys Thr Ala Phe His Asp Asn Glu Glu Thr
370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
                420                 425                 430

Leu Asp Glu Leu Arg Asp Glu Gly Lys Ala Ser Ser Ala Lys Gln Arg
            435                 440                 445

Leu Lys Cys Ala Ser Leu Gln Lys Phe Gly Glu Arg Ala Phe Lys Ala
        450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
                500                 505                 510

Lys Tyr Ile Cys Glu Asn Gln Asp Ser Ile Ser Ser Lys Leu Lys Glu
            515                 520                 525

Cys Cys Glu Lys Pro Leu Leu Glu Lys Ser His Cys Ile Ala Glu Val
530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Arg His Pro Asp Tyr
                580                 585                 590

Ser Val Val Leu Leu Leu Arg Leu Ala Lys Thr Tyr Glu Thr Thr Leu
            595                 600                 605

Glu Lys Cys Cys Ala Ala Ala Asp Pro His Glu Cys Tyr Ala Lys Val
        610                 615                 620

Phe Asp Glu Phe Lys Pro Leu Val Glu Glu Pro Gln Asn Leu Ile Lys
625                 630                 635                 640

Gln Asn Cys Glu Leu Phe Glu Gln Leu Gly Glu Tyr Lys Phe Gln Asn
                645                 650                 655

Ala Leu Leu Val Arg Tyr Thr Lys Lys Val Pro Gln Val Ser Thr Pro
            660                 665                 670

Thr Leu Val Glu Val Ser Arg Asn Leu Gly Lys Val Gly Ser Lys Cys
        675                 680                 685

Cys Lys His Pro Glu Ala Lys Arg Met Pro Cys Ala Glu Asp Tyr Leu
        690                 695                 700

Ser Val Val Leu Asn Gln Leu Cys Val Leu His Glu Lys Thr Pro Val
705                 710                 715                 720
```

Ser Asp Arg Val Thr Lys Cys Cys Thr Glu Ser Leu Val Asn Arg Arg
            725                 730                 735

Pro Cys Phe Ser Ala Leu Glu Val Asp Glu Thr Tyr Val Pro Lys Glu
            740                 745                 750

Phe Gln Ala Glu Thr Phe Thr Phe His Ala Asp Ile Cys Thr Leu Ser
            755                 760                 765

Glu Lys Glu Arg Gln Ile Lys Lys Gln Thr Ala Leu Val Glu Leu Val
770                 775                 780

Lys His Lys Pro Lys Ala Thr Lys Glu Gln Leu Lys Ala Val Met Asp
785             790                  795                 800

Asp Phe Ala Ala Phe Val Glu Lys Cys Cys Lys Ala Asp Asp Lys Glu
                805                 810                 815

Thr Cys Phe Ala Glu Glu Gly Lys Lys Leu Val Ala Ala Ser Gln Ala
            820                 825                 830

Ala Leu Gly Leu Ala Ala Ala Leu Gln Val Gln Leu Val Gln Ser Gly
            835                 840                 845

Ala Glu Val Lys Lys Pro Gly Glu Ser Leu Lys Ile Ser Cys Lys Gly
850                 855                 860

Ser Gly Tyr Ser Phe Thr Ser Tyr Trp Ile Ala Trp Val Arg Gln Met
865                 870                 875                 880

Pro Gly Lys Gly Leu Glu Tyr Met Gly Leu Ile Tyr Pro Gly Asp Ser
                885                 890                 895

Asp Thr Lys Tyr Ser Pro Ser Phe Gln Gly Gln Val Thr Ile Ser Val
            900                 905                 910

Asp Lys Ser Val Ser Thr Ala Tyr Leu Gln Trp Ser Ser Leu Lys Pro
            915                 920                 925

Ser Asp Ser Ala Val Tyr Phe Cys Ala Arg His Asp Val Gly Tyr Cys
            930                 935                 940

Thr Asp Arg Thr Cys Ala Lys Trp Pro Glu Trp Leu Gly Val Trp Gly
945                 950                 955                 960

Gln Gly Thr Leu Val Thr Val Ser Ser Gly Gly Gly Gly Ser Gly
                965                 970                 975

Gly Gly Ser Gly Gly Gly Ser Gln Ser Val Leu Thr Gln Pro Pro
            980                 985                 990

Ser Val Ser Ala Ala Pro Gly Gln Lys Val Thr Ile Ser Cys Ser Gly
            995                 1000                1005

Ser Ser Ser Asn Ile Gly Asn Asn Tyr Val Ser Trp Tyr Gln Gln
    1010            1015                1020

Leu Pro Gly Thr Ala Pro Lys Leu Leu Ile Tyr Asp His Thr Asn
    1025            1030                1035

Arg Pro Ala Gly Val Pro Asp Arg Phe Ser Gly Ser Lys Ser Gly
    1040            1045                1050

Thr Ser Ala Ser Leu Ala Ile Ser Gly Phe Arg Ser Glu Asp Glu
    1055            1060                1065

Ala Asp Tyr Tyr Cys Ala Ser Trp Asp Tyr Thr Leu Ser Gly Trp
    1070            1075                1080

Val Phe Gly Gly Gly Thr Lys Leu Thr Val Leu Gly
    1085            1090

<210> SEQ ID NO 42
<211> LENGTH: 5
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 42

Ser Tyr Trp Met Ser
1               5

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Asn Ile Asn Arg Asp Gly Ser Ala Ser Tyr Tyr Val Asp Ser Val Lys
1               5                   10                  15

Gly

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Asp Arg Gly Val Gly Tyr Phe Asp Leu
1               5

<210> SEQ ID NO 45
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Thr Gly Thr Ser Ser Asp Val Gly Gly Tyr Asn Phe Val Ser
1               5                   10

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asp Val Ser Asp Arg Pro Ser
1               5

<210> SEQ ID NO 47
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 47

Ser Ser Tyr Gly Ser Ser Ser Thr His Val Ile
1               5                   10

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ser Tyr Trp Ile Ala
1               5

<210> SEQ ID NO 49
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Leu Ile Tyr Pro Gly Asp Ser Asp Thr Lys Tyr Ser Pro Ser Phe Gln
1               5                   10                  15

Gly

<210> SEQ ID NO 50
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

His Asp Val Gly Tyr Cys Thr Asp Arg Thr Cys Ala Lys Trp Pro Glu
1               5                   10                  15

Trp Leu Gly Val
            20

<210> SEQ ID NO 51
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Gly Ser Ser Ser Asn Ile Gly Asn Asn Tyr Val Ser
1               5                   10

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 52

Asp His Thr Asn Arg Pro Ala
1               5

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ala Ser Trp Asp Tyr Thr Leu Ser Gly Trp Val
1               5                   10
```